(12) United States Patent  
Hoang

(10) Patent No.: US 10,335,446 B2
(45) Date of Patent: Jul. 2, 2019

(54) METHODS OF TREATING DISEASES USING GRAPE PROTEINS

(71) Applicant: Kieu Hoang, Westlake Village, CA (US)

(72) Inventor: Kieu Hoang, Westlake Village, CA (US)

(*) Notice: Subject to any disclaimer, the term of this patent is extended or adjusted under 35 U.S.C. 154(b) by 0 days.

(21) Appl. No.: 15/934,406

(22) Filed: Mar. 23, 2018

(65) Prior Publication Data

US 2019/0000910 A1 Jan. 3, 2019

Related U.S. Application Data

(63) Continuation of application No. PCT/US2016/053258, filed on Sep. 23, 2016.

(60) Provisional application No. 62/222,317, filed on Sep. 23, 2015.

(51) Int. Cl.

| A61K 36/00 | (2006.01) |
|---|---|
| A61K 36/87 | (2006.01) |
| A23J 1/14 | (2006.01) |
| A61K 38/16 | (2006.01) |
| A23L 19/00 | (2016.01) |
| A61P 35/02 | (2006.01) |
| A61K 9/00 | (2006.01) |
| A61Q 19/08 | (2006.01) |
| A61K 8/9789 | (2017.01) |
| A23J 1/00 | (2006.01) |
| A23L 2/66 | (2006.01) |
| A23L 33/185 | (2016.01) |

(52) U.S. Cl.
CPC ............... *A61K 36/87* (2013.01); *A23J 1/006* (2013.01); *A23J 1/14* (2013.01); *A23L 2/66* (2013.01); *A23L 19/07* (2016.08); *A23L 33/185* (2016.08); *A61K 8/9789* (2017.08); *A61K 9/0053* (2013.01); *A61K 38/168* (2013.01); *A61P 35/02* (2018.01); *A61Q 19/08* (2013.01); *A61K 2236/15* (2013.01); *A61K 2236/19* (2013.01); *A61K 2236/30* (2013.01)

(58) Field of Classification Search
CPC ....................................................... A61K 36/00
USPC .......................................................... 424/725
See application file for complete search history.

(56) References Cited

FOREIGN PATENT DOCUMENTS

CN 104435544 A * 3/2015

* cited by examiner

Primary Examiner — Michael V Meller
(74) Attorney, Agent, or Firm — Merek, Blackmon & Voorhees, LLC

(57) ABSTRACT

A food composition for human consumption comprising a plurality of grape ingredients, wherein the plurality of grape ingredients comprise ground flesh, seed, stem, and skin from grapes, and wherein the plurality of grape ingredients further comprise one or more KH Grape proteins. A method of treating a certain disease in a patient comprising administering the food composition to a patient in need thereof, wherein the food composition has a concentration of KH Grape protein above 0%.

6 Claims, 54 Drawing Sheets

Figure 2

|  | TC (μg/μl) | HDL (μg/μl) | LDL/VLDL (μg/μl) | TG (mmol/L) |  |
|---|---|---|---|---|---|
| KH101 | 0.000 | 0.006 | 0.001 | 0.013 | ← Rice |
| KH102 | 0.002 | 0.004 | 0.001 | 0.094 |  |
| KH103 | 0.005 | 0.007 | 0.004 | 0.018 | ← Soybean |
| KH104 | 0.091 | 0.052 | 0.003 | 0.051 |  |
| KH105 | 0.049 | 0.046 | 0.002 | 0.064 |  |
| KH106 | 0.029 | 0.028 | 0.001 | 0.021 |  |
| KH107 | 0.001 | 0.003 | 0.001 | 0.017 |  |
| KH108 | 0.000 | 0.002 | 0.001 | 0.014 |  |
| 3 KH109 | 0.025 | 0.030 | 0.004 | 0.207 | ← White Wine |
| 2 KH110 | 0.034 | 0.150 | 0.037 | 1.684 | ← Red wine |
| 4 KH111 | 0.015 | 0.009 | 0.010 | 1.865 |  |
| KH112 | 0.000 | 0.006 | 0.003 | 0.017 | Young soy Edamame |
| KH113 | 0.001 | 0.012 | 0.001 | 0.021 |  |
| KH114 | 0.002 | 0.008 | 0.002 | 0.232 |  |
| KH115 | 0.005 | 0.054 | 0.003 | 0.053 |  |
| KH116 | 0.001 | 0.012 | 0.001 | 0.027 |  |
| KH117 | 0.000 | 0.010 | 0.001 | 0.066 |  |
| KH118 | 0.008 | 0.031 | 0.004 | 0.102 |  |
| KH119 | 0.004 | 0.035 | 0.002 | 0.011 |  |
| KH120 | 0.000 | 0.021 | 0.003 | 0.031 |  |
| KH121 | 0.000 | 0.007 | 0.002 | 0.019 |  |
| KH122 | 0.000 | 0.008 | 0.001 | 0.003 |  |
| KH123 | 0.002 | 0.016 | 0.003 | 0.104 |  |
| KH124 | 0.012 | 0.024 | 0.002 | 0.016 |  |
| KH125 | 0.000 | 0.002 | 0.001 | 0.002 |  |
| KH126 | 0.000 | 0.002 | 0.001 | 0.001 |  |
| KH127 | 0.002 | 0.014 | 0.002 | 0.113 |  |
| KH128 | 0.003 | 0.006 | 0.001 | 0.014 |  |
| KH129 | 0.001 | 0.005 | 0.001 | 0.006 |  |
| KH130 | 0.004 | 0.054 | 0.002 | 0.015 |  |
| KH131 | 0.013 | 0.014 | 0.001 | 0.031 |  |
| 1 KH132 | 0.005 | 0.007 | 0.002 | 2.928 | ← Hot pepper |
| KH133 | 0.013 | 0.012 | 0.002 | 0.029 |  |
| KH134 | 0.003 | 0.005 | 0.002 | 0.054 |  |
| KH201 | 0.002 | 0.002 | 0.003 | 0.027 |  |
| KH202 | 0.000 | 0.003 | 0.002 | 0.017 |  |
| KH203 | 0.000 | 0.002 | 0.002 | 0.003 |  |
| KH204 | 0.000 | 0.003 | 0.001 | 0.187 |  |
| KH205 | 0.000 | 0.002 | 0.001 | 0.006 |  |
| KH206 | 0.000 | 0.002 | 0.001 | 0.007 |  |
| KH207 | 0.000 | 0.003 | 0.003 | 0.023 |  |
| KH208 | 0.002 | 0.002 | 0.002 | 0.046 |  |
| KH209 | 0.003 | 0.004 | 0.002 | 0.007 |  |
| KH210 | 0.063 | 0.003 | 0.034 | 0.752 |  |
| KH211 | 0.000 | 0.002 | 0.001 | 0.002 |  |
| KH212 | 0.000 | 0.002 | 0.002 | 0.012 |  |
| KH213 | 0.000 | 0.002 | 0.002 | 0.016 |  |
| KH214 | 0.004 | 0.003 | 0.002 | 0.118 |  |
| KH215 | 0.003 | 0.004 | 0.003 | 0.258 |  |
| KH216 | 0.003 | 0.006 | 0.003 | 0.318 |  |
| KH217 | 0.003 | 0.006 | 0.003 | 0.223 |  |
| KH301 | 0.002 | 0.018 | 0.003 | 0.079 |  |
| KH302 | 0.000 | 0.005 | 0.002 | 0.286 |  |
| KH303 | 0.000 | 0.005 | 0.002 | 0.264 |  |
| KH304 | 0.036 | 0.014 | 0.007 | 0.301 |  |
| KH305 | 0.034 | 0.015 | 0.007 | 0.302 |  |
| KH306 | 0.036 | 0.014 | 0.009 | 0.297 |  |
| KH307 | 0.037 | 0.016 | 0.008 | 0.296 |  |
| KH308 | 0.039 | 0.015 | 0.008 | 0.289 |  |
| KH309 | 0.001 | 0.004 | 0.002 | 0.120 |  |

Cell count in Kieu Hoang Afcc R Wine
Tenno budo is 5,000,000,000 /mL

Figure 22

KIEU HOANG™ AFCC™ WINE INHIBITS
THE GROWTH OF CANCER CELLS

KIEU HOANG™ AFCC™ WINE INHIBITS THE GROWTH OF LUNG
CANCER CELL.

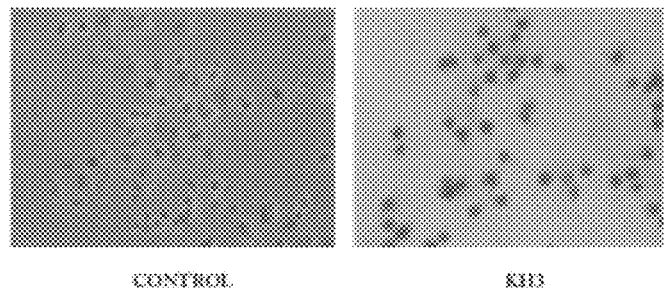

CONTROL                    KH3

KIEU HOANG™ AFCC™ WINE INHIBITS THE GROWTH OF BREAST
CANCER CELL.

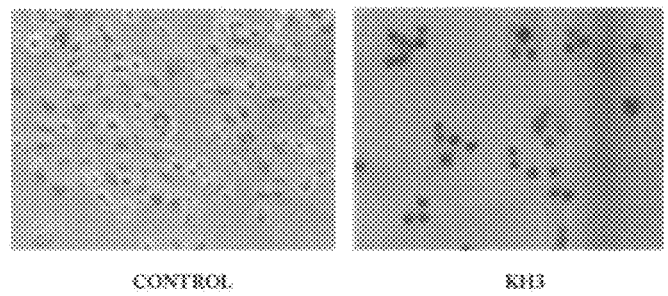

CONTROL                    KH3

NOTE: The number of cancer cells mixed with Kieu Hoang ™ red label wine has been reduced significantly as these cancer cells have turned into KH non-cancer good-healthy cells (PATENT NUMBER : 6199364)

Figure 23
KIEU HOANG™ AFCC™ WINE INHIBITS THE GROWTH OF CANCER CELLS
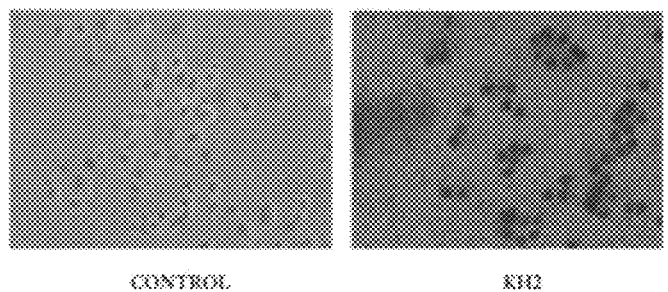
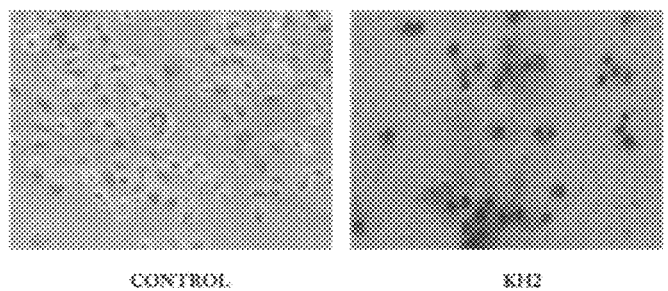

Figure 24

KIEU HOANG™ AFCC™ WINE INHIBITS THE GROWTH OF CANCER CELLS

KIEU HOANG™ AFCC™ WINE INHIBITS THE GROWTH OF LUNG CANCER CELL.

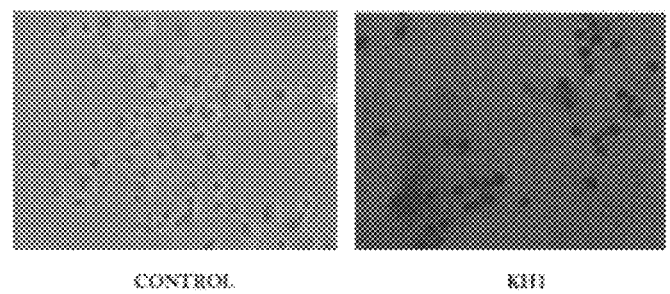

CONTROL          KH

KIEU HOANG™ AFCC™ WINE INHIBITS THE GROWTH OF BREAST CANCER CELL.

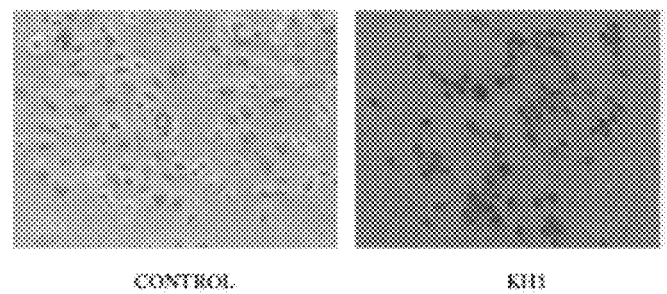

CONTROL          KH

Note: The number of cancer cells mixed with Kieu Hoang ™ blue label wine has been reduced significantly as these cancer cells have turned into KH non-cancer good healthy cells (PATENT NUMBER : 8993634)

Figure 39
A
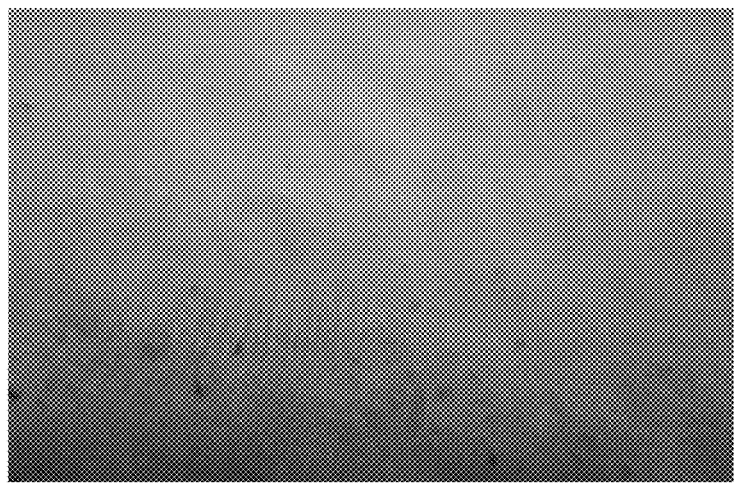
B
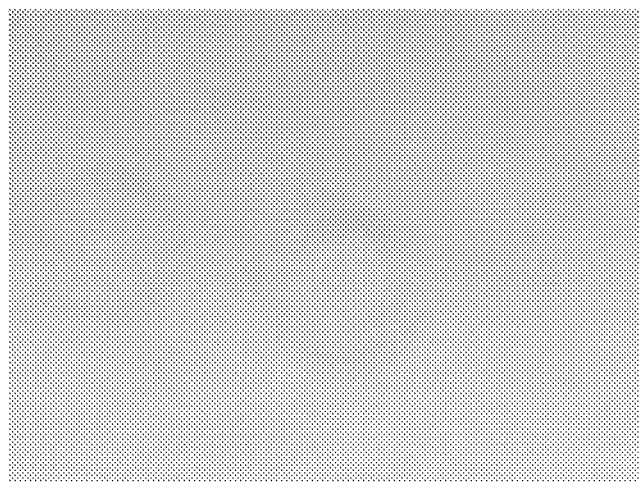
C
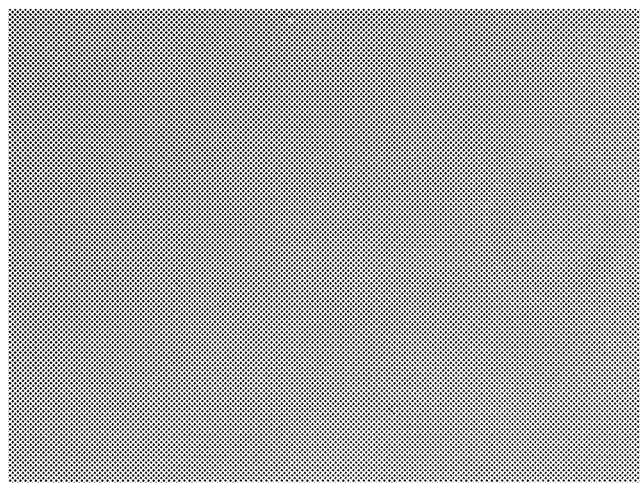

Figure 44
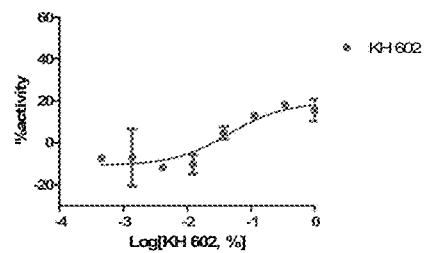
Figure 45
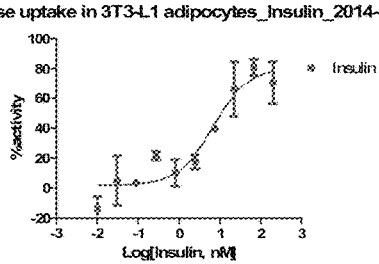 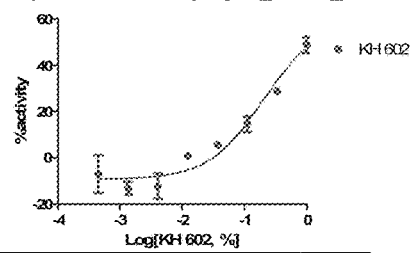

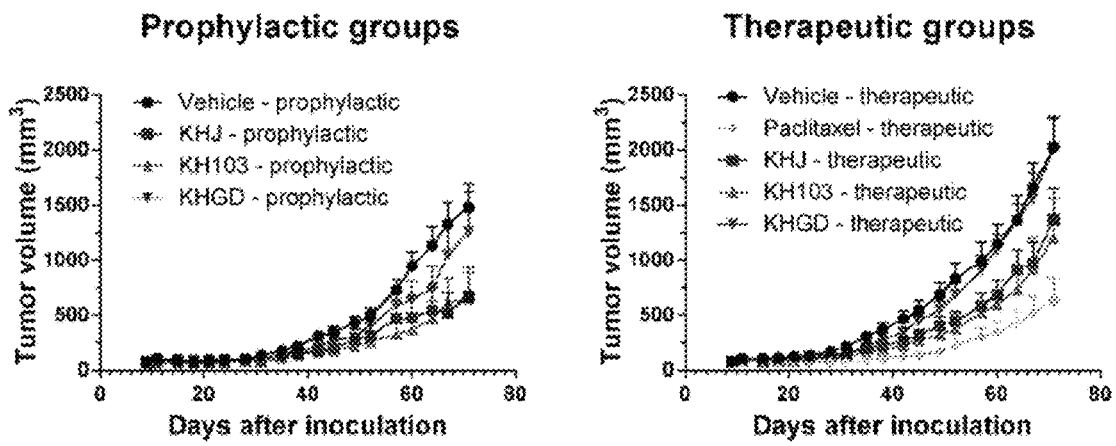
FIG. 55A-B
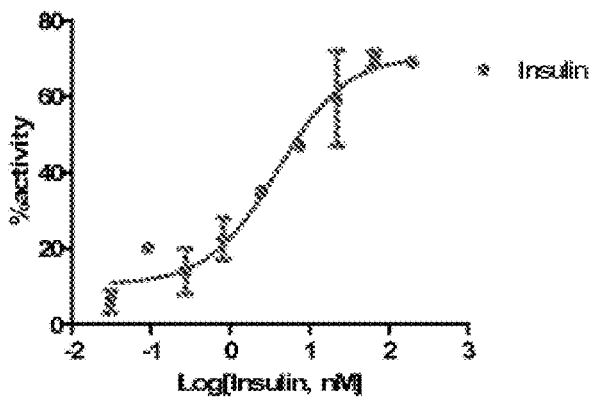
FIG. 56A

Glucose uptake in 3T3-L1 adipocyytes_KHJ_2014-8-27

| | KHJ |
|---|---|
| Log(agonist) vs. response - Variable slope | |
| Best-fit values | |
| BOTTOM | -3.341 |
| TOP | 67.32 |
| LOGESC50 | -0.08196 |
| HILLSLOPE | =1.000 |
| EC50 | 0.8280 |

Glucose uptake in 3T3-L1 adipocyytes_KH103_2014-8-27

| | KH 103 |
|---|---|
| Log(agonist) vs. response - Variable slope | |
| Best-fit values | |
| BOTTOM | |
| TOP | |
| LOGESC50 | |
| HILLSLOPE | |
| EC50 | |

METHODS OF TREATING DISEASES USING GRAPE PROTEINS

This application is a continuation of PCT/US16/53258, filed Sep. 23, 2016, which claims the benefit of U.S. Provisional Patent Application No. 62/222,317, filed Sep. 23, 2015, each of which is incorporated herein by reference.

TECHNICAL FIELD

The present subject matter relates to a process for producing wine from a grape bunch and further relates to a process for obtaining wine suitable for human consumption from the grape plant, wherein the complete grape bunch is ground and used to make wine. The present subject matter provides a process for obtaining wine from the grape bunch, wherein the skin, seed, flesh and stem are all ground to make wine.

The present subject matter relates to a process for producing beverages on the basis of juice and powder from the pomace and further relates to a process for obtaining fresh juice and powder suitable for human consumption from the pomace plant, wherein the complete pomace is grinded and used to make juice and powder. The present subject matter provides a process for obtaining juice and powder from the pomace, wherein the skin, seed, flesh, and stem of the grape in the pomace are all grinded and centrifuged to make juice and powder.

The present subject matter relates to a process for producing beverages on the basis of juice and powder from the grape bunch and further relates to a process for obtaining fresh juice and powder suitable for human consumption from the grape plant, wherein the complete grape bunch is ground and used to make juice and powder. The present subject matter provides a process for obtaining juice and powder from the grape bunch, wherein the skin, seed, flesh, and stem are all ground and centrifuged to make juice and powder.

The present subject matter relates to methods for treating various diseases in a patient, by administering a plurality of grape ingredients to a patient in need thereof. These methods involve administering various grape ingredients, for example, KH grape protein, to achieve a desired effect in the patient.

BACKGROUND

A grape has 5000 more genes than a human being. Grapes are a popular food staple and have ingredients which are healthy for humans. Wines are popular drinks, with ingredients healthy for humans.

There are presently many wine producers, but these companies create much waste during the production process. In fact, the waste parts of wine processing, such as waste pertaining to the grape skin, stem, or seed, are also useful. The present subject matter describes a process of obtaining wine from a whole grape bunch.

Similarly, pomace is commonly wasted during the production and processing of wine and juice. In fact, the parts of pomace such as skin, stem, or seed are also useful. The present subject matter describes a process of obtaining juice and powder from whole pomace.

Further, there are many grape juice and extraction factories, but the companies create much waste during the production process. In fact, the wasted parts of grapes, such as skin, stem, or seed, are also useful. The present subject matter describes a process of obtaining juice and powder from a whole grape bunch with only minor waste, as well as various methods of using such products.

SUMMARY

In one embodiment, the present subject matter relates to a food composition for human consumption comprising a plurality of grape ingredients, wherein the plurality of grape ingredients comprises ground flesh, seed, stem, and skin from grapes, and wherein the plurality of grape ingredients further comprise a wine comprising one or more KH grape proteins.

In this regard, the present subject matter further relates to a method of treating certain diseases in a patient comprising administering a food composition for human consumption to a patient in need thereof, the composition comprising a plurality of grape ingredients, wherein the plurality of grape ingredients comprise ground flesh, seed, stem, and skin from grapes, wherein the plurality of grape ingredients further comprise a wine comprising one or more KH grape proteins such that the composition has a concentration of KH grape protein above 0%. In one embodiment in this regard, KH Wine healthy cells from the KH grape proteins, after administration to the patient, send signals to damaged or sick cells, thereby triggering synthesis of proteins to transform the damaged or sick cells to become healthy, wherein the KH Wine healthy cells send signals to other undamaged cells to synthesize proteins to protect the other undamaged cells from damage, infection, and from being prone to DNA and other cellular alterations, and wherein the KH Wine healthy cells send signals to the patient's body to produce new cells that are healthy, thereby preventing the new cells from being affected by intracellular and extracellular damaging signals.

In a further embodiment, the present subject relates to a food composition for human consumption comprising a plurality of pomace ingredients, wherein the plurality of pomace ingredients comprises ground flesh, seed, stem, and skin from pomace in grapes, and wherein the plurality of pomace ingredients further comprise one or more KH Pomace proteins.

In this regard, the present subject natter further relates to a method of treating certain diseases in a patient comprising administering a food composition for human consumption to a patient in need thereof, the composition comprising a plurality of pomace ingredients, wherein the plurality of pomace ingredients comprise ground flesh, seed, stem, and skin from pomace in grapes, wherein the plurality of pomace ingredients further comprise one or more KH Pomace proteins such that the composition has a concentration of KH pomace proteins above 0%. In one embodiment in this regard, KH Pomace healthy cells from the KH Pomace proteins, after administration to the patient, send signals to damaged or sick cells, thereby triggering synthesis of proteins to transform the damaged or sick cells to become healthy, wherein the KH Pomace healthy cells send signals to other undamaged cells to synthesize proteins to protect the other undamaged cells from damage, infection, and from being prone to DNA and other cellular alterations, and wherein the KH Pomace healthy cells send signals to the patient's body to produce new cells that are healthy, thereby preventing the new cells from being affected by intracellular and extracellular damaging signals.

In another embodiment, the present subject matter relates to a food composition for human consumption comprising a plurality of grape ingredients, wherein the plurality of grape ingredients comprises ground flesh, seed, stem, and skin from grapes, and wherein the plurality of grape ingredients further comprise one or more KH Grape proteins.

In this regard, the present subject matter further relates to a method of treating certain diseases in a patient comprising administering a food composition for human consumption to a patient in need thereof, the composition comprising a plurality of grape ingredients, wherein the plurality of grape ingredients comprise ground flesh, seed, stem, and skin from grapes, wherein the plurality of grape ingredients further comprise one or more KH Grape proteins such that the composition has a concentration of KH Grape protein above 0%. In one embodiment in this regard, KH Grape healthy cells from the KH Grape proteins, after administration to the patient, send signals to damaged or sick cells, thereby triggering synthesis of proteins to transform the damaged or sick cells to become healthy, wherein the KH Grape healthy cells send signals to other undamaged cells to synthesize proteins to protect the other undamaged cells from damage, infection, and from being prone to DNA and other cellular alterations, and wherein the KH Grape healthy cells send signals to the patient's body to produce new cells that are healthy, thereby preventing the new cells from being affected by intracellular and extracellular damaging signals.

BRIEF DESCRIPTION OF THE DRAWINGS

FIG. 2 is a chart of wine tested items.
FIG. 22 shows the inhibition of KIEU HOANG™ Red label in lung and breast cancer.
FIG. 23 shows the inhibition of KIEU HOANG™ Green label in lung and breast cancer.
FIG. 24 shows the inhibition of KIEU HOANG™ Blue label in lung and breast cancer.
FIG. 39 shows cells from the inventor (A), from KH103 (B) and from Porcine TB (C).
FIG. 44 shows a graph depicting how KH602 an element in KUNAMIN™, helped to generate insulin for glucose uptakes in Diabetics on Jul. 14, 2014.
FIG. 45 shows a graph depicting KH602 Glucose uptake on Aug. 28, 2014 vs insulin.

FIG. 55A-B show plots depicting tumor volume trace after administering KHJ, KH103, or KHGD to female BALB/c nude mice bearing MDA-MB-436 established tumors. Data points represent group mean, error bars represent standard error of the mean (SEM).

FIG. 56A-E show dose response curve fits for glucose uptake in 3T3-L1 adipocytes for insulin, KHG, KHB, KHJ, and KH103.

DETAILED DESCRIPTION

Unless defined otherwise all technical and scientific terms used herein have the same meaning as commonly understood to one of ordinary skill in the art to which the presently described subject matter pertains.

In addition, as used herein, the phrases "KH Wine protein" and "KH grape protein" are considered to be interchangeable and to refer to the same proteins.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

I. Process of Making Wine from a Whole Grape Bunch

An embodiment of the present subject matter is directed to a food composition for human consumption comprising a plurality of grape ingredients, wherein the plurality of grape ingredients comprises ground flesh, seed, stem, and skin from grapes, and wherein the plurality of grape ingredients further comprise one or more KH grape proteins.

Figure 1:
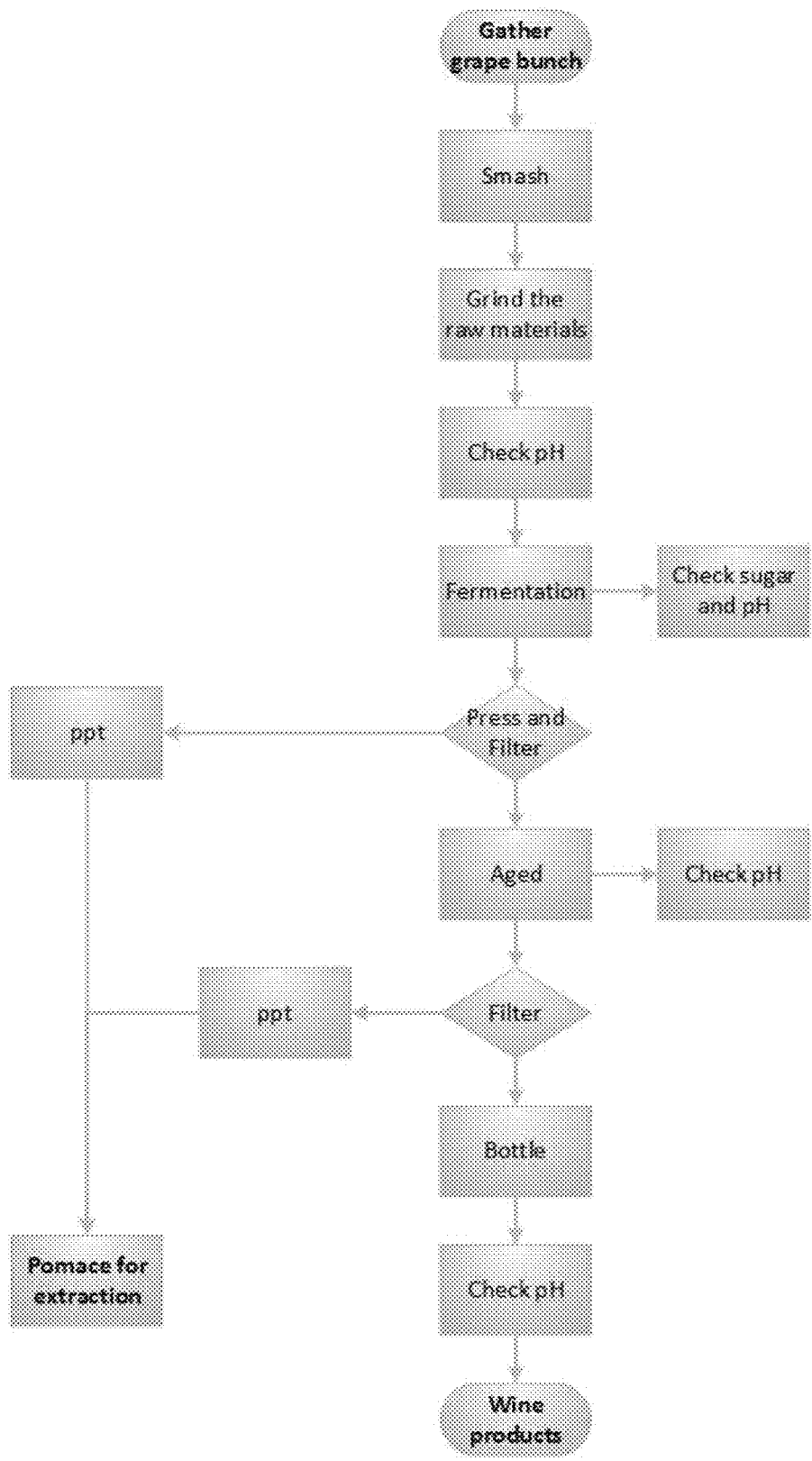
FIG. 1 is a flow chart.

In this regard, the present subject matter describes a method for the production of wine from the grape plant (FIG. 1). The grape bunch is treated immediately after harvest. The whole grape bunch is smashed in a grinder to cut the thick stem at about 20-30° C. All of the raw materials are collected and ground in a superfine mill at about 20-30° C. The raw juice is collected, and the pH of the raw juice is checked, which should be about 3.4-8.0. The raw juice is fermented at about 23-24° C. The pH and sugar are checked during fermentation. The wine is pressed and filtered at room temperature. The precipitate is collected and the wine is transferred.

The wine is aged at about 15-20° C. and the pH is checked during the aging. The wine is filtered at about 15-20° C. The precipitate is collected and the wine in transferred. The wine is bottled and the pH is checked. All of the precipitate is collected for extraction use.

In an embodiment, the wine is spray dryed to create a powder. In an embodiment, a combination of pasteurization and low pH is used for bacterial and viral inactivation. In an embodiment, temperature during manufacturing of the food composition is −10-250° C. In an embodiment, pH during the process is 2.5-10.

In an embodiment, the food composition is KIEU HOANG™ wine containing from a few hundred thousand living cells per ml up to a maximum 5 to 6 billion cells per ml. In an embodiment, the food composition is wine CALIW containing from 500,000-1,000,000 cells per ml. In an embodiment, the food composition is Blue Label wine containing from 10,000,000-50,000,000 cells per ml. In an embodiment, the food composition is Green Label wine containing from 100,000,000 up to 300,000,000 cells per ml. In an embodiment, the food composition is Red Label wine containing from 300,000,000-1,000,000,000 cells per ml. In an embodiment, the food composition is Yellow Label wine containing from 1,100,000,000-2,000,000,000 cells per ml. In an embodiment, the food composition is Pellow Label or Kieu Hoang Proprietary Red Blend wine containing from 2,100,000,000-3,000,000,000 cells per ml. In an embodiment, the food composition is Kogo and Tenno BUDO wine containing from 3,100,000,000-5,000,000,000 cells per ml.

In an embodiment, the composition comprises APOA1 (High Density Lipoprotein) from said KH grape protein having a molecular weight similar to Human APOA1 (High Density Lipoprotein).

II. Process of Making Pomace Juice and Powder

An embodiment of the present subject matter is directed to a food composition for human consumption comprising a plurality of pomace ingredients, wherein the plurality of pomace ingredients comprise ground flesh, seed, stem, and skin from pomace in grapes, and wherein the plurality of pomace ingredients further comprise one or more KH Pomace proteins.

In an embodiment, the present subject matter describes a method for the production of juice and powder from the pomace plant. The pomace is treated immediately after harvest. The fresh pomace is washed in a cleaning bath at about 0-100° C. The whole pomace is smashed in a grinder to cut the thick stem at about 0-100° C. The raw materials are collected and ground in a superfine mill at about 0-100° C. The raw juice is collected. The pH of the raw juice is checked and should be about 2.5-10. The raw juice is centrifuged at low to high rpm with a normal centrifuge at about −30-30° C. The precipitate and supernatant are collected.

Water at two to four times the volume is added to the precipitate and mixed about 10-100 minutes and centrifuged again at low to high rpm with normal centrifuge at about −30-60° C. The precipitate and supernatant are collected.

Water at one to two times the volume is added, then mixed about 10-100 minutes and centrifuged again at low to high rpm with normal centrifuge at about −30-60° C. The precipitate and supernatant are collected. All the supernatant is mixed for 10-100 minutes at about 0-100° C. The pH of the supernatant is checked and should be about 2.5-10. The supernatant juice is centrifuged at moderate to high rpm with a disc centrifuge at about −30-60° C., and the juice is collected. The juice pH is checked and should be about 2.5-10.

In an embodiment, to make juice product, the collected juice is homogenized at 40-60 MPa. The juice is sterilized at 130-140° C. for 5-20 seconds with a pipe sterilizer. The clear juice is bottled at 25-35° C. The pH of the juice is checked.

In an embodiment, to make a powder product, the collected juice is concentrated in a single-effect falling film evaporator at 65-85° C. until the brix value is 30-50. The concentrated juice is transferred to the centrifugal spray dryer to produce powder.

All precipitate is mixed and capsulized.

In an embodiment, the food composition is a powder, juice, food supplement, or mixed beverage. In an embodiment, the food composition is used in anti-aging cosmetics. In an embodiment, the temperature during manufacturing is −10-250° C. In an embodiment, the pH is 2.5-10. In an embodiment, a combination of pasteurization and dry high temperature heating is used for bacterial and viral inactivation.

In an embodiment, the food composition comprises APOA1 (High Density Lipoprotein) from said KH Pomace proteins having a molecular weight similar to Human APOA1 (High Density Lipoprotein). In an embodiment, the food composition comprises Albumin from said KH Pomace proteins having a molecular weight similar to Human Albumin. In an embodiment, the food composition comprises Alpha 1 Antitrypsin from said KH Pomace proteins having a molecular weight similar to Human Alpha 1 Antitrypsin.

In an embodiment, the KH Pomace protein is KH602. In an embodiment, KH601 and KH602 have the molecular lower band of human immunoglobulin.

III. Method of Producing Beverages on the Basis of Juice and Powder from the Grape Bunch An embodiment of the present subject matter is directed to a food composition for human consumption comprising a plurality of grape ingredients, wherein the plurality of grape ingredients comprises ground flesh, seed, stem, and skin from grapes, and wherein the plurality of pomace ingredients further comprise one or more KH Grape proteins.

In an embodiment, the food composition is a powder, juice, food supplement, or mixed beverage. In an embodiment, the temperature during manufacturing is −10-250° C. In an embodiment, the pH is 2.5-10. In an embodiment, a combination of pasteurization and dry high temperature heating is used for bacterial and viral inactivation.

In an embodiment, the food composition comprises APOA1 (High Density Lipoprotein) from said KH Grape proteins having a molecular weight similar to Human APOA1 (High Density Lipoprotein). In an embodiment, the food composition comprises Albumin from said KH Grape proteins having a molecular weight similar to Human Albumin. In an embodiment, the food composition comprises Alpha 1 Antitrypsin from said KH Grape proteins having a molecular weight similar to Human Alpha 1 Antitrypsin. In an embodiment, the food composition comprises immunoglobulin and APOA-1 from said KH Grape proteins having a molecular weight similar to Human immunoglobulin and APOA-1.

In an embodiment, the KH Grape protein is KH602. In an embodiment, the KH Grape protein is KHJ.

Figure 40:
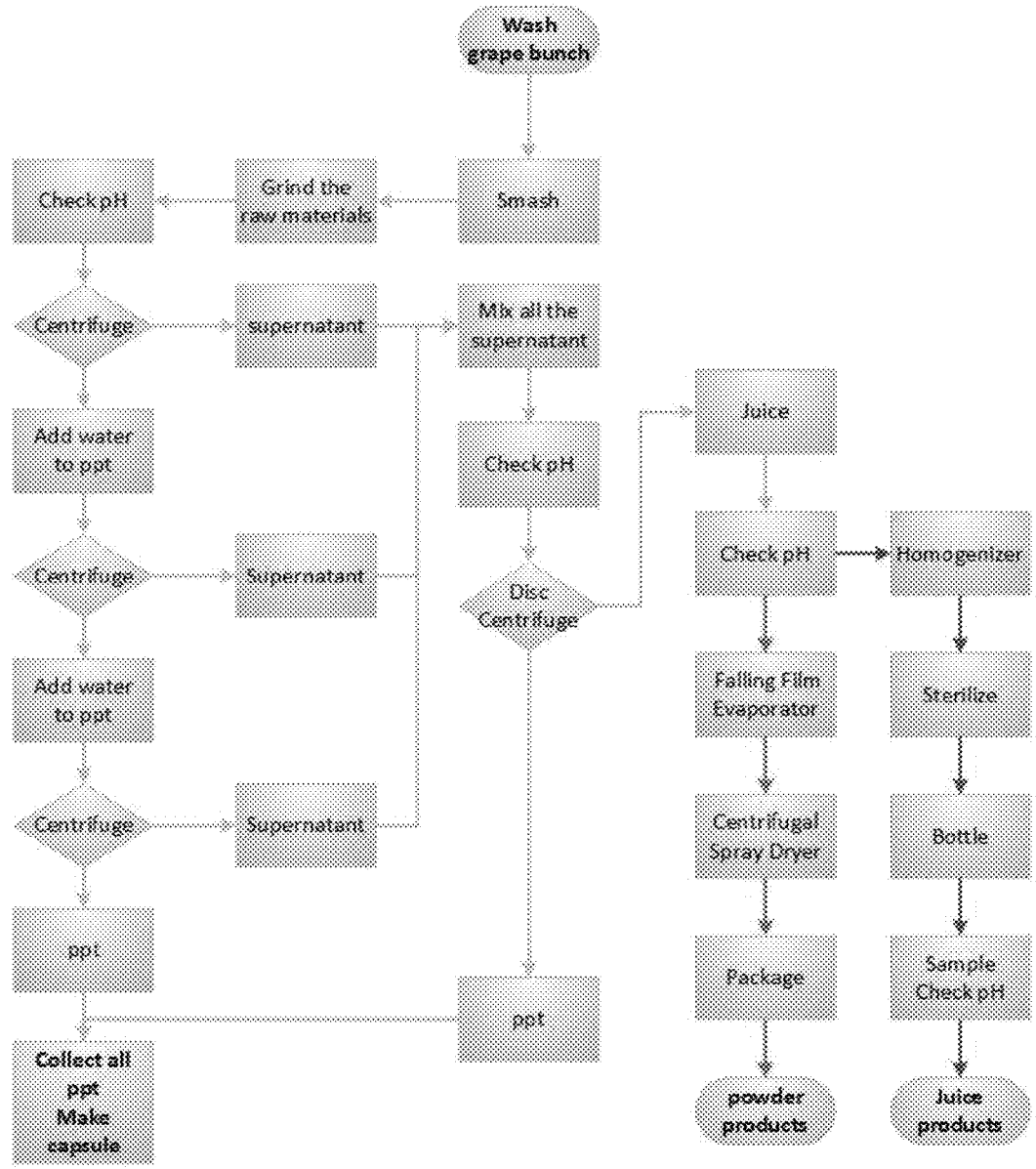
FIG. 40 shows a grape process flow chart.

In an embodiment, the present subject matter describes a method for the production of juice and powder from the grape plant (FIG. 40). The grape bunch is treated immediately after harvest. The fresh grape bunch is washed in a cleaning bath at about 0-100° C. The whole grape bunch is smashed in a grinder to cut the thick stem at about 0-100° C. All of the raw materials are collected and ground in a superfine mill at about 0-100° C. The raw juice is collected, and the pH of the raw juice is checked, which should be about 2.5-10. The raw juice is centrifuged at low to high rpm with normal centrifuge at about −30-30° C. The precipitate and supernatant are collected.

Water at two to four times the volume is added to the precipitate and mixed about 10-100 minutes and centrifuged again at low to high rpm with normal centrifuge at about −30-60° C. The precipitate and supernatant are collected.

Water at one to two times the volume is added, then mixed about 10-100 minutes and centrifuged again at low to high rpm with normal centrifuge at about −30-60° C. The precipitate and supernatant are collected. All the supernatant is mixed for 10-100 minutes at about 0-100° C. The pH of the supernatant is checked and should be about 2.5 to 10. The supernatant juice is centrifuged at moderate to high rpm with a disc centrifuge at about −30-60° C., and the juice is collected. The juice pH is checked and should be about 2.5-10.

In an embodiment, to make a juice product, the collected juice is homogenized at 40-60 MPa. The juice is sterilized at 130-140° C. for 5-20 seconds with a pipe sterilizer. The clear juice is bottled at 25-35° C. The pH of the juice is checked.

In an embodiment, to make a powder product, the collected juice is concentrated in a single-effect falling film evaporator at 65–85° C. until the brix value is 30-50. The concentrated juice is transferred to the centrifugal spray dryer to produce powder.

All precipitate is mixed and capsulized.

In an embodiment, the food composition of the present subject matter is a powder, juice or other beverage, food supplement, or concentrate. In an embodiment, the food composition of the present subject matter is a beverage and the KHJ protein comprises KH103 protein. In an embodiment, the KH Grape protein comprises KHJ protein. In an embodiment, the KHJ protein comprises proteins having a molecular weight similar to molecular weights of human immunoglobulin and APOA-1 proteins. In an embodiment, the KHJ protein further comprises living cells. In an embodiment, the KH Grape protein comprises KH602 protein. In an embodiment, the KH Grape protein comprises a combination of KH103 protein and KHJ protein and may be in liquid or powder form.

IV. Methods of Treatment/Prevention

An embodiment of the present subject matter is directed to a method of treating certain diseases in a patient comprising administering the food composition to a patient in need thereof, wherein the food composition has a concentration of KH Wine protein above 0%.

Another embodiment of the present subject matter is directed to a method of treating certain diseases in a patient comprising administering the food composition to a patient in need thereof, wherein the food composition has a concentration of KH Pomace proteins above 0%.

A further embodiment of the present subject matter is directed to a method of treating certain diseases in a patient comprising administering the food composition to a patient in need thereof, wherein the food composition has a concentration of KH Grape proteins above 0%.

In an embodiment, administration of the food composition lowers triglycerides and cholesterol and increases High Density Lipoprotein (APOA1) in the patient. In an embodiment, administration of the food composition increases glucose uptake in the patient. In an embodiment, administration of the food composition cleans plaque and provides heart, brain, and artery blockage protection in the patient. In another embodiment, administration of the food composition treats and/or prevents diabetes in a patient. In a still further embodiment, administration of the food compositions treats and/or prevents hypercholesterolemia and/or hyperlipidemia in a patient.

In an embodiment, administration of the food composition inhibits growth of various cancer cells in the patient. Exemplary in this regard, the food composition described herein inhibits growth of leukemia cells in a patient, treats leukemia in a patient, and/or prevents leukemia in a patient. In an embodiment, administration of the food composition prevents the development of leukemia in mice after two times of implantation with a total of 30,000,000 Leukemia cancer cells through vein injection (first time with 10,000,000 cells and second time with 20,000,000 cells for those mice that did not develop leukemia after the first implantation). Similarly, the food composition described herein inhibits the growth of breast and/or lung cancer cells in a patient, treats breast and/or lung cancer in a patient, and/or prevents breast and/or lung cancer in a patient.

In an embodiment, administration of the food composition suppresses inflammation in the patient due to different causes of disease.

In an embodiment, the present subject matter is directed to a method of treating a certain disease in a patient comprising administering the food composition to a patient in need thereof, wherein the food composition has a concentration of KH Grape protein above 0%. In an embodiment, the certain disease is cancer and the administration inhibits growth of cancer cells. In an embodiment, the certain disease is leukemia and the cancer cells comprise leukemia cancer cells. In an embodiment, administering the food composition is intended to prolong the patient's life by preventing leukemia development. In an embodiment, KH Grape healthy cells, formed after administration of the KH Grape proteins to a patient, signal to damaged or sick cells, thereby triggering synthesis of proteins by RNA to transform the damaged or sick cells to become healthy, wherein the healthy cells send signals to other undamaged cells to synthesize proteins to protect the other undamaged cells from damage, infection, and from being prone to DNA and other cellular alterations. Further, the KH Grape healthy cells after administration to a patient send signals to the patient's body to produce new cells that are healthy, thereby preventing the new cells from being affected by intracellular and extracellular damaging signals.

In an embodiment, the present subject matter is directed to a method of treating high blood glucose levels in a patient in need thereof comprising administering the food composition to a patient in need thereof, wherein the food composition has a concentration of KH Grape protein above 0%. The KH Grape protein may comprise KHGD protein.

In an embodiment, the present subject matter is directed to a method of treating insulin sensibility in a patient in need thereof comprising administering the food composition to a patient in need thereof, wherein the food composition has a concentration of KH Grape protein above 0%. The KH Grape protein may comprise KHGD protein.

In an embodiment, the present subject matter is directed to a method of treating plasma TG levels in a patient in need thereof comprising administering the food composition to a patient in need thereof, wherein the food composition has a concentration of KH Grape protein above 0%. The KH Grape protein may be selected from the group consisting of KH103 protein, KHJ protein, KHGD protein, and combinations thereof.

In an embodiment, the present subject matter is directed to a food composition for human consumption comprising a plurality of ingredients, all from grape, such as the flesh, seed, stem, and skin from grape.

In an embodiment, the present subject matter is directed to juice and a mixed beverage under the trademark KUNAMIN™.

In an embodiment, the present subject matter is directed to powder and a mixed food supplement.

In an embodiment, the present subject matter is directed to a KHJ formulation having the ability to inhibit the growth of various cancer cells in vitro. Further, this formulation is able to prolong the life and to prevent the development of leukemia in mice after two times of implantation with a total of 30,000,000 Leukemia cancer cells through vein injection (first time with 10,000,000 cells and the second time with 20,000,000 cells for those mice that did not develop leukemia after first implantation).

In an embodiment, the present subject matter is directed to a KH602 formulation having the ability to inhibit the growth of various cancer cells in vitro. Further, this formulation is able to prolong the life and to prevent the development of leukemia in mice after two times of implantation with a total of 30,000,000 leukemia cancer cells through vein injection (first time with 10,000,000 cells and the second time with 20,000,000 cells for those mice that did not develop leukemia after first implantation).

In an embodiment, the present subject matter is directed to KHJ having KH Grape good healthy cells in which the RNA synthesizes good proteins that: send signals to the damaged, sick, and bad cells that triggers that synthesis of good proteins that transform these cells to become good healthy cells; send signals to the other currently undamaged cells to synthesis of good proteins to protect them from being damaged, infected and prone to DNA and other cellular alterations; send signal to the body to produce new cells that are healthy and forbid them from being affected by intra- and extracellular damaging signals.

In an embodiment, the present subject matter is directed to KH602 having KH Grape good healthy cells in which the RNA synthesizes good proteins that: send signals to the damaged, sick, and bad cells that triggers that synthesis of good proteins that transform these cells to become good healthy cells; send signals to the other currently undamaged cells to synthesis of good proteins to protect them from being damaged, infected and prone to DNA and other cellular alterations; send signal to the body to produce new cells that are healthy and forbid them from being affected by intra- and extracellular damaging signals.

In an embodiment, the present subject matter is directed to a combination of KUNAKIN™ (KH103) and KUNAMIN™ (KHJ) to make KUNAKIMIN™ in liquid and/or powder and having the same effect and functions of all of the above.

In an embodiment, the present subject matter is directed to KHJ further comprising proteins having molecular weights similar to molecular weights of human proteins immunoglobulin and APOA-1.

In an embodiment, the present subject matter is directed to KUNAMIN™ (KHJ) further comprising living cells.

EXAMPLES

In Vitro Study 1—Lipid Panel

The highest level of HDL among 100 tested items was found in KIEU HOANG™ wine. FIG. 2 is a chart of wine tested items. KIEU HOANG™ wine red and white without specific number of cells in them were tested. The red wine KH110 contains the highest level of HDL with 0.180/uL. Tests were performed by one of the top ten CRO labs in the world.

The objective of this study was to quantify Cholesterol/Cholesteryl Ester (TC), HDL Cholesterol (HDLC), LDL/VLDL Cholesterol (LDLC/VLDLC), and Triglyceride (TG) concentration in RAAS products.

The Cholesterol/Cholesteryl Ester Quantitation Kit provides a simple method for sensitive quantification of free cholesterol, cholesteryl esters, or both by colorimetric or fluorometric methods. The majority of the cholesterol in blood is in the form of cholesteryl esters which can be hydrolyzed to cholesterol by cholesterol esterase. Cholesterol is then oxidized by cholesterol oxidase to yield $H_2O_2$ which reacts with a sensitive cholesterol probe to produce color ($\lambda$max=570 nm) and fluorescence (Ex/Em=535/590 nm). The assay detects total cholesterol (cholesterol and cholesteryl esters) in the presence of cholesterol esterase or free cholesterol in the absence of cholesterol esterase in the reaction.

BioVision's HDL and LDL/VLDL Cholesterol Quantification Kit provides a simple quantification method of HDL and LDL/VLDL after a convenient separation of HDL from LDL and VLDL (very low-density lipoprotein) in serum samples. In the assay, cholesterol oxidase specifically recognizes free cholesterol and produces products which react with probe to generate color ($\lambda$=570 nm) and fluorescence (Ex/Em=538/587 nm). Cholesterol esterase hydrolizes cholesteryl ester into free cholesterol, therefore, cholesterol ester and free cholesterol can be detected separately in the presence and absence of cholesterol esterase in the reactions.

Likewise, the Triglyceride Quantification Kit provides a sensitive, easy assay to measure triglyceride concentration in variety of samples. In the assay, triglycerides are converted to free fatty acids and glycerol. The glycerol is then oxidized to generate a product which reacts with the probe to generate colorimetric (spectrophotometry at $\lambda$=570 nm) and fluorometric (Ex/Em=535/590 nm) methods. The kit can detect 1 pmol-10 nmol (or 1~10000 μM range) of triglyceride in various samples listed below in Table 1:

TABLE 1

|  | Volume | Sample | Storage |
| --- | --- | --- | --- |
| KH 101 | ~1 ml | use as supplied | −20° C. |
| KH 102 | ~1 ml | use as supplied | −20° C. |
| KH 103 | ~1 ml | use as supplied | −20° C. |
| KH 104 | ~1 ml | use as supplied | −20° C. |
| KH 105 | ~1 ml | use as supplied | −20° C. |
| KH 106 | ~1 ml | use as supplied | −20° C. |
| KH 107 | ~1 ml | use as supplied | −20° C. |
| KH 108 | ~1 ml | use as supplied | −20° C. |
| KH 109 | ~1 ml | use as supplied | −20° C. |
| KH 110 | ~1 ml | use as supplied | −20° C. |
| KH 111 | ~1 ml | use as supplied | −20° C. |
| KH 112 | ~1 ml | use as supplied | −20° C. |
| KH 113 | ~1 ml | use as supplied | −20° C. |
| KH 114 | ~1 ml | use as supplied | −20° C. |
| KH 115 | ~1 ml | use as supplied | −20° C. |
| KH 116 | ~1 ml | use as supplied | −20° C. |
| KH 117 | ~1 ml | use as supplied | −20° C. |
| KH 118 | ~1 ml | use as supplied | −20° C. |
| KH 119 | ~1 ml | use as supplied | −20° C. |
| KH 120 | ~1 ml | use as supplied | −20° C. |
| KH 121 | ~1 ml | use as supplied | −20° C. |
| KH 122 | ~1 ml | use as supplied | −20° C. |
| KH 123 | ~1 ml | use as supplied | −20° C. |
| KH 124 | ~1 ml | use as supplied | −20° C. |
| KH 125 | ~1 ml | use as supplied | −20° C. |
| KH 126 | ~1 ml | use as supplied | −20° C. |
| KH 127 | ~1 ml | use as supplied | −20° C. |
| KH 128 | ~1 ml | use as supplied | −20° C. |
| KH 129 | ~1 ml | use as supplied | −20° C. |
| KH 130 | ~1 ml | use as supplied | −20° C. |
| KH 131 | ~1 ml | use as supplied | −20° C. |
| KH 132 | ~1 ml | use as supplied | −20° C. |
| KH 133 | ~1 ml | use as supplied | −20° C. |
| KH 134 | ~1 ml | use as supplied | −20° C. |
| KH 201 | ~1 ml | use as supplied | −20° C. |

TABLE 1-continued

|  | Volume | Sample | Storage |
| --- | --- | --- | --- |
| KH 202 | ~1 ml | use as supplied | −20° C. |
| KH 203 | ~1 ml | use as supplied | −20° C. |
| KH 204 | ~1 ml | use as supplied | −20° C. |
| KH 205 | ~1 ml | use as supplied | −20° C. |
| KH 206 | ~1 ml | use as supplied | −20° C. |
| KH 208 | ~1 ml | use as supplied | −20° C. |
| KH 209 | ~1 ml | use as supplied | −20° C. |
| KH 210 | ~1 ml | use as supplied | −20° C. |
| KH 211 | ~1 ml | use as supplied | −20° C. |
| KH 212 | ~1 ml | use as supplied | −20° C. |
| KH 213 | ~1 ml | use as supplied | −20° C. |
| KH 214 | ~1 ml | use as supplied | −20° C. |
| KH 215 | ~1 ml | use as supplied | −20° C. |
| KH 216 | ~1 ml | use as supplied | −20° C. |
| KH 217 | ~1 ml | use as supplied | −20° C. |
| KH 301 | ~1 ml | use as supplied | −20° C. |
| KH 302 | ~1 ml | use as supplied | −20° C. |
| KH 303 | ~1 ml | use as supplied | −20° C. |
| KH 304 | ~1 ml | use as supplied | −20° C. |
| KH 305 | ~1 ml | use as supplied | −20° C. |
| KH 306 | ~1 ml | use as supplied | −20° C. |
| KH 307 | ~1 ml | use as supplied | −20° C. |
| KH 308 | ~1 ml | use as supplied | −20° C. |
| KH 309 | ~1 ml | use as supplied | −20° C. |

Total Cholesterol/Cholesteryl Ester Quantification by Fluorometric Method (TC)

Cholesterol/Cholesteryl Ester Quantitation Kit (Catalog #K603-100; 100 assays; Store at −20° C.).

The Kit Contents are as listed below in Table 2:

TABLE 2

| Components | K622-100 | Cap Code | Part Number |
| --- | --- | --- | --- |
| Cholesterol Assay Buffer | 25 ml | WM | K603-100-1 |
| Cholesterol Probe (in DMSO, anhydrous) | 200 µl | Red | K603-100-2A |
| Enzyme Mix (lyophilized) | 1 vial | Green | K603-100-4 |
| Cholesterol Esterase (lyophilized) | 1 vial | Blue | K603-100-5 |
| Cholesterol Standard (2 µg/µl) | 100 µl | Yellow | K603-100-6 |

Store kit at −20° C. and protect from light. Warm to room temperature before use. Keep enzymes and cholesterol standard on ice while using.

Warm the Cholesterol Probe to room temperature to thaw the DMSO solution before use. Store at −20° C., protect from light.

Dissolve the Cholesterol Esterase in 220 µl Cholesterol Assay Buffer before use. Aliquot and store at −20° C.

Dissolve the Enzyme Mix in 220 µl Cholesterol Assay Buffer before use. Aliquot and store at −20° C.

Standard Curve Preparation:

Dilute the Cholesterol Standard to 25 ng/µl by adding 10 µl of the Cholesterol Standard to 790 µl of Cholesterol Assay Buffer, mix well. Add 0, 4, 8, 12, 16, 20 µl into a series of wells. Adjust volume to 50 µl/well with Cholesterol Assay Buffer to generate 0, 0.1, 0.2, 0.3, 0.4, 0.5 µg/well of the Cholesterol Standard.

Sample Preparation:

Add 5 µl test samples in a 96-well clear bottom black plate, Adjust to the final volume of 50 µl/well with Cholesterol Assay Buffer.

Mix enough reagents for the number of samples and standards to be performed. For each well, prepare a total 50 µl Reaction Mix:

| 45.6 µl | Cholesterol Assay Buffer |
| 0.4 µl | Cholesterol Probe |
| 2 µl | Cholesterol Enzyme Mix |
| 2 µl | Cholesterol Esterase |

Mix well Add 50 µl of the Reaction Mix to each well containing standard or test samples.

Incubate the reaction for 60 minutes at 37° C., protect from light.

Measure fluorescence at Ex/Em 535/590 nm in ENSPIRE.

Calculations:

Subtract 0 standard reading from readings. Plot the standard curve. Apply the sample readings to the standard curve to determine sample cholesterol amount in the reaction well.

Sample Cholesterol Concentrations:

$$C = A/V \ (\mu g/\mu l)$$

Where: A is the sample cholesterol amount from the standard curve (µg).

V is original sample volume added to the sample reaction well (µl).

HDL and LDL/VLDL Cholesterol Quantification by Fluorometric Method (HDLC and LDLC/VLDLC)

HDL and LDL&VLDL Cholesterol Quantification Kit (Catalog #K613-100; 100 assays; Store at −20° C.). The Kit Contents are as follows in Table 3:

TABLE 3

| Components | Volume | Cap Code | Part No. |
| --- | --- | --- | --- |
| Cholesterol Assay Buffer | 25 ml | WM | K613-100-1 |
| 2X LDL/VLDL Precipitation Buffer | 10 ml | NM | K613-100-2 |
| Cholesterol Probe (in DMSO, anhydrous) | 200 µl | Red | K613-100-3A |
| Enzyme Mix (Lyophilized) | 1 vial | Green | K613-100-5 |
| Cholesterol Esterase (Lyophilized) | 1 vial | Blue | K613-100-6 |
| Cholesterol Standard (2 µg/µl) | 100 µl | Yellow | K613-100-7 |

Warm the Cholesterol Probe to room temperature, store at −20° C., protect from light.

Dissolve the Cholesterol Esterase in 220 µl Cholesterol Assay Buffer. Aliquot and store at −20° C.

Dissolve the Enzyme Mix in 220 µl Cholesterol Assay Buffer prior to use. Aliquot and store at −20° C.

Separation of HDL and LDL/VLDL:

Mix 100 µl of 2× Precipitation Buffer with 100 µl of serum sample in microcentrifuge tubes. Incubate 10 min at RT, centrifuge at 2000×g (5000 rpm) for 10 min. Transfer the supernatant (HDL) into new labeled tubes. Spin the precipitates (LDL/VLDL) again, Remove HDL supernatant. Resuspend the precipitate in 200 µl PBS.

Note A: If the supernatant is cloudy, the sample should be re-centrifuged. If the sample remains cloudy, dilute the sample 1:1 with PBS, and repeat the separation procedure. Multiply final results by two (2) due to the dilution with the 2× Precipitation Buffer.

Standard Curve and Sample Preparations:

Dilute the Cholesterol Standard to 25 ng/µl by adding 10 µl of the Cholesterol Standard to 790 µl of Cholesterol Assay Buffer, Add 0, 4, 8, 12, 16, 20 µl into a series of wells in a 96-well clear bottom black plate. Adjust volume to 50 µl/well with Cholesterol Assay Buffer to generate 0, 0.1, 0.2, 0.3, 0.4, 0.5 µg/well of the Cholesterol Standard. Use 5 µl of the HDL or LDL/VLDL fraction, adjust the total volume to 50 µl/well with Cholesterol Assay Buffer.

Mix enough reagents for the number of assays performed. For each assay, prepare a total 50 μl Reaction Mix containing:

| | |
|---|---|
| 45.6 μl | Cholesterol Assay Buffer |
| 0.4 μl | Cholesterol Probe |
| 2 μl | Enzyme Mix |
| 2 μl | Cholesterol Esterase |

Add 50 μl of the Reaction Mix to each well containing the Cholesterol Standard or test samples, mix well. Incubate the reaction for 60 minutes at 37° C., protect from light. Measure fluorescence at Ex/Em 538/587 nm in ENSPIRE.

Calculations:

Subtract 0 standard reading from readings. Plot the standard curve. Apply the sample readings to the standard curve to determine sample cholesterol amount in the reaction well. Sample Cholesterol Concentrations:

$$C = A/V \ (\mu g/\mu l)$$

Where: A is the sample cholesterol amount from the standard curve (μg).

V is original sample volume added to the sample reaction well (μl).

Triglyceride Quantification by Fluorometric Method (TG)

Triglyceride Quantification Kit (Catalog #K622-100; 100 assays; Store at −20° C.). The Kit Contents are as follows in Table 4:

TABLE 4

| Components | K622-100 | Cap Code | Part Number |
|---|---|---|---|
| Triglyceride Assay Buffer | 25 ml | WM | K622-100-1 |
| Triglyceride Probe (lyophilized) | 1 vial | Red | K622-100-2 |
| Dimethylsulfoxide (DMSO, Anhydrous) | 0.4 ml | Brown | K622-100-3 |
| Lipase | 0.5 ml | Blue | K622-100-4 |
| Triglyceride Enzyme Mix (lyophilized) | 1 vial | Green | K622-100-5 |
| Triglyceride Standard (1 mM) | 0.2 ml | Yellow | K622-100-6 |

Store kit at −20° C., protect from light. Warm Triglyceride Assay Buffer to room temperature before use. Briefly centrifuge all small vials prior to opening.

Dissolve the Triglyceride Probe in 220 μl anhydrous DMSO (provided) before use. Store at −20° C., protect from light and moisture.

Dissolve the Triglyceride Enzyme Mix in 220 μl Triglyceride Assay Buffer. Aliquot and store at −20° C.

Dissolve the Lipase in 220 μl Triglyceride Assay Buffer. Aliquot and store at −20° C.

Standard Curve Preparation:

Re-dissolve in hot water bath (80~100° C.) for 1 minute or until the standard looks cloudy, vortex for 30 seconds, repeat the heat and vortex one more time. Dilute the Triglyceride Standard to 0.01 mM with the Triglyceride Assay Buffer. Add 0, 10, 20, 30, 40, 50 μl into each well individually. Adjust volume to 50 μl/well with Triglyceride Assay Buffer to generate 0.1, 0.2, 0.3, 0.4, 0.5 nmol/well of Triglyceride Standard.

Sample Preparation:

Add 5 μl test samples in a 96-well clear bottom black plate, Adjust to the final volume of 50 μl/well with Triglyceride Assay Buffer.

Add 2 μl of lipase to each standard and sample well. Mix and incubate 20 min at RT to convert triglyceride to glycerol and fatty acid.

For the Triglyceride Reaction Mix: mix enough reagents for the number of samples and standards to be performed. For each well, prepare a total 50 μl Reaction Mix:

| | |
|---|---|
| 47.6 μl | Triglyceride Assay Buffer |
| 0.4 μl | Triglyceride Probe |
| 2 μl | Triglyceride Enzyme Mix |

Add 50 μl of the Reaction Mix to each well containing the Triglyceride Standard, test samples and controls. Mix well. Incubate at room temperature for 30 minutes, protect from light.

Measure fluorescence at Ex/Em 535/590 nm in ENSPIRE.

Calculations:

Correct background by subtracting the value derived from the 0 triglyceride standard from all sample readings. Plot the standard curve. Apply sample Readings to the standard curve.

Triglyceride concentration can then be calculated:

$$C = Ts/Sv \ (nmol/\mu l \ or \ \mu mol/ml \ or \ mM)$$

Where: Ts is triglyceride amount from standard curve (nmol).

Sv is the sample volume (before dilution) added in sample wells (μl).

Results

TABLE 5

Figure 3:
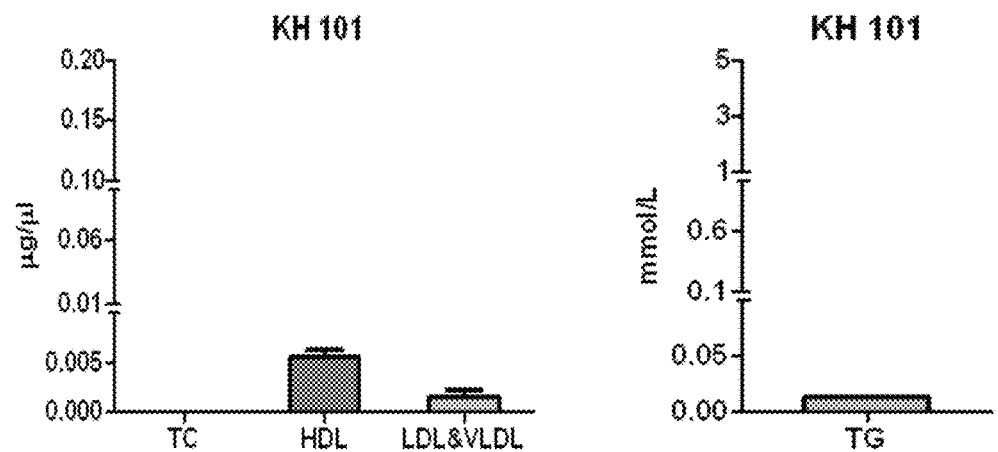
FIG. 3 shows the quantification of TC, HDL, LDL/VLDL and TG of sample KH 101.

Quantification of TC, HDL, LDL/VLDL and TG of sample KH 101 (FIG. 3)

| Sample | TC (μg/μl) | HDL (μg/μl) | LDL/VLDL (μg/μl) | TG (mmol/L) |
|---|---|---|---|---|
| KH 101 | 0.000 ± 0.000 | 0.006 ± 0.000 | 0.001 ± 0.000 | 0.013 ± 0.000 |

TABLE 6

Figure 4:
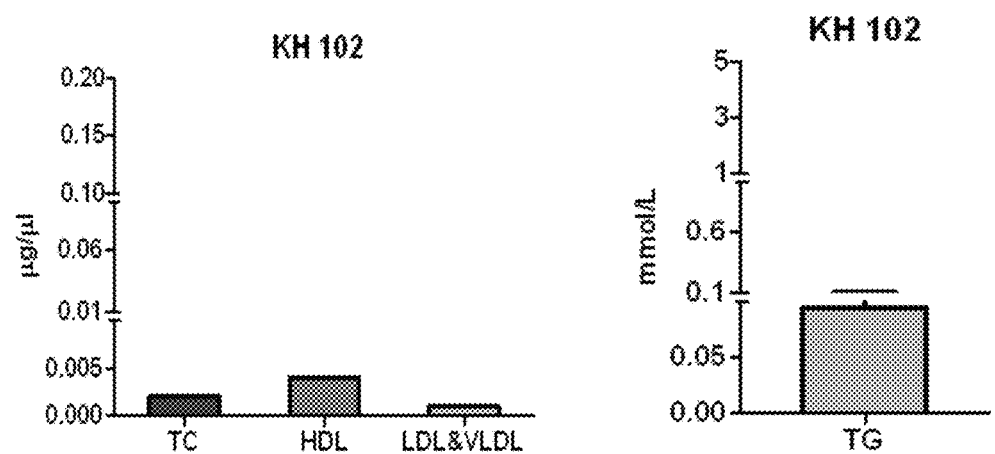
FIG. 4 shows the quantification of TC, HDL, LDL/VLDL and TG of sample KH 102.

Quantification of TC, HDL, LDL/VLDL and TG of sample KH102 (FIG. 4)

| Sample | TC (μg/μl) | HDL (μg/μl) | LDL/VLDL (μg/μl) | TG (mmol/L) |
|---|---|---|---|---|
| KH 102 | 0.002 ± 0.000 | 0.004 ± 0.000 | 0.001 ± 0.000 | 0.094 ± 0.011 |

TABLE 7

Figure 5:
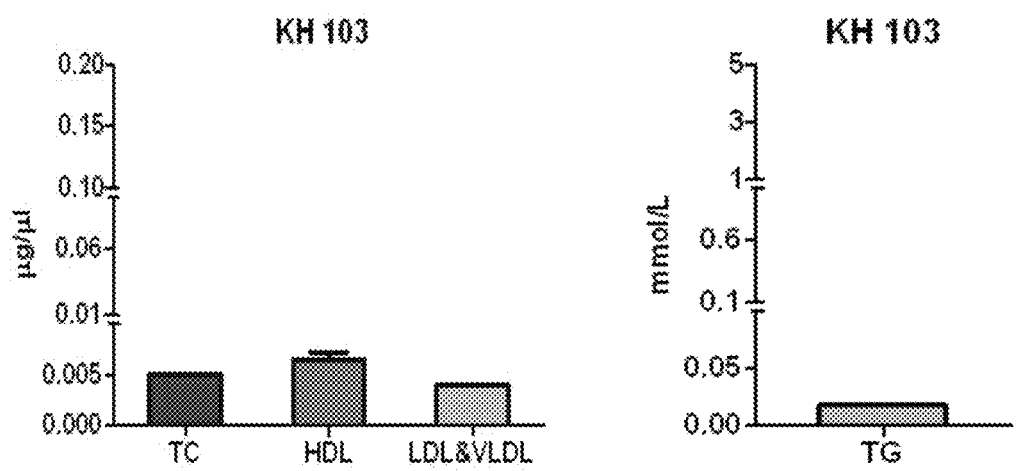
FIG. 5 shows the quantification of TC, HDL, LDL/VLDL and TG of sample KH 103.

Quantification of TC, HDL, LDL/VLDL and TG of sample KH 103 (FIG. 5)

| Sample | TC (μg/μl) | HDL (μg/μl) | LDL/VLDL (μg/μl) | TG (mmol/L) |
|---|---|---|---|---|
| KH 103 | 0.005 ± 0.000 | 0.007 ± 0.000 | 0.004 ± 0.000 | 0.018 ± 0.000 |

TABLE 8

Figure 6:
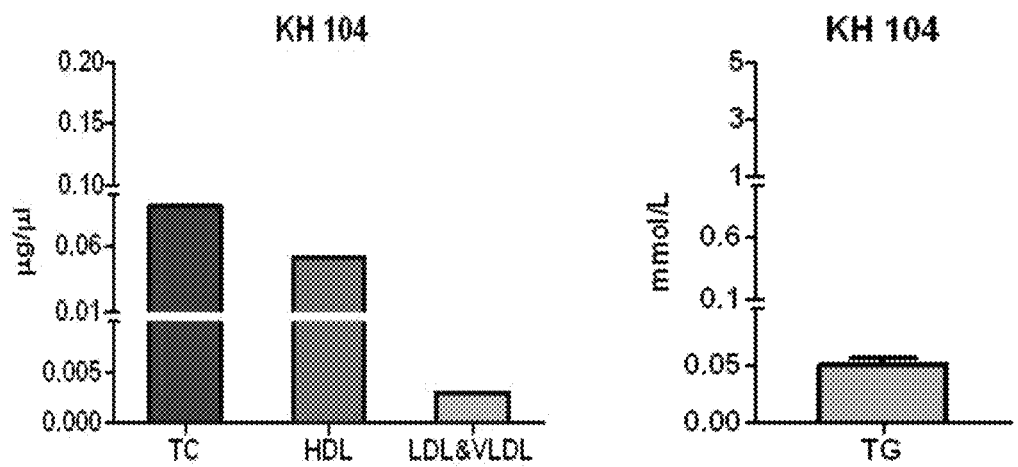
FIG. 6 shows the quantification of TC, HDL, LDL/VLDL and TG of sample KH 104.

Quantification of TC, HDL, LDL/VLDL
and TG of sample KH 104 (FIG. 6)

| Sample | TC (µg/µl) | HDL (µg/µl) | LDL/VLDL (µg/µl) | TG (mmol/L) |
|---|---|---|---|---|
| KH 104 | 0.091 ± 0.000 | 0.052 ± 0.001 | 0.003 ± 0.000 | 0.051 ± 0.006 |

TABLE 9

Figure 7:
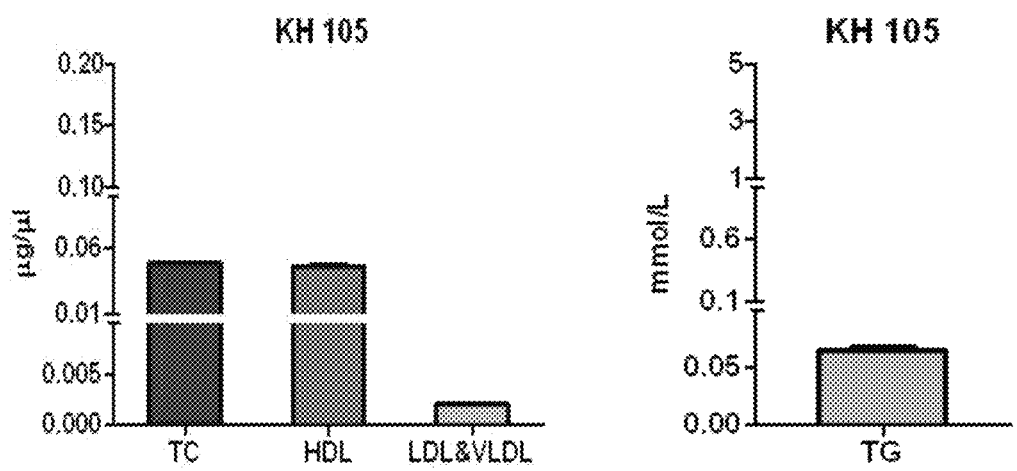
FIG. 7 shows the quantification of TC, HDL, LDL/VLDL and TG of sample KH 105.

Quantification of TC, HDL, LDL/VLDL
and TG of sample KH 105 (FIG. 7)

| Sample | TC (µg/µl) | HDL (µg/µl) | LDL/VLDL (µg/µl) | TG (mmol/L) |
|---|---|---|---|---|
| KH 105 | 0.049 ± 0.001 | 0.046 ± 0.001 | 0.002 ± 0.000 | 0.064 ± 0.004 |

TABLE 10

Figure 8:
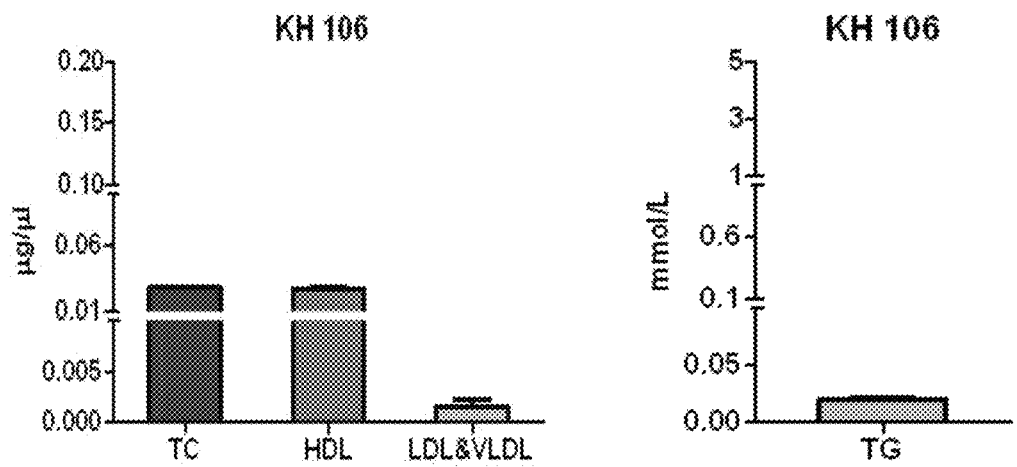
FIG. 8 shows the quantification of TC, HDL, LDL/VLDL and TG of sample KH106.

Quantification of TC, HDL, LDL/VLDL
and TG of sample KH 106 (FIG. 8)

| Sample | TC (µg/µl) | HDL (µg/µl) | LDL/VLDL (µg/µl) | TG (mmol/L) |
|---|---|---|---|---|
| KH 106 | 0.029 ± 0.000 | 0.028 ± 0.001 | 0.001 ± 0.000 | 0.021 ± 0.000 |

TABLE 11

Figure 9:
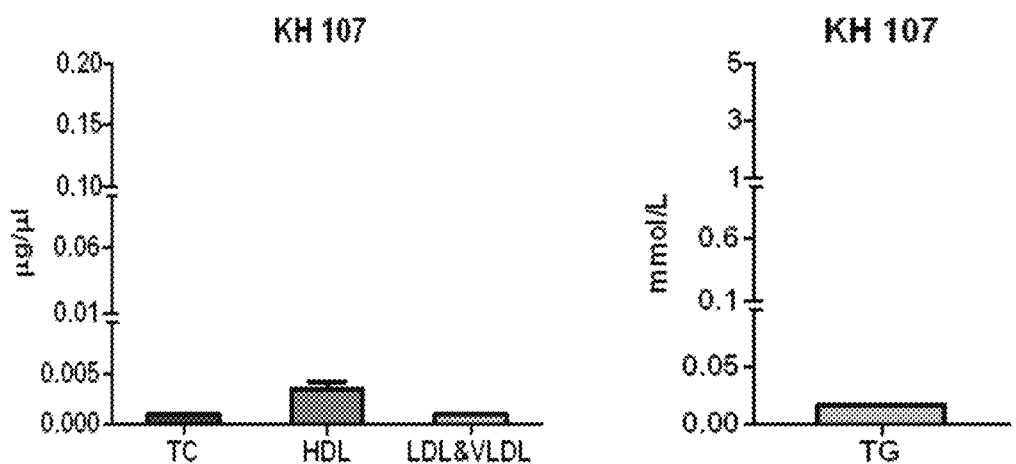
FIG. 9 shows the quantification of TC, HDL, LDL/VLDL and TG of sample KH 107.

Quantification of TC, HDL, LDL/VLDL
and TG of sample KH 107 (FIG. 9)

| Sample | TC (µg/µl) | HDL (µg/µl) | LDL/VLDL (µg/µl) | TG (mmol/L) |
|---|---|---|---|---|
| KH 107 | 0.001 ± 0.000 | 0.003 ± 0.000 | 0.001 ± 0.000 | 0.017 ± 0.001 |

TABLE 12

Figure 10:
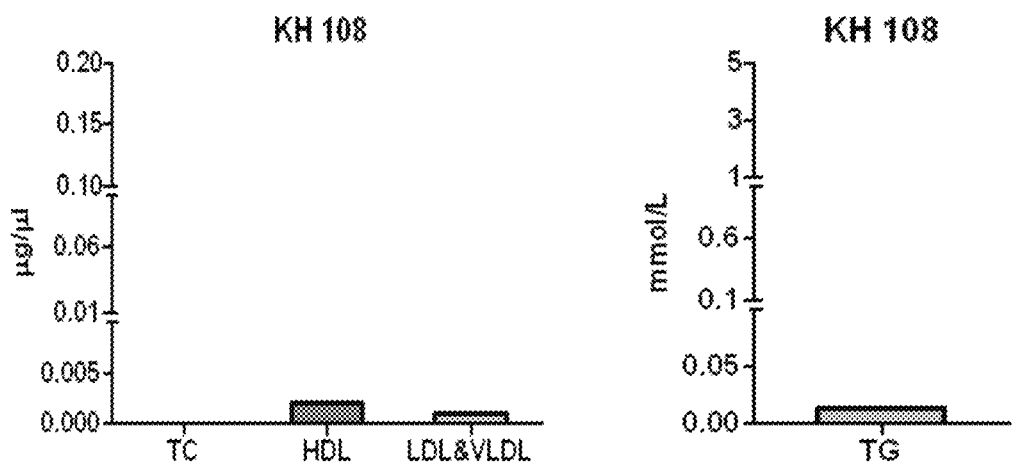
FIG. 10 shows the quantification of TC, HDL, LDL/VLDL and TG of sample KH 108.

Quantification of TC, HDL, LDL/VLDL
and TG of sample KH 108 (FIG. 10)

| Sample | TC (µg/µl) | HDL (µg/µl) | LDL/VLDL (µg/µl) | TG (mmol/L) |
|---|---|---|---|---|
| KH 108 | 0.000 ± 0.000 | 0.002 ± 0.000 | 0.001 ± 0.000 | 0.014 ± 0.000 |

TABLE 13

Figure 11:
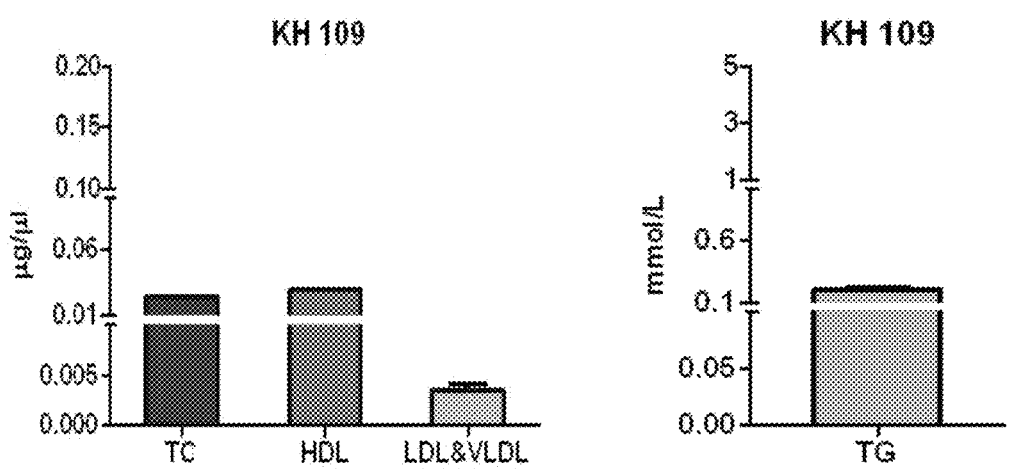
FIG. 11 shows the quantification of TC, HDL, LDL/VLDL and TG of sample KH 109 White wine.

Quantification of TC, HDL, LDL/VLDL
and TG of sample KH 109 (FIG. 11)

| Sample | TC (µg/µl) | HDL (µg/µl) | LDL/VLDL (µg/µl) | TG (mmol/L) |
|---|---|---|---|---|
| KH 109 | 0.025 ± 0.001 | 0.03 ± 0.000 | 0.004 ± 0.000 | 0.207 ± 0.012 |

TABLE 14

Figure 12:
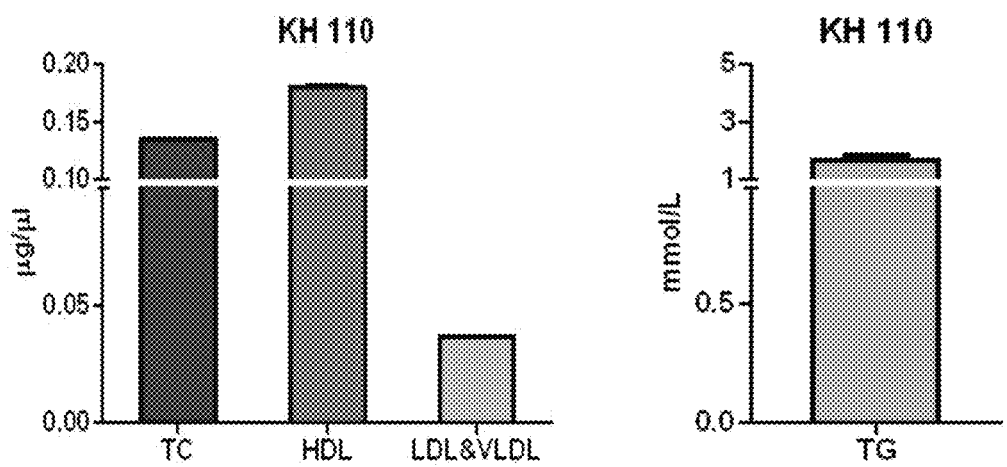
FIG. 12 shows the quantification of TC, HDL, LDL/VLDL and TG of sample KH 110 Red wine.

Quantification of TC, HDL, LDL/VLDL
and TG of sample KH 110 (FIG. 12)

| Sample | TC (µg/µl) | HDL (µg/µl) | LDL/VLDL (µg/µl) | TG (mmol/L) |
|---|---|---|---|---|
| KH 110 | 0.134 ± 0.001 | 0.18 ± 0.001 | 0.037 ± 0.000 | 1.684 ± 0.154 |

TABLE 15

Figure 13:
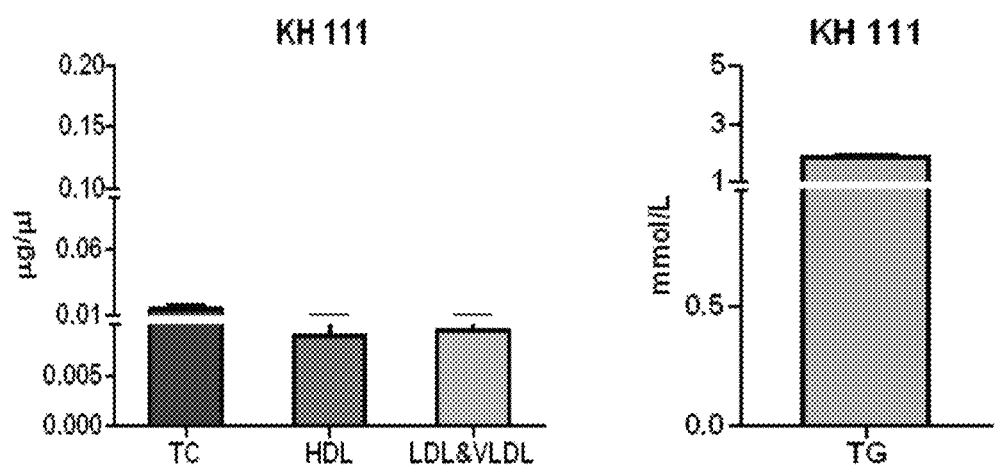
FIG. 13 shows the quantification of TC, HDL, LDL/VLDL and TG of sample KH 111 Young Soy Edamame.

Quantification of TC, HDL, LDL/VLDL and TG of
sample KH 111 (FIG. 13)

| Sample | TC (µg/µl) | HDL (µg/µl) | LDL/VLDL (µg/µl) | TG (mmol/L) |
|---|---|---|---|---|
| KH 111 | 0.015 ± 0.003 | 0.009 ± 0.001 | 0.01 ± 0.001 | 1.865 ± 0.028 |

TABLE 16

Figure 14:
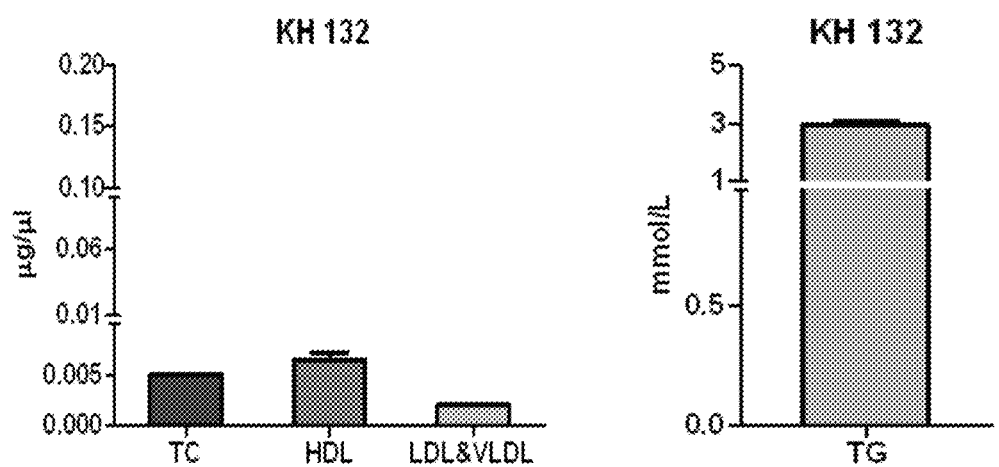
FIG. 14 shows the quantification of TC, HDL, LDL/VLDL and TG of sample KH 132 Red hot pepper.

Quantification of TC, HDL, LDL/VLDL and TG of
sample KH 132 (FIG. 14)

| Sample | TC (µg/µl) | HDL (µg/µl) | LDL/VLDL (µg/µl) | TG (mmol/L) |
|---|---|---|---|---|
| KH 132 | 0.005 ± 0.000 | 0.007 ± 0.001 | 0.002 ± 0.000 | 2.928 ± 0.161 |

In Vitro Study 2—Lipid Panel

Figure 15:
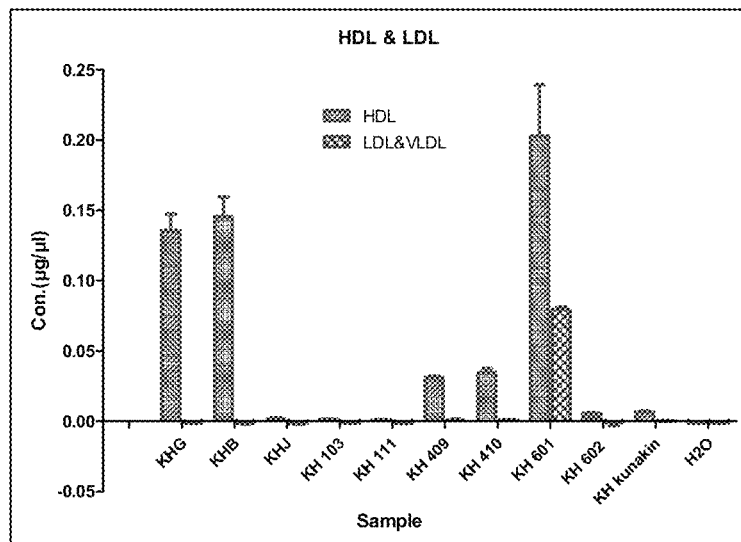
FIG. 15 shows the HDL and LDL of KH Green and KH Blue.
Figure 16:
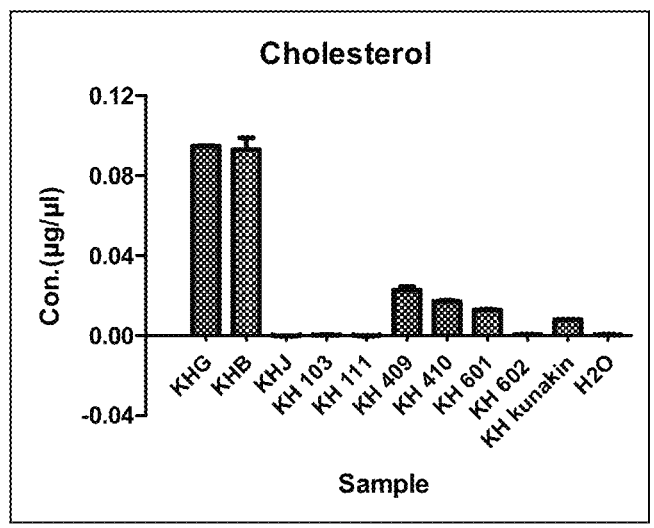
FIG. 16 shows the Cholesterol in KH Green and KH Blue.
Figure 17:
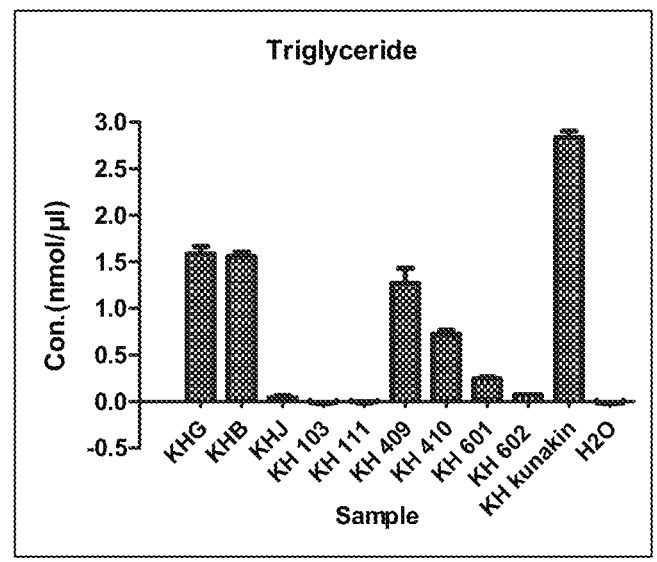
FIG. 17 shows the Trygliceride in KH Green and KH Blue.
Figure 18:
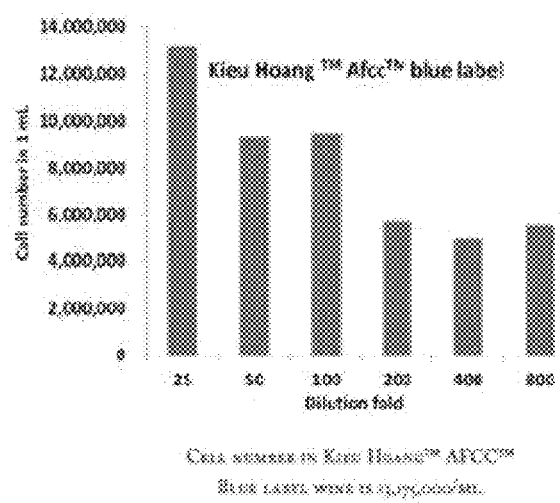
FIG. 18 shows the cell count on KIEU HOANG™ Blue label is 13,175,000/mL.
Figure 19:
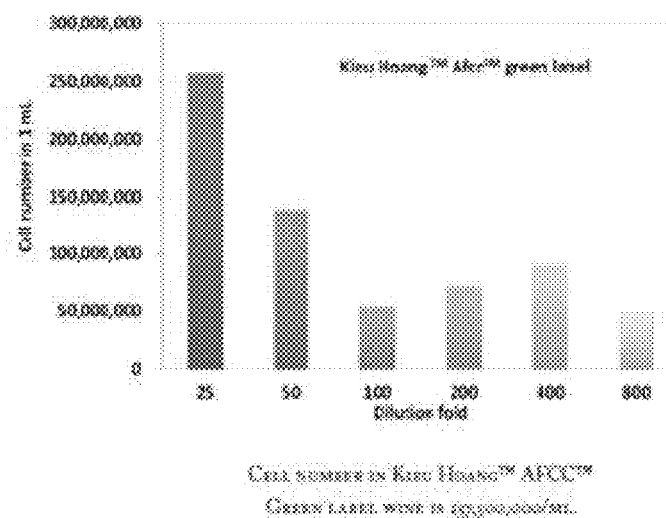
FIG. 19 shows the cell count on KIEU HOANG™ Green label is 257,500,000/mL.
Figure 20:
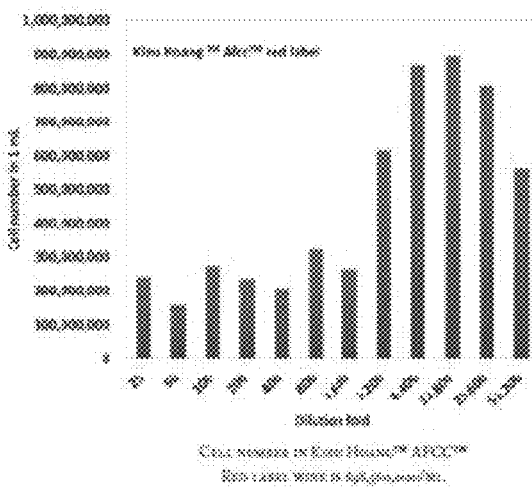
FIG. 20 shows the cell count on KIEU HOANG™ Red label is 898,560,000/mL.
Figure 21:
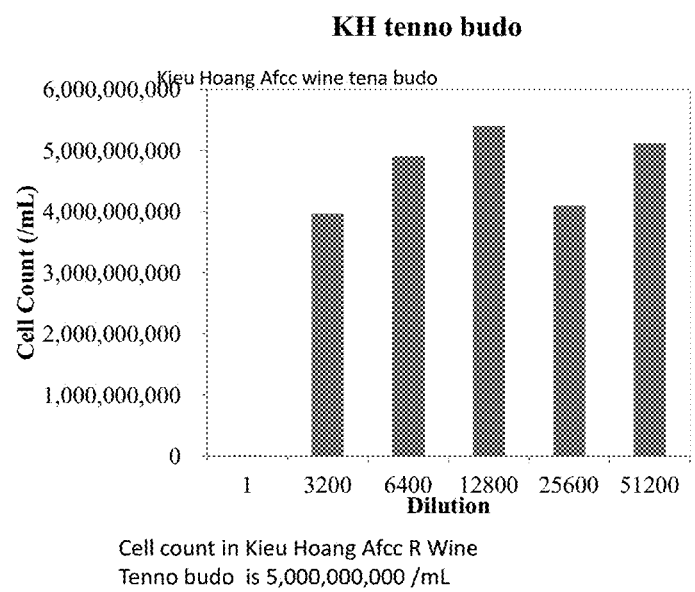
FIG. 21 shows the cell count on KIEU HOANG™ Tennobudo is 5,000,000,000/mL.
Figure 25:
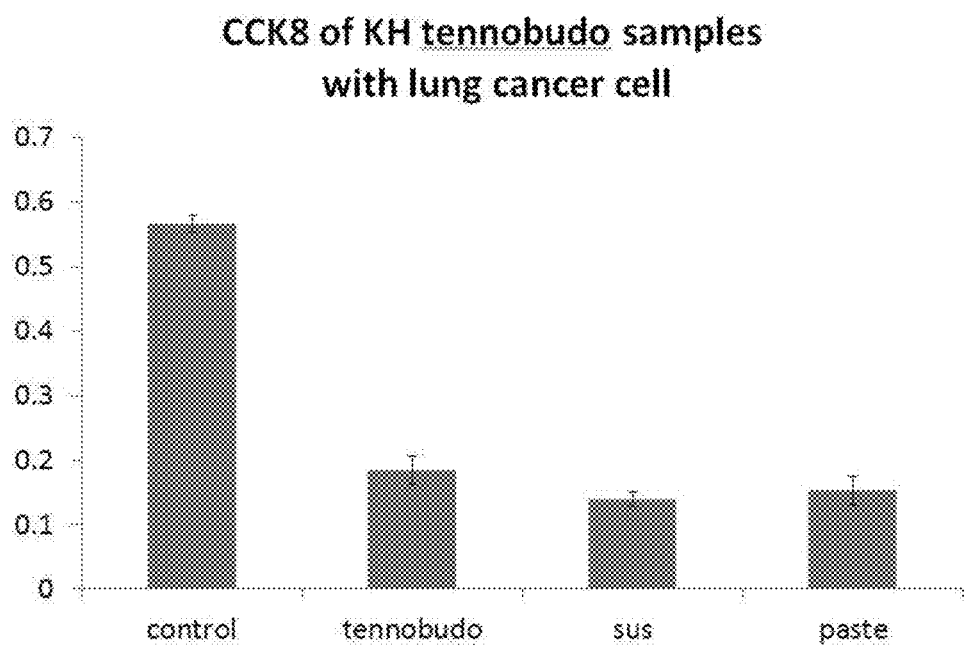
FIG. 25 shows the inhibition of KIEU HOANG™ Tennobudo label in lung cancer.
Figure 26:
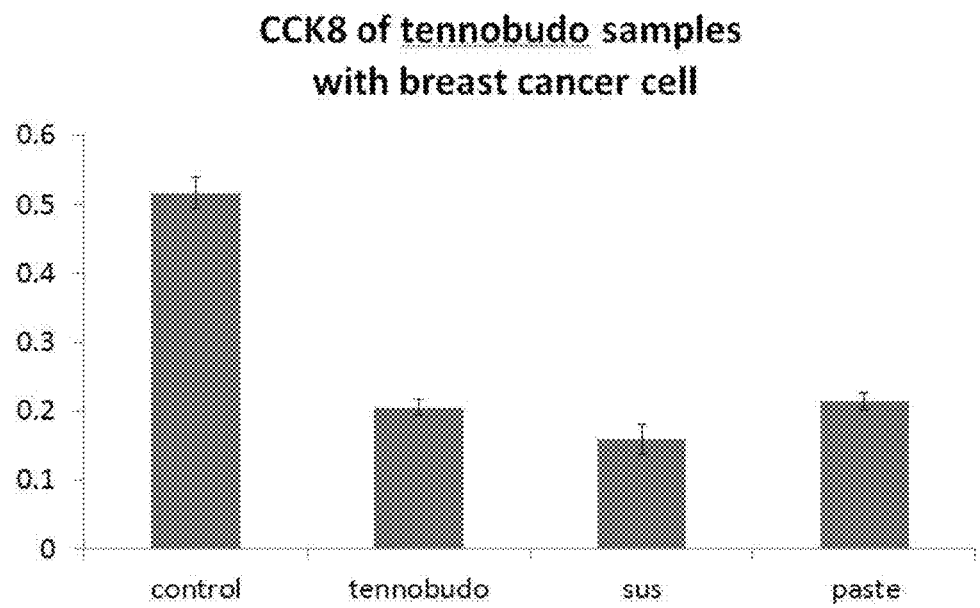
FIG. 26 shows the inhibition of KIEU HOANG™ Tennobudo label in breast cancer.

The second lipid panel was performed on the KIEU HOANG™ Blue Label Wine as well as the Green Label Wine by Wuxi Pharma, one of the top ten CRO labs in the world. It was found that the levels of HDL are also very high (FIGS. 15-17).

In Vitro Study 3—Living Cells in Wine

The living cells are also found in all KIEU HOANG™ wine, from the low level of less than one million cells per mL, up to five billion cells per mL (FIGS. 18-21). Another finding shows that the taste of wine will be better with the higher concentration of cells. A number of studies also show the higher concentration of cells, the better efficacy.

In Vitro Study 4—Lung and Breast Cancer

It was found in the in vitro study of the four different labels of KIEU HOANG™ wine that the wine can inhibit the growth of the cancer cells, especially the lung and breast cancers (FIGS. 22-26).

In Vitro Study 5—Kieu Hoang™ Wine Green Label Wine and Diabetics

Figure 27:
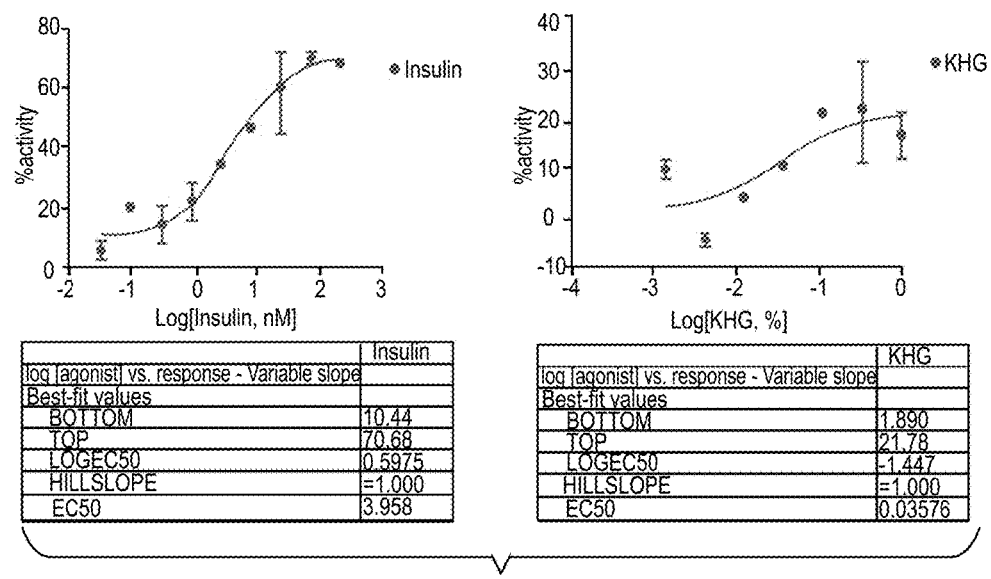
FIG. 27 shows the Glucose uptake in KIEU HOANG™ Green label, which helps to generate insulin for glucose uptake in diabetics due to the mechanism as described herein.
Figure 28:
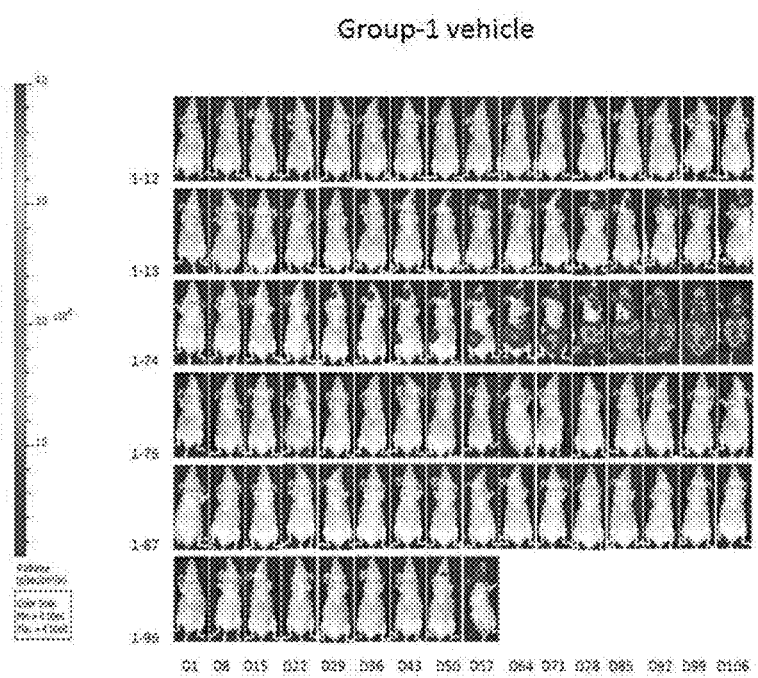
FIG. 28 shows the Leukemia cancer signal in mice, group 1 (Vehicle).
Figure 29:
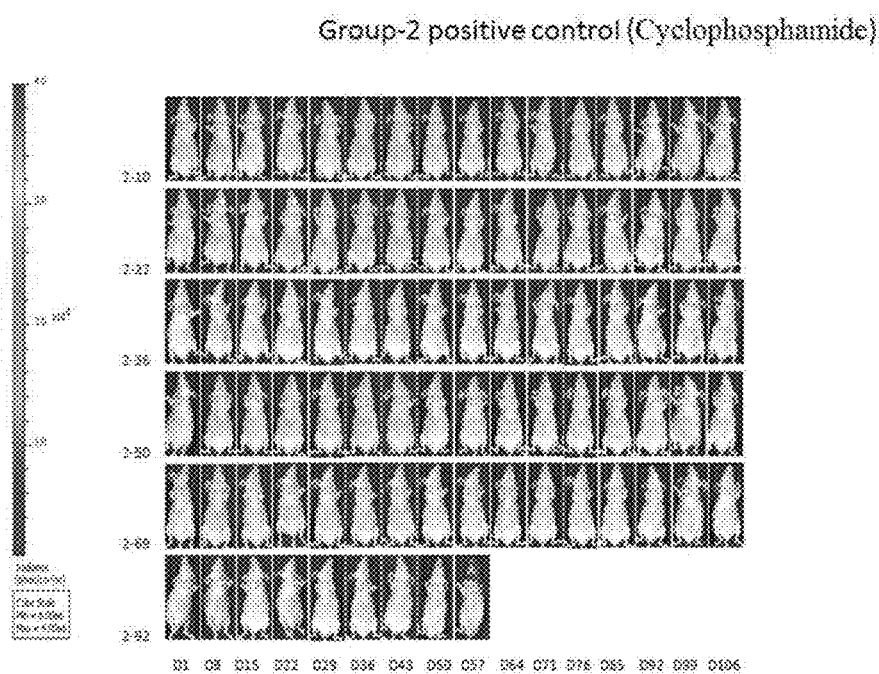
FIG. 29 shows the Leukemia cancer signal in mice, group 2 (Positive control).
Figure 30:
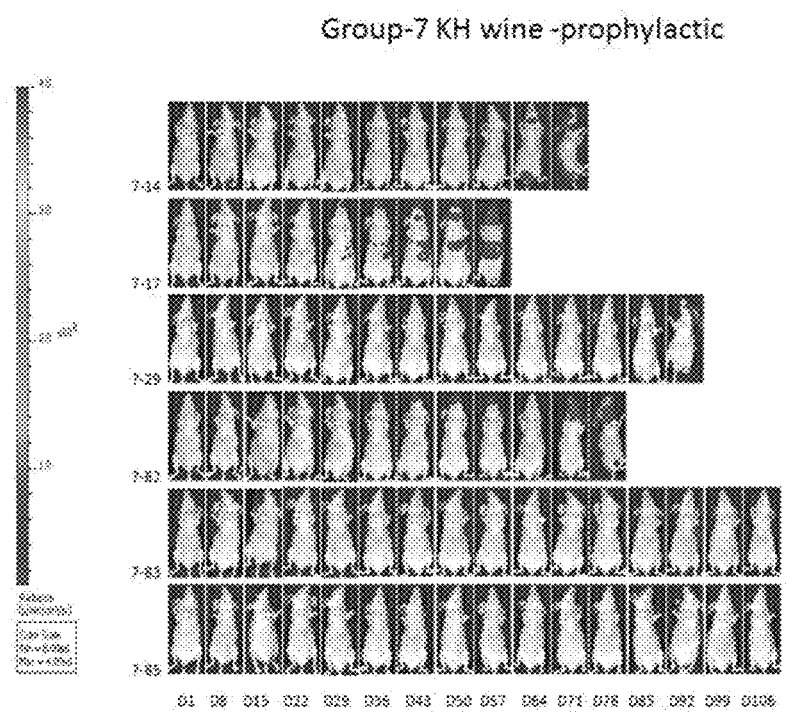
FIG. 30 shows the Leukemia cancer signal in mice, group 7 (Prophylactic).
Figure 31:
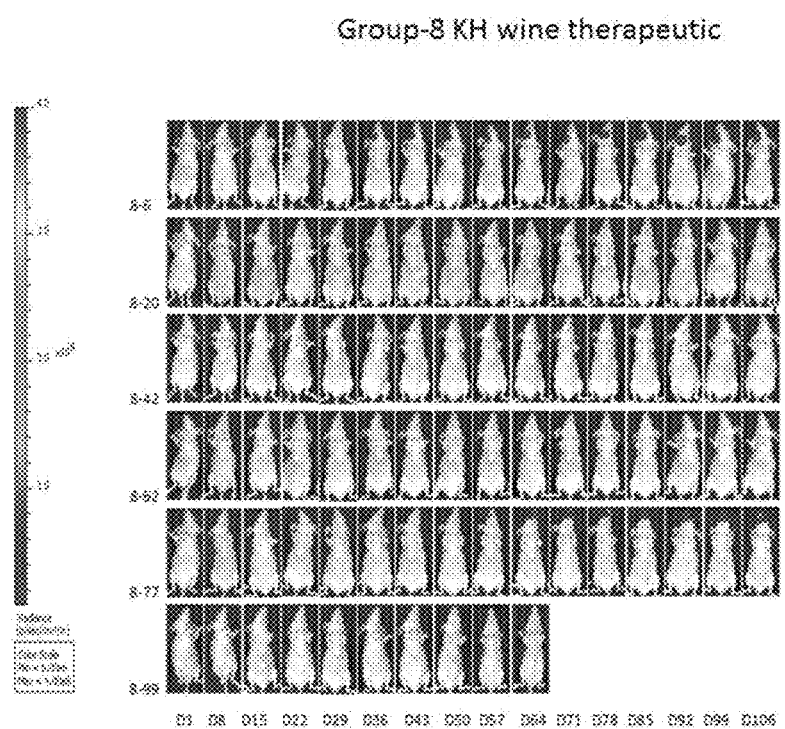
FIG. 31 shows the Leukemia cancer signal in mice, group 8 (Therapeutic).

An in vitro study was performed by Wuxi Pharma, one of the ten largest CRO labs in the world. The study demonstrated that KIEU HOANG™ Green Label with the cell count of 257,500,000 mL can help in glucose uptake, which means that after drinking wine, diabetic patients have a lower sugar level in their systems (FIG. 27).

The higher the number of cells, the lower the sugar level is, the mechanism being due to KH good healthy living cells found in KIEU HOANG™ wine. Wine formulations containing KH wine good healthy cells in which the RNA synthesizes good proteins send signals to the damaged, sick, and bad cells that trigger synthesis of good proteins to transform the cells to become good healthy cells. Further, signals are sent to the other currently undamaged cells to synthesize good proteins to protect them from being damage, infection, and from being prone to DNA and other cellular alterations. Signals are sent to the patient's body to produce new cells that are healthy and to forbid them from being affected by intra- and extracellular damaging signals.

In Vivo Study 1: Leukemia Cancer Vs Kieu Hoang Wine Red Label

The in vivo study was also conducted at Wuxi Pharma. The study found that KIEU HOANG wine Red label helped to slow the growth of the cancer to compare with the vehicle control (FIGS. 28-31).

Volunteer Study 1—Lipid Panel

Since 1985, the volunteer's cardiologist prescribed Lipitor® but the volunteer never took the prescribed drug. Instead, the volunteer started running for two hours, exercising every day since 1983.

In Jan. 28, 2013, the volunteer performed a health checkup. The triglyceride level was 1,114 mg/dL, the cholesterol level was 346 mg/d, the HDL level was 44 mg/dL, LDL levels were beyond an upper limit (>400 mg/dL), and high blood pressure was found. The volunteer refused to take the drug Lipitor and also the drug to lower blood pressure. Instead, he turned to KIEU HOANG™ wine in which he discovered that KIEU HOANG™ wine had the highest levels of High Density Lipoprotein. Therefore, the volunteer believed that KIEU HOANG™ wine would help in lowering the cholesterol, triglyceride, and LDL levels. The results were confirmed.

In June 2013, after the volunteer's cholesterol test at Rui Jin Hospital, his doctor concluded that triglyceride, hypertension, and cholesterol levels were still high, but his doctor did not know how high his levels were in Jan. 28, 2013 test.

During the period from Jan. 28, 2013 until Jun. 3, 2013, the volunteer drank two glasses of KIEU HOANG™ Blue, Green, Red, or Gold label per night. Triglyceride levels dropped from 1,114 mg/dL down to 379 mg/dL. Cholesterol dropped from 346 mg/dL down to 235 mg/dL. HDL levels increased from 44 mg/dL up to 48 mg/dL. LDL dropped down from beyond the up limit >400 mg/dL to 125 mg/dL, as described in the charts below.

|  | Jan. 01, 2013 | Jun. 3, 2013 |
| --- | --- | --- |
| Triglyceride | 1114 mg/dL | 379 mg/dL |
| Cholesterol | 346 mg/dL | 235 mg/dL |
| HDL | 44 mg/dL | 48 mg/dL |
| LDL | Beyond up limit (>400 mg/dL) | 125 mg/dL |

On Aug. 6, 2013, the volunteer's family physician looked at the results from the Rui Jin Hospital and prescribed some medicines which contained chemicals to decrease cholesterol and triglyceride levels. Instead of taking the medications, the volunteer continued drinking KIEU HOANG™ wines and in addition began to take 2 capsules of KUNAKIN™ (359 proteins in soy), 2 capsules of KUNAKIN™ (grape concentrate with seed, flesh, stem, and skin), and 4 capsules of KHCARE™ CardioTrim® Men's Formula, along with an hour of fast walking on treadmill while practicing a healthy diet.

On Sep. 10, 2013, a test was performed again after the change of regiment of Aug. 6, 2013. The results showed a decrease of triglyceride levels from 1,114 mg/dL down to 101 mg/dL. Cholesterol levels went down from 346 mg/dL to 235 mg/dL. HDL increased from 44 mg/dL to 50 mg/dL. LDL went from beyond an upper limit of >400 mg/dL to 158 mg/dL. Triglyceride levels decreased 1,102.9%. Cholesterol levels decreased 140%. HDL increased 110%. LDL decreased 253%, as described in the charts below.

|  | Jan. 01, 2013 | Jun. 3, 2013 | Sept. 10, 2013 | Increase (%) |
| --- | --- | --- | --- | --- |
| Triglyceride | 1114 mg/dL | 379 mg/dL | 101 mg/dL | −1102.9% |
| Cholesterol | 346 mg/dL | 235 mg/dL | 235 mg/dL | −140% |
| HDL | 44 mg/dL | 48 mg/dL | 50 mg/dL | 110% |
| LDL | Beyond up limit (>400 mg/dL) | 125 mg/dL | 158 mg/dL | −253% |

Volunteer Study 2—Lower Sugar Levels in Diabetics

The measurement of sugar level of a particular volunteer was performed in mid-November and mid December 2014. In mid-November three volunteers consumed one bottle of KIEU HOANG™ wine Red label. After dinner the particular volunteer measured his sugar level, which showed a reading of 7.0. In mid-December the same three volunteers consumed a bottled of Tennobuddo (former Guilliams), and after dinner the particular volunteer measured his sugar level, which showed a reading of 6.9. The sugar reading level was performed twice to prove it. For the particular volunteer, even if he administered the prescribed chemical drug, his lowest sugar level was typically 11.5-12 mmol/L.

As such, KIEU HOANG™ wine Green Label™, Red Label™, Yellow Label™, Purple Label™, and/or Tenno-Budo™ (former Guilliams) with the cell contents between 275,000,000/cells per ml up to 5,000,000,000 (5 billion) living cells per ml, will help to lower sugar level in diabetics down to 7 and 6.9 mmol/L from 11.5-12 mmol/L after dinner.

Figure 32:
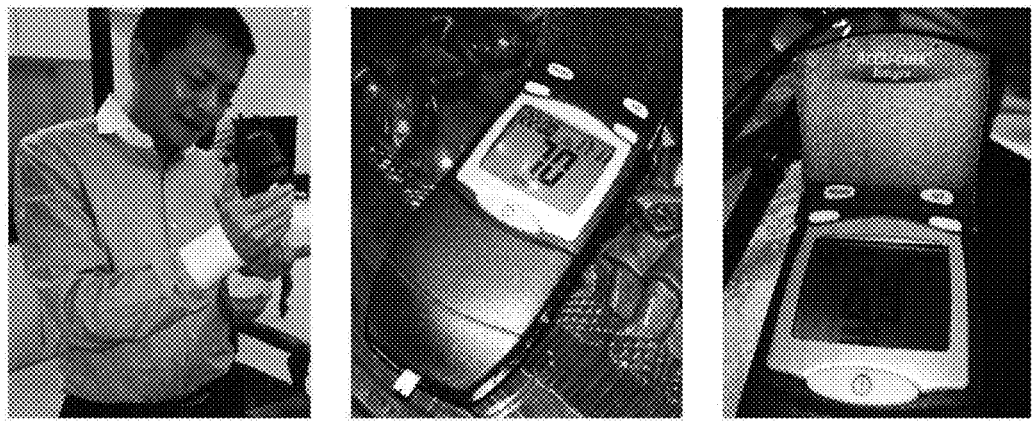
FIG. 32 shows the inventor's business partner testing his blood sugar levels after drinking KIEU HOANG™ Red label and Tennobudo wines.

It was found that the higher the number of cells, the better for not only lowering down sugar level in diabetics, but also for the taste of the wine. FIG. 32 shows a volunteer testing his blood sugar levels after drinking KIEU HOANG™ Red label and Tennobudo wines.

Volunteer Study 3—the Inventor's Living Moving Cells Vice Versa Living Cells in Kieu Hoang Wine Cells from plants, animals, and humans are the same and live forever. For example, even after a cancer patient dies, the bad cancer cells are still alive. The wine grape has been used to make wine through crushing, and at different temperatures, bacteria and virus can be eliminated at a low pH of 3.5-4.0. However, the living cells are still present in the wine.

The cells from the inventor (A), from KH103 (B) and from Porcine TB (C) are show in FIG. 39A-C for comparison. In order to prove cells are still alive in the human component, the skin under the feet of the inventor was removed from the body, ground into powder, centrifuged at high speed, and underwent high temperature of heating up to 120° C. After the aforementioned steps, the cells were still alive. The cells consist of two rings called double ring. The outer ring is DNA and the inner ring is RNA.

Figure 33:
FIG. 33 shows the human moving cells in the inventor's feet. Still pictures from video to prove the cells are moving are taken from 00:54 seconds into the video.
Figure 34:
FIG. 34 shows the human moving cells in the inventor's feet. Still pictures from video to prove the cells are moving are taken from 00:59 seconds into the video.
Figure 35:
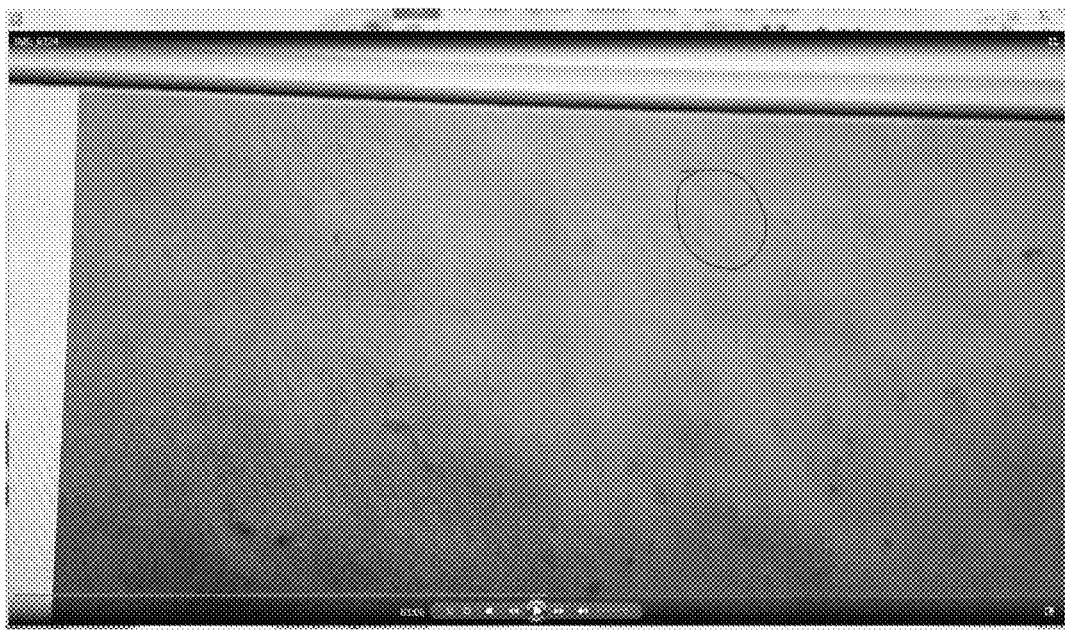
FIG. 35 shows the human moving cells in the inventor's feet. Still pictures from video to prove the cells are moving are taken from 01:06 seconds into the video.

FIG. 33 shows human moving cells in the inventor's feet. Still pictures were taken from video to prove the cells are moving from 00:54 seconds into the video. FIG. 34 shows human moving cells in the inventor's feet. Still pictures were taken from video to prove the cells are moving from 00:59 seconds into the video. FIG. 35 shows human moving cells in the inventor's feet. Still pictures were taken from video to prove the cells are moving from 01:06 seconds into the video.

Figure 36:
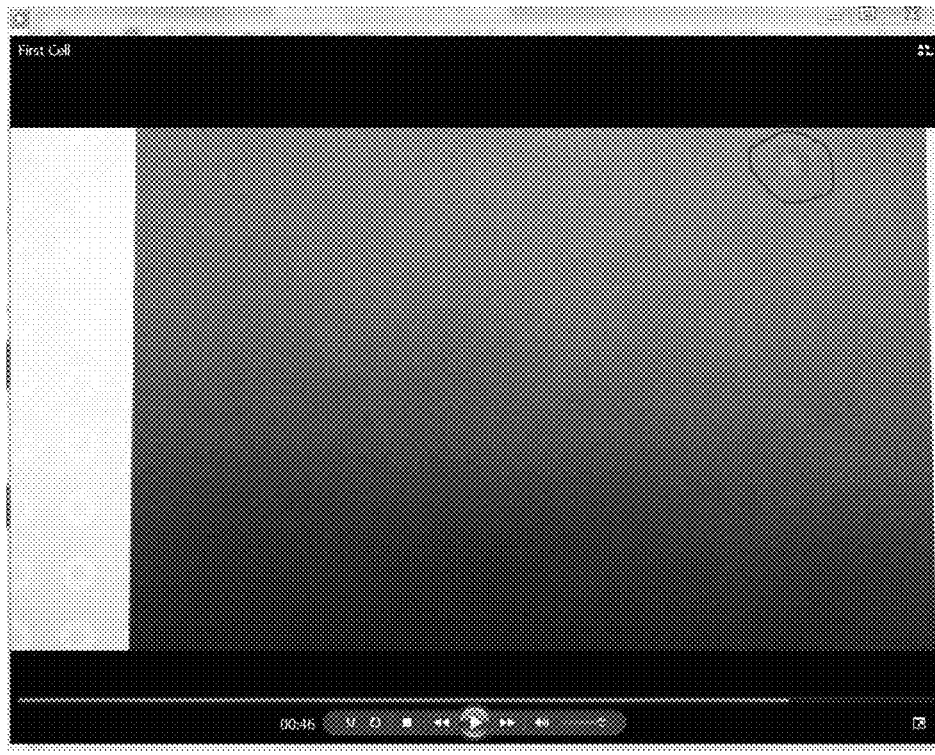
FIG. 36 shows the moving cells of the plant in KIEU HOANG™ wine. Still pictures from video to prove the cells are moving are taken from 00:46 seconds into the video.
Figure 37:
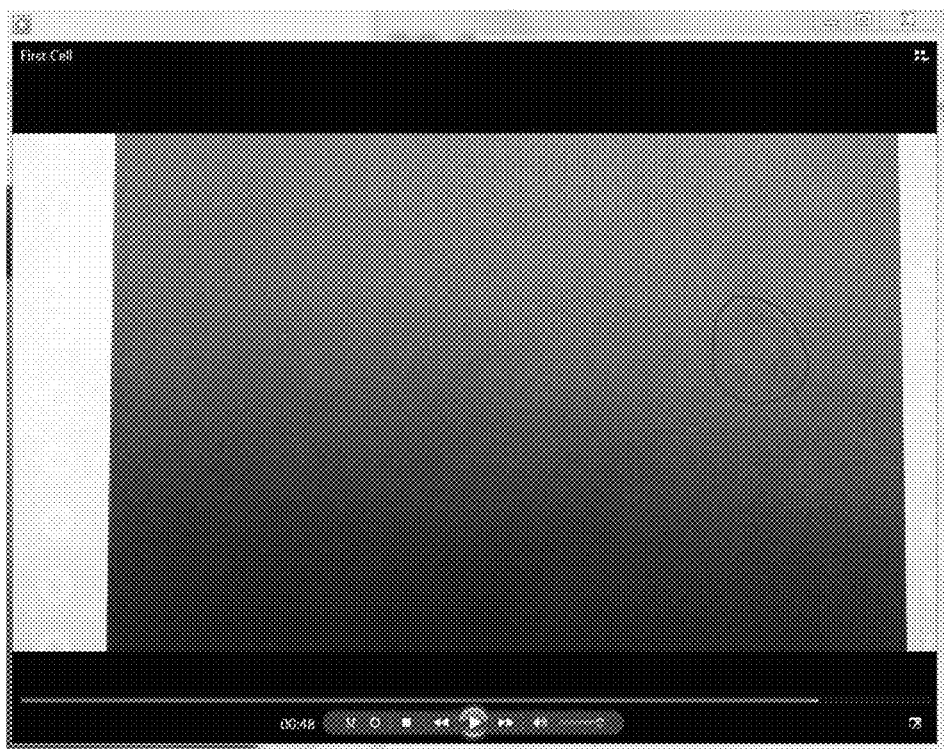
FIG. 37 shows the moving cells of the plant in KIEU HOANG™ wine. Still pictures from video to prove the cells are moving are taken from 00:48 seconds into the video.
Figure 38:
FIG. 38 shows the moving cells of the plant in KIEU HOANG™ wine. Still pictures from video to prove the cells are moving are taken from 00:50 seconds into the video.

FIG. 36 shows the moving cells of the plant in KIEU HOANG™ wine. Still pictures were taken from video to prove the cells are moving from 00:46 seconds into the video. FIG. 37 shows the moving cells of the plant in KIEU HOANG™ wine. Still pictures were taken from video to prove the cells are moving from 00:48 seconds into the video. FIG. 38 shows the moving cells of the plant in KIEU HOANG™ wine. Still pictures were taken from video to prove the cells are moving from 00:50 seconds into the video.

In Vitro Study 6—KH601 Grape Seed Extract and KH602 Resveratrol

An in vitro study of KH601 and KH602 was also performed by Wuxi Pharma. The study showed that KH601 and KH602 contain high density lipoprotein (APOA-1) but are low in cholesterol and triglyceride.

In Vivo Study 2—KH609 Grape Seed Extract and KH610 Resveratrol

In this study of KH609 and KH610 vs Leukemia cancer, it was found that KH609 and KH610 have helped to slow the growth of the Leukemia cancer cells.

In Vitro Study 7—Testing by SDS Page and Cell Count of KUNAMIN™

Figure 41:
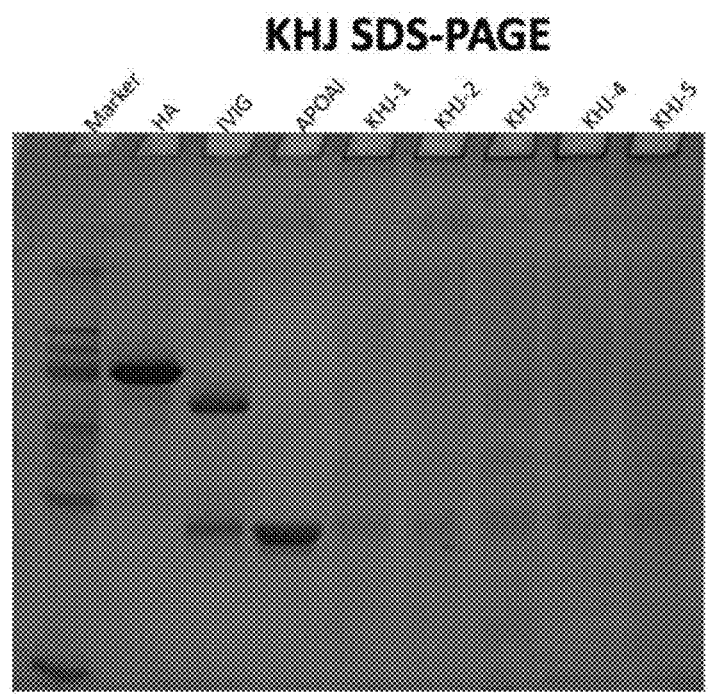
FIG. 41 shows an image of the KHJ SDS-Page, particularly the band of molecular weight of KHJ-1, KHJ-2, KHJ-3, KHJ-4 and KHJ-5 at different dilutions similar to that of immunoglobulin and High density lipoprotein (APOA-1) of the human plasma.

KHJ, KH601, and KH602 are the code names of KUNAMIN™. SDS Page was performed to examine the molecular weight of KUNAMIN™. It was found that the molecular weight of KUNAMIN™ is similar to that of immunoglobulin and APOA1 (High Density Lipoprotein) found in human plasma (FIG. 41).

Figure 42:
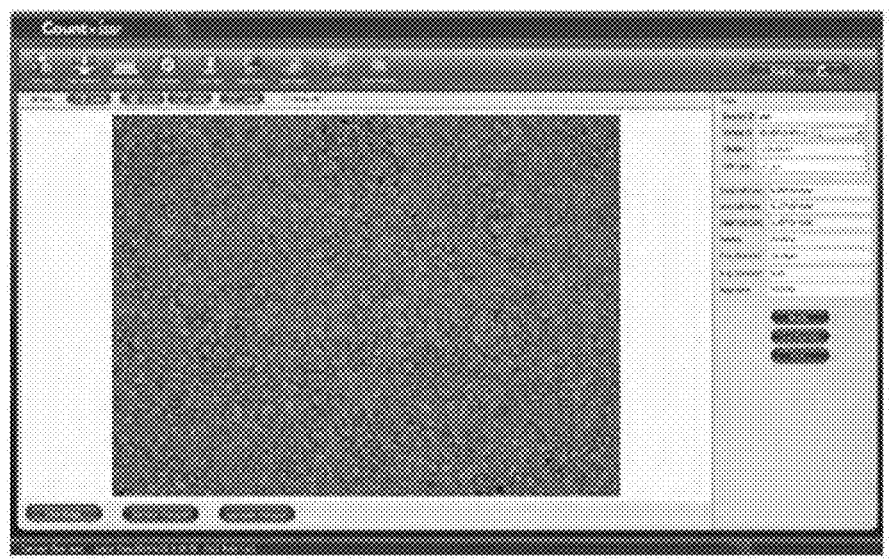
FIG. 42 shows an image of the cell count of KUNAMIN™.

KUNAMIN™ contains between cells from 10,000,000 cells per ml up to one billion cells count per ml in various concentration of KUNAMIN™ (FIG. 42).

In Vitro Study 8—Testing of HDL/VLDL/LDL and Triglyceride in KUNAMIN™

The study was performed at Wuxi Pharma to detect level of High Density Lipoprotein (HDL), LDL (Low Density Lipoprotein), and Very Low Density Lipoprotein (VLDL). KH601, one of the components in KUNAKIN™, has a very high level of High Density Lipoprotein (HDL), which is good cholesterol. KHJ and KH 601 have the lowest levels of LDL, VLDL, and triglyceride.

Glucose Uptake in KUNAMIN™

Glucose metabolism is a primary source of energy and biomaterials for the maintenance of cell homeostasis. Extra glucose is stored in the muscles and liver as glycogen which is hydrolyzed to glucose and released into the blood when needed. The rate of glucose uptake in cells is dynamic and tightly regulated by hormones and/or growth factors including insulin.

GLUT4 is the insulin-regulated glucose transporter found in adipose tissues and striated muscle (skeletal and cardiac) that is responsible for insulin-regulated glucose transport into the cell. Under conditions of low insulin, GLUT4 is sequestered in intracellular vesicles in muscle and fat cells. Insulin induces a rapid increase in the uptake of glucose by inducing the translocation of GLUT4 from these vesicles to the plasma membrane. As the vesicles fuse with the plasma membrane, GLUT4 transporters are inserted and become available for transporting glucose, and glucose absorption increases.

This study is using 2-deoxy-D-[$^3$H]-glucose to track the effect of testing proteins on the rate of glucose uptake in 3T3-L1 cells in responsive to insulin.

Materials and Reagents
Reagents:
HEPES, Invitrogen (Cat#15630130)
MgSO4, SIGMA (Cat#63138)
CaCl2, FLUKA (Cat#06991)
KCl, SIGMA (Cat#P9333)
NaCl, Fisher (Cat#BMA51202)
BSA, Gibco (Cat#A6003)
Deoxy-D-glucose, 2-[1,2-3H (N)], Perkin Elmer (Cat#NET328A250UC)
Insulin, Sigma (Cat#I2643)
2-DEOXY-D-GLUCOSE, Sigma (Cat#D6134)
FBS, Invitrogen (Cat#10100147)
DMEM, Invitrogen (Cat#11965118)
Dexamethasone, Sigma (Cat#D1756-25MG)
3-Isobutyl-1-methylxanthine, IBMX, Sigma (Cat#I5879)
Apparatus and Plates:
Top Seal-A sealing film, Perkin Elmer (Cat#6005250)
Tri-Carb, (Perkin Elmer)
96 Well Microplates (Nunc-442587)
96-well micro titer black clear plate (Greiner-655090)
Cell:
3T3-L1 fibroblasts cell (Cell bank of Chinese academy of sciences-Cat No. GNM25)
Testing Samples:
10 testing proteins were provided by RAAS US as shown in Table 17:

TABLE 17

| Testing Samples | Volume/Quality |
|---|---|
| KHG | 10 ml |
| KHB | 10 ml |
| KHJ | 10 ml |
| KH 103 | 10 ml |
| KH 111 | 10 ml |
| KH 409 | Powder |
| KH 410 | Powder |
| KH 601 | Powder |
| KH 602 | Powder |
| KH Kunakin | Powder |

Experimental Procedure

Dissolve the powder samples at 20 g: 100 ml ddH$_2$O. Filter the solid particles from the solution. Filter all the rest samples at the same time.

Cell culture: 3T3-L1 fibroblasts were cultured in culture medium I (DMEM containing 25 mM glucose, 1% PS, 10% FBS) at 37° C. with 5% CO2.

Cell differentiation: 3T3-L1 fibroblasts were differentiated into adipocytes 2 days post confluent with culture medium II (DMEM, 10% FBS, 1% PS) containing 1 ug/ml insulin, 1 uM dexamethasone, and 0.5 mM IBMX (day 0). Media were replaced with culture medium II containing 1 ug/ml insulin and culture 2 days. (day 2). Media is changed to 10% FBS/DMEM (day 4). Feed cells with 10% FBS/DMEM every two days. Full differentiation is usually achieved by day 8.

Glucose uptake assay: Seed 200 ul/well 2×10$^5$/ml 3T3-L1 adipocytes to 96 wells cell culture plate (culture medium II containing 1 ug/ml insulin), culture overnight at 37° C. with 5% CO2. 3T3-L1 adipocytes were incubated in serum free medium for starvation overnight. 3T3-L1 adipocytes were washed with KRPH buffer (5 mM Na2HPO4, 20 mM HEPES, pH 7.4, 1 mM MgSO4.1 mM CaCl2, 136 mM NaCl, 4.7 mM KCl, and 1% BSA) three times. Add 90 ul KRPH containing 100 nM human insulin/vehicle and incubate for 30 min at 37° C. and 5% CO2. Add 10 ul KRPH containing 0.25 uCi 1-[$^3$H]-2-deoxyglucose/well and 50 umol/l 2-deoxyglucose and Incubate 10 min in 95% air/5% CO2 at 37° C. The transport was stopped by rinsing the cells with cold PBS containing 10 mM glucose for three times. The adipocytes were lysed in 50 ul 10% KOH for 5 min. Then the aliquots were subjected to scintillation counting using TriCap. Note: cell differentiation is necessary from 3T3-L1 fibroblasts to 3T3-L1 adipocytes.

Results

Figure 43:
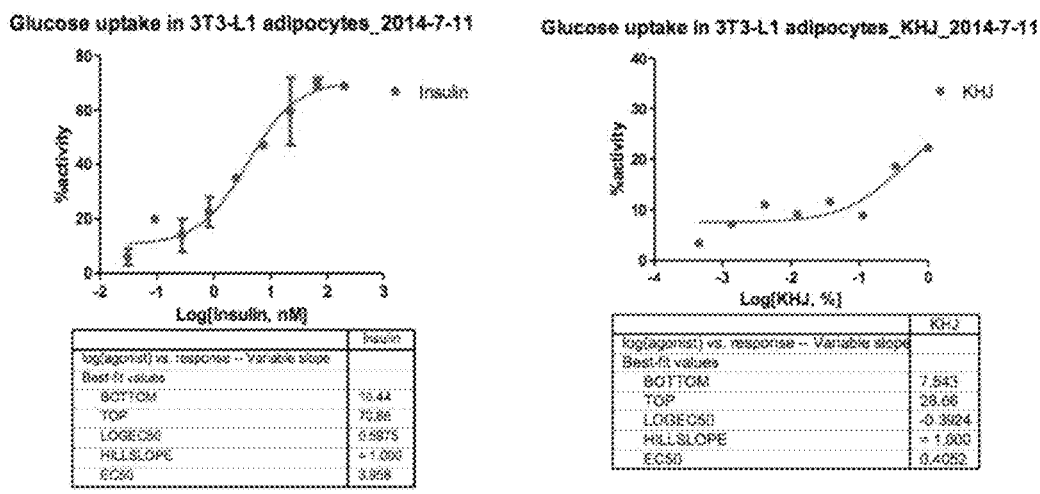
FIG. 43 shows a graph depicting how KUNAMIN™ helps to generate Insulin for Glucose uptake in DIABETICS.

Ten testing proteins were tested in eight concentrations (the starting concentration is 1%, 3 folds dilution) using 3T3-L1 adipocytes in glucose uptake assay (FIGS. 43-45). The assay was conducted twice independently. If the obtained EC50 values from two repeats were not in the 3-fold range of difference, the assay was repeated one more time. Data were analyzed using GraphPad Prism 5.

| Analyzed data: 2014 Jul. 11 | | | | | | | | | | | |
|---|---|---|---|---|---|---|---|---|---|---|---|
| Insulin | | | | HKG | | | | HKB | | | |
| Dose (nM) | Count | | % Activity | | Dose (nM) | Count | | % Activity | | Dose (nM) | Count | | % Activity | |

| Dose (nM) | Count | | % Activity | | Dose (nM) | Count | | % Activity | | Dose (nM) | Count | | % Activity | |
|---|---|---|---|---|---|---|---|---|---|---|---|---|---|---|
| 200 | 980 | 989 | 68% | 70% | 1.00% | 726 | 769 | 12.10% | 21.60% | 1.00% | 672 | 702 | 0.30% | 6.90% |
| 66.67 | 979 | 1000 | 68% | 72% | 0.33% | 816 | 726 | 31.90% | 12.10% | 0.33% | 770 | 763 | 21.80% | 20.20% |
| 22.22 | 887 | 1000 | 47% | 72% | 0.11% | 772 | 764 | 22.20% | 20.50% | 0.11% | 712 | 733 | 9.10% | 13.70% |
| 7.41 | 884 | 992 | 47% | 70% | 0.04% | 720 | 667 | 10.80% | −0.80% | 0.04% | 722 | 779 | 11.2 | 23.80% |
| 2.47 | 736 | 828 | 14% | 35% | 0.01% | 692 | 622 | 4.70% | −10.70% | 0.01% | 636 | 638 | −7.60% | −7.20% |
| 0.82 | 800 | 746 | 28% | 17% | 0.00% | 657 | 646 | −3.00% | −5.40% | 0.00% | 689 | 734 | 4.00% | 13.90% |
| 0.27 | 709 | 761 | 8% | 20% | 0.00% | 725 | 710 | 11.90% | 8.60% | 0.00% | 763 | 723 | 20.20% | 11.50% |
| 0.09 | 760 | 587 | 20% | −18% | 0.00% | 783 | 466 | 24.60% | −44.90% | 0.00% | 801 | 749 | 28.60% | 17.20% |

| KHJ | | | | | KH 103 | | | | | | |
|---|---|---|---|---|---|---|---|---|---|---|---|
| Dose (nM) | Count | | % Activity | | Dose (nM) | Count | | % Activity | | Control | Average |
| 1.00% | 772 | 696 | 22.20% | 5.50% | 1.00% | 696 | 702 | 5.50% | 6.90% | 1078 | 1127 |
| 0.33% | 777 | 734 | 23.30% | 13.90% | 0.33% | 793 | 801 | 26.80% | 28.60% | 1048 | |
| 0.11% | 720 | 703 | 10.80% | 7.10% | 0.11% | 704 | 730 | 7.30% | 13.00% | 1101 | |
| 0.04% | 724 | 723 | 11.70% | 11.50% | 0.04% | 724 | 771 | 11.70% | 22.00% | 1279 | |
| 0.01% | 727 | 698 | 12.30% | 6.00% | 0.01% | 621 | 708 | −10.90% | 8.20% | 699 | 671 |
| 0.00% | 721 | 785 | 11.00% | 25.10% | 0.00% | 724 | 733 | 11.70% | 13.70% | 595 | |
| 0.00% | 743 | 664 | 15.90% | −1.50% | 0.00% | 730 | 679 | 13.00% | 1.80% | 696 | |
| 0.00% | 742 | 631 | 15.60% | −8.70% | 0.00% | 691 | 723 | 4.40% | 11.50% | 692 | |

45

Corresponding dose response curve fits are shown in FIGS. 27, 43, and 56A-E.

| Analyzed data: 2014 Jul. 14 | | | | | | | | | | | |
|---|---|---|---|---|---|---|---|---|---|---|---|
| Insulin | | | | | KH 111 | | | | | KH 601 | | | | |

| Dose (nM) | Count | | % Activity | | Dose | Count | | % Activity | | Dose | Count | | % Activity | |
|---|---|---|---|---|---|---|---|---|---|---|---|---|---|---|
| 200 | 1545 | 1591 | 97% | 106% | 1.0000% | 1224 | 1169 | 38.2% | 28.1% | 1.0000% | 795 | 809 | −40.5% | −37.9% |
| 66.7 | 1364 | 1243 | 64% | 42% | 0.3333% | 1131 | 1046 | 21.1% | 5.5% | 0.3333% | 809 | 955 | −37.9% | −11.2% |
| 22.2 | 1347 | 1362 | 61% | 63% | 0.1111% | 1176 | 1153 | 29.4% | 25.2% | 0.1111% | 1133 | 1126 | 21.5% | 20.2% |
| 7.41 | 1335 | 1238 | 59% | 41% | 0.0370% | 1134 | 1168 | 21.7% | 27.9% | 0.0370% | 1049 | 1143 | 6.1% | 23.3% |
| 2.47 | 1317 | 1191 | 55% | 32% | 0.0123% | 1062 | 1203 | 8.5% | 34.3% | 0.0123% | 1151 | 1073 | 24.8% | 10.5% |
| 0.82 | 1082 | 1083 | 12% | 12% | 0.0041% | 1063 | 1141 | 8.7% | 23.0% | 0.0041% | 1032 | 1004 | 3.0% | −2.2% |
| 0.27 | 1118 | 1018 | 19% | 0% | 0.0014% | 1130 | 1211 | 20.9% | 35.8% | 0.0014% | 1190 | 973 | 31.9% | −7.9% |
| 0.09 | 1033 | 1075 | 3% | 11% | 0.0005% | 1170 | 1190 | 28.3% | 31.9% | 0.0005% | 1081 | 1071 | 12.0% | 10.1% |

| KH 602 | | | | | KH kunakin | | | | | | |
|---|---|---|---|---|---|---|---|---|---|---|---|
| Dose (nM) | Count | | % Activity | | Dose | Count | | % Activity | | Control | Average |
| 1.0000% | 1072 | 1128 | 10.3% | 20.6% | 1.0000% | 1161 | 1069 | 26.6% | 9.8% | 1503 | 1576 |
| 0.3333% | 1114 | 1000 | 18.0% | −2.9% | 0.3333% | 989 | 738 | −4.9% | −51.0% | 1703 | |
| 0.1111% | 1082 | 1091 | 12.1% | 13.8% | 0.1111% | 1050 | 934 | 6.3% | −15.0% | 1587 | |

-continued

| | | | | Analyzed data: 2014 Jul. 14 | | | | | | |
|---|---|---|---|---|---|---|---|---|---|---|
| 0.0370% | 1058 | 1026 | 7.7% | 1.9% | 0.0370% | 990 | 957 | −4.7% | −10.8% | 1510 |
| 0.0123% | 985 | 935 | −5.7% | −14.8% | 0.0123% | 1125 | 978 | 20.0% | −6.9% | 1039 | 1048 |
| 0.0041% | 1097 | 952 | 14.9% | −11.7% | 0.0041% | 1029 | 925 | 2.4% | −16.7% | 1101 |
| 0.0014% | 1051 | 903 | 6.5% | −20.7% | 0.0014% | 1062 | 1055 | 8.5% | 7.2% | 1062 |
| 0.0005% | 1233 | 975 | 39.8% | −7.5% | 0.0005% | 1369 | 1226 | 64.8% | 38.6% | 988 |

Corresponding dose response curve fits are shown in FIGS. 44 and 57A-E.

| | | | | Analyzed data: 2014 Aug. 27 | | | | | | |
|---|---|---|---|---|---|---|---|---|---|---|
| | Insulin | | | | KH 111 | | | | KH 601 | | |
| Dose (nM) | Count | | % Activity | Dose | Count | | % Activity | Dose | Count | | % Activity |
| 200 | 2565 | 2617 | 52% | 59% | 1.0000% | 2538 | 2321 | 49.1% | 22.9% | 1.0000% | 1577 | 1543 | −67.0% | 71.1% |
| 66.7 | 2877 | 2903 | 90% | 93% | 0.3333% | 2319 | 2454 | 22.7% | 39.0% | 0.3333% | 2181 | 2108 | 6.0% | −2.8% |
| 22.2 | 2573 | 2636 | 53% | 61% | 0.1111% | 2773 | 2462 | 77.5% | 39.9% | 0.1111% | 2170 | 2056 | 4.7% | −9.1% |
| 7.41 | 2579 | 2483 | 54% | 42% | 0.0370% | 2510 | 2471 | 45.7% | 41.0% | 0.0370% | 2006 | 2032 | −15.1% | −12.0% |
| 2.47 | 2131 | 2284 | 0% | 18% | 0.0123% | 1678 | 1769 | −54.8% | −43.8% | 0.0123% | 2226 | 1410 | 11.4% | −87.1% |
| 0.82 | 2390 | 2146 | 31% | 2% | 0.0041% | 2276 | 2260 | 17.5% | 15.5% | 0.0041% | 2089 | 2184 | −5.1% | 6.4% |
| 0.27 | 2145 | 2075 | 2% | −7% | 0.0014% | 2169 | 2112 | 4.5% | −2.3% | 0.0014% | 2048 | 2159 | −10.1% | 3.3% |
| 0.09 | 2177 | 2166 | 6% | 4% | 0.0005% | 2339 | 2321 | 25.1% | 22.9% | 0.0005% | 2202 | 2068 | 8.5% | −7.7% |
| 0.03 | 2065 | 2030 | −8% | −12% | | | | | | | | | | |
| 0.01 | 2169 | 2178 | 5% | 6% | | | | | | | | | | |

| | KH 602 | | | | | KH kunakin | | | | | |
|---|---|---|---|---|---|---|---|---|---|---|---|
| Dose (nM) | Count | | % Activity | Dose | Count | | % Activity | Control | Average |
| 1.0000% | 2482 | 2428 | 42.3% | 35.8% | 1.0000% | 2408 | 2371 | 33.4% | 28.9% | 2980 | 2991 |
| 0.3333% | 2250 | 2207 | 14.3% | 9.1% | 0.3333% | 2129 | 2197 | −0.3% | 7.9% | 3078 |
| 0.1111% | 2006 | 2216 | ##### | 10.2% | 0.1111% | 2111 | 1985 | −2.5% | −17.7% | 2959 |
| 0.0370% | 1960 | 2081 | ##### | −6.1% | 0.0370% | 1979 | 2464 | −18.4% | 40.2% | 2945 |
| 0.0123% | 2156 | 2170 | 3.0% | 4.7% | 0.0123% | 1522 | 2323 | −73.6% | 23.1% | 2835 |
| 0.0041% | 2024 | 2095 | ##### | −4.4% | 0.0041% | 2114 | 2158 | −2.1% | 3.2% | 2274 | 2131 |
| 0.0014% | 1975 | 2273 | ##### | 17.1% | 0.0014% | 2185 | 2044 | 6.5% | −10.6% | 2049 |
| 0.0005% | 2207 | 2146 | 9.1% | 1.8%% | 0.0005% | 2293 | 2284 | 19.5% | 18.4% | 2084 |
| | | | | | | | | | | 2157 |
| | | | | | | | | | | 2093 |

Corresponding dose response curve fits are shown in FIGS. 58A-E.

| | | | | Analyzed data: 2014 Aug. 28 | | | | | | |
|---|---|---|---|---|---|---|---|---|---|---|
| | Insulin | | | | KH 410 | | | | KH 601 | | |
| Dose (nM) | Count | | % Activity | Dose | Count | | % Activity | Dose | Count | | % Activity |
| 200 | 2813 | 2574 | 85% | 56% | 1.0000% | 223 | 402 | −223% | −201% | 1.0000% | 837 | 888 | −150% | −144% |
| 66.7 | 2736 | 2827 | 75% | 85% | 0.3333% | 874 | 925 | −145% | −139% | 0.3333% | 1307 | 1390 | −94% | −84% |
| 22.2 | 2812 | 2503 | 84% | 48% | 0.1111% | 1695 | 1961 | −48% | −16% | 0.1111% | 1214 | 1280 | −105% | −97% |
| 7.41 | 2427 | 2442 | 39% | 41% | 0.0370% | 2071 | 2084 | −3% | −2% | 0.0370% | 1773 | 1781 | −39% | −38% |
| 2.47 | 2208 | 2286 | 13% | 22% | 0.0123% | 2076 | 2166 | −3% | 8% | 0.0123% | 2009 | 2040 | −11% | −7% |
| 0.82 | 2111 | 2261 | 1% | 19% | 0.0041% | 2228 | 2245 | 15% | 17% | 0.0041% | 2060 | 2020 | −5% | −9% |
| 0.27 | 2258 | 2306 | 19% | 24% | 0.0014% | 2085 | 2405 | −2% | 36% | 0.0014% | 2087 | 2272 | −2% | 20% |
| 0.09 | 2130 | 2378 | 4% | 33% | 0.0005% | 1994 | 2175 | −13% | 9% | 0.0005% | 2124 | 2049 | 3% | −6% |
| 0.03 | 2281 | 2003 | 21% | −12% | | | | | | | | | | |
| 0.01 | 1918 | 2052 | −22% | −6% | | | | | | | | | | |

| | KH 602 | | | | | KH kunakin | | | | | |
|---|---|---|---|---|---|---|---|---|---|---|---|
| Dose (nM) | Count | | % Activity | Dose | Count | | % Activity | Control | Average |
| 1.0000% | 2483 | 2541 | 45% | 52% | 1.0000% | 2180 | 1998 | 9.5% | −12.1% | 2880 | 2943 |
| 0.3333% | 2345 | 2163 | 29% | 7% | 0.3333% | 2053 | 2065 | −5.6% | −4.2% | 3057 |
| 0.1111% | 2194 | 2250 | 11% | 18% | 0.1111% | 1924 | 2118 | −20.9% | 2.1% | 2758 |
| 0.0370% | 2235 | 2147 | 16% | 6% | 0.0370% | 2108 | 2269 | 0.9% | 20.0% | 2905 |
| 0.0123% | 2103 | 2111 | 0% | 1% | 0.0123% | 2058 | 2061 | −5.0% | −4.6% | 2837 |
| 0.0041% | 1951 | 2043 | −18% | −7% | 0.0041% | 1888 | 2226 | −25.1% | 14.9% | 3221 |

| Analyzed data: 2014 Aug. 28 | | | | | | | | | | |
|---|---|---|---|---|---|---|---|---|---|---|
| 0.0014% | 1966 | 2013 | −16% | −10% | 0.0014% | 1898 | 2403 | −24.0% | 35.9% | 2113 | 2100 |
| 0.0005% | 1973 | 2108 | −15% | 1% | 0.0005% | 2277 | 2411 | 21.0% | 36.9% | 2077 | |
| | | | | | | | | | | 2166 | |
| | | | | | | | | | | 2024 | |

| KH 409 | | | |
|---|---|---|---|
| Dose | Count | | % Activity |
| 1.00000% | 509 | 398 | −189% | −202% |
| 0.3333% | 800 | 1041 | −154% | −126% |
| 0.1111% | 1491 | 1693 | −72% | −48% |
| 0.0370% | 1948 | 2477 | −18% | 45% |
| 0.0123% | 2347 | 2525 | 29% | 50% |
| 0.0041% | 2004 | 2147 | −11% | 6% |
| 0.0014% | 1985 | 2007 | −14% | −11% |
| 0.0005% | 1826 | 2100 | −33% | 0% |

Corresponding dose response curve fits are shown in FIGS. 45 and 59 A-F.

| Analyzed data: 2014 Aug. 29 | | | | | | | | | | | |
|---|---|---|---|---|---|---|---|---|---|---|---|
| Insulin | | | | KH 111 | | | | KH 409 | | | |
| Dose (nM) | Count | | % Activity | | Dose | Count | | % Activity | Dose | Count | | % Activity |
| 200 | 2820 | 2663 | 80% | 62% | 1.0000% | 2093 | 2268 | −4% | 16% | 1.0000% | 455 | 405 | −193% | −199% |
| 66.7 | 2736 | 2660 | 70% | 61% | 0.3333% | 2253 | 2210 | 14% | 9% | 0.3333% | 920 | 837 | −140% | −149% |
| 22.2 | 2633 | 2673 | 58% | 63% | 0.1111% | 2205 | 2174 | 9% | 5% | 0.1111% | 1413 | 1359 | −83% | −89% |
| 7.41 | 2395 | 2466 | 31% | 39% | 0.0370% | 1896 | 2216 | −27% | 10% | 0.0370% | 2023 | 2060 | −12% | −8% |
| 2.47 | 2324 | 7002 | 22% | 563% | 0.0123% | 2153 | 2291 | 3% | 19% | 0.0123% | 2137 | 2164 | 1% | 4% |
| 0.82 | 2069 | 2263 | −7% | 15% | 0.0041% | 2146 | 2019 | 2% | −13% | 0.0041% | 1912 | 2008 | −25% | −14% |
| 0.27 | 2196 | 2340 | 8% | 24% | 0.0014% | 2354 | 2474 | 26% | 40% | 0.0014% | 2318 | 2400 | 22% | 31% |
| 0.09 | 2101 | 2091 | −3% | −4% | 0.0005% | 2416 | 2329 | 33% | 23% | 0.0005% | 2005 | 2200 | −14% | 8% |
| 0.03 | 2039 | 1067 | −10% | −123% | | | | | | | | | | |

| KC 410 | | | | | |
|---|---|---|---|---|---|
| Dose | Count | | % Activity | | Control | | Average |
| 1.0000% | 383 | 526 | −202% | −185% | HC | | |
| 0.3333% | 1018 | 979 | −128% | −133% | 2887 | 3066 | 2996 |
| 0.1111% | 1563 | 1545 | −65% | −67% | 3168 | 3032 | |
| 0.0370% | 1724 | 1882 | −47% | −29% | 2928 | 2892 | |
| 0.0123% | 2001 | 1740 | −15% | −45% | LC | | |
| 0.0041% | 2030 | 1883 | −11% | −28% | 2159 | 1448 | 2130 |
| 0.0014% | 2571 | 2262 | 51% | 15% | 2181 | 2224 | |
| 0.0005% | 1958 | 1804 | −20% | −38% | 2282 | 2483 | |

Corresponding dose response curve fits are shown in FIGS. 60A-D.

CONCLUSION

For insulin reference, get the EC50 5 times.

| | 2014 Jul. 11 | 2014 Jul. 14 | 2014 Aug. 27 | 2014 Aug. 28 | 2014 Aug. 29 |
|---|---|---|---|---|---|
| Insulin EC50 (nM) | 3.958 | 2.464 | 2.535 | 6.944 | 6.66 |

The sample KHG, KGJ and KH602 were tested twice on 3T3-L1 adipocytes glucose uptake assay. They all have activity on 3T3-L1 adipocytes glucose uptake. The results we obtained two times were consistent.

| EC50 | KHG | KHJ | KH 602 |
|---|---|---|---|
| n = 1 | 0.036% | 0.405% | 0.449% |
| n = 2 | 0.014% | 0.828% | 0.199% |

The sample KH409, KH410 and KH601 were tested twice on 3T3-L1 adipocytes glucose uptake assay. They have inhibition effect on 3T3-L1 adipocytes glucose uptake. The results obtained two times were consistent.

| IC50 | KH 409 | KH 410 | KH 601 |
|---|---|---|---|
| n = 1 | 0.192% | 0.250% | 1.481% |
| n = 2 | 0.161% | 0.728% | 0.488% |

The sample KHB, KH103, KH111 and KH Kunakin were tested twice on 3T3-L1 adipocytes glucose uptake assay.

They all have no activity on 3T3-L1 adipocytes glucose uptake assay. The results obtained two times were consistent.

In Vivo Study 3

The Molt-4-luc leukemia model was used to evaluate the anti-cancer efficacy of different compounds in Balb/c nude mice. On day 50 after the cell implantation, the median relative bioluminescence of vehicle group was 153.43 and the positive control group was 1.40; while the KHJ prophylactic group and KHJ therapeutic group produced relative bioluminescence of 2.84 and 1.32, respectively. On day 111 after the cell injection, two mice died and three mice showed bioluminescence signal in vehicle control group. In the positive control group, one mouse died which showed bioluminescence signal. However, in KHJ treatment groups, all mice were alive, and one mouse in the prophylactic group and one mouse in the therapeutic group exhibited bioluminescence signal in this molt-4-luc leukemia model. In summary, the results showed that the test compound of KHJ was well-tolerated by the tumor-bearing mice and the testing article KHJ had inhibition on tumor growth.

The objective was to evaluate the anti-tumor efficacy of different compounds in leukemia model in Balb/c nude mice. All the experiments were conducted in the AAALAC-accredited animal facility in compliance with the protocol approved by the Institutional Animal Care and Use Committee (IACUC).

Experimental Preparations

Female Balb/c nude mice, with a body weight of approximately 20 grams, were obtained from an approved vendor (Shanghai BK Laboratory Animal Co., LTD., Shanghai, China). Upon arrival, animals were assessed as to their general health by a member of a veterinary staff or authorized personnel. Animals were acclimated for at least three days (upon arrival at the experiment room) before being used for the study. Animals were housed in groups during acclimation and individually housed during in-life. The animal room environment was adjusted to the following target conditions: temperature 20-25° C., relative humidity 40-70%, 12 hours of artificial light, and 12 hours dark. Temperature and relative humidity were monitored daily.

All animals had access to Certified Rodent Diet ad libitum. Animals were not fasted prior to the study. Water was autoclaved before provided to the animals ad libitum. Periodic analyses of the water were performed and the results were archived at WuXi AppTec. There were no known contaminants in the diet or water which, at the levels detected expected to interfere with the purpose, conduct or outcome of the study.

Cell Culture

The Molt-4-luc (Vendor link: Caliper-125057) tumor cells were maintained in vitro as a suspension culture in RPMI 1640 medium supplemented with 10% fetal bovine serum at 37° C. in an atmosphere of 5% CO2 in air. The tumor cells were routinely subcultured twice weekly. The cells growing in an exponential growth phase were harvested and counted for tumor inoculation.

The testing articles (KH51, KHJ, KHR, KH103, KH111, KH606, KH610, KHJ2, KHJ3, KHJC and KH103C) were provided by RAAS. Cyclophosphamide (Shanxi Powerdone Pharmaceutical CO. LTD.; Lot. #04120503) was formulated in saline.

Experimental Protocol

Mice were randomly assigned to 16 groups (vehicle control, positive control, and 14 testing article groups) based on the body weight. Mice in the prophylactic group were administered with testing articles four weeks before tumor implantation according to Table 13. Mice in the vehicle, the positive control, and the therapeutic groups were administered with testing articles right after cell injection according to Table 18. Whole body and metastatic bioluminescence were measured and recorded.

TABLE 18

| | | Experimental Design | | | |
|---|---|---|---|---|---|
| Group | Treatment | Dosage and dosing volume | Dosing Route | Dosing Schedule | Animal Number |
| 1 | Vehicle | — | Free to drink | — | 6 |
| 2 | Positive control: Cyclophosphamide | 100 mpk for the first dose, 75 mpk for the following doses. | IP | BIW | 6 |
| 3 | KH51 (Prophylactic group*) | 20 ml/kg | IP | QD | 6 |
| 4 | KH51 (Therapeutic group**) | 20 ml/kg | IP | QD | 6 |
| 5 | KHJ (Prophylactic group*) | — | Free to drink | — | 6 |
| 6 | KHJ (Therapeutic group**) | — | Free to drink | — | 6 |
| 7 | KHR (Prophylactic group*) | — | Free to drink | 24 h on (D0-D38)$^a$ 8 h on 16 h off (D39-D44)$^a$ 16 h on 8 h off (D45-end)$^a$ | 6 |

TABLE 18-continued

Experimental Design

| Group | Treatment | Dosage and dosing volume | Dosing Route | Dosing Schedule | Animal Number |
|---|---|---|---|---|---|
| 8 | KHR (Therapeutic group**) | — | Free to drink | 24 h on (D28-38)$^a$ 8 h on 16 h off (D39-D44)$^a$ 16 h on 8 h off (D45-end)$^a$ | 6 |
| 9 | KH103 (Prophylactic group*) | — | Free to drink | — | 6 |
| 10 | KH103 (Therapeutic group**) | — | Free to drink | — | 6 |
| 11 | KH111 (Prophylactic group*) | — | Free to drink | — | 6 |
| 12 | KH111 (Therapeutic group**) | — | Free to drink | — | 6 |
| 13 | KH609 (Prophylactic group*) | — | Free to drink | — | 6 |
| 14 | KH609 (Therapeutic group**) | — | Free to drink | — | 6 |
| 15 | KH610 (Prophylactic group*) | — | Free to drink | — | 6 |
| 16 | KH610 (Therapeutic group**) | — | Free to drink | — | 6 |

Note:
*Prophylactic group: six mice, free access to drink the test sample, the test sample was given four weeks before cell injection.
**Therapeutic group: six mice, free access to drink the test sample, the test sample was given right after cell injection.
Vehicle, positive control groups: treatment was given right after cell injection.

TABLE 19

The treatment of animals with signal

| | | Treatment of mice with signal$^b$ | | | |
|---|---|---|---|---|---|
| Group | D46-D51$^a$ | D52$^a$ | D53-D59$^a$ | D60-92$^a$ | D93-D111$^a$ |
| 1 Vehicle | Vehicle | Vehicle | Vehicle | Vehicle | Vehicle |
| 2 Positive control: Cyclophosphamide | Cyclophosphamide | Cyclophosphamide | Cyclophosphamide | Cyclophosphamide | Cyclophosphamide |
| 3 KH51 (Prophylactic group*) | KHJ | KHJ1 + KH51 | KHJ1 | KHJC | KHJ |
| 4 KH51 (Therapeutic group**) | KHJ | KHJ1 + KH51 | KHJ1 | KHJC | KHJ |
| 5 KHJ (Prophylactic group*) | KHJ | KHJ1 + KH51 | KHJ1 | KHJC | KHJC |
| 6 KHJ (Therapeutic group**) | KHJ | KHJ1 + KH51 | KHJ1 | KHJC | KHJC |
| 7 KHR (Prophylactic group*) | KHJ | KHJ1 + KH51 | KHJ1 | KH103C | KHJ |
| 8 KHR (Therapeutic group**) | KHJ | KHJ1 + KH51 | KHJ1 | KH103C | KHJ |
| 9 KH103 (Prophylactic group*) | KHJ | KHJ2 + KH51 | KHJ2 | KH103C | KHJ |
| 10 KH103 (Therapeutic group**) | KHJ | KHJ2 + KH51 | KHJ2 | KHJC + KH103C | KHJ |

TABLE 19-continued

The treatment of animals with signal

| | | Treatment of mice with signal[b] | | | |
|---|---|---|---|---|---|
| Group | D46-D51[a] | D52[a] | D53-D59[a] | D60-92[a] | D93-D111[a] |
| 11 KH111 (Prophylactic group*) | KHJ | KHJ2 + KH51 | KHJ2 | KHJC + KH103C | KHJC + KH103C |
| 12 KH111 (Therapeutic group**) | KHJ | KHJ2 + KH51 | KHJ2 | KHJC + KH103C | KHJ |
| 13 KH609 (Prophylactic group*) | KHJ | KHJ2 + KH51 | KHJ3 | KHJ3 | KHJ |
| 14 KH609 (Therapeutic group**) | KHJ | KHJ2 + KH51 | KHJ3 | KHJ3 | KHJ |
| 15 KH610 (Prophylactic group*) | KHJ | KHJ2 + KH51 | KHJ3 | KHJ3 | KHJ |
| 16 KH610 (Therapeutic group**) | KHJ | KHJ2 + KH51 | KHJ3 | KHJ3 | KHJ |

Note:
[a]Days after the cell injection
[b]The doses were changed during the experiment as requested by the sponsor.
*Prophylactic group: six mice, free access to drink the test sample, the test sample was given four weeks before cell injection.
**Therapeutic group: six mice, free access to drink the test sample, the test sample was given right after cell injection.
Vehicle, positive control groups: treatment was given right after cell injection.

Bioluminescence Measurements

The inoculated mice were weighted and intraperitoneally injected luciferin at 150 mg/kg. After 10 minutes of the luciferin administration, the animals were pre-anesthetized with the mixture gas of oxygen and isoflurane. When the animals were in a complete anesthetic state, they were moved into the imaging chamber for bioluminescence measurements with IVIS (Lumina II). The bioluminescence of the whole animal body, including primary and metastatic tumors, was measured and images are recorded.

Drugs and Materials

The test compounds (KH51, KHJ, KHR, KH103, KH111, KH606, KH610, KHJ2, KHJ3, KHJC and KH103C) were provided by RAAS. Cyclophosphamide (ShanXi Powerdone Pharmaceutical CO. LTD.; Lot. #04120503).

Data Analysis: median relative bioluminescence

Bioluminescence (BL) of the whole animal body, including primary and metastatic tumors, was measured and images were recorded using a fixed intensity scale. Relative bioluminescence (RBL) value was calculated with IVIS Lumina II software and the data was recorded. Tumor growth curve was plotted with median relative bioluminescence.

$RBL = RBL_t/RBL_0$, where $RBL_t$—RBL value at time t
$RBL_0$—RBL value at starting time Data Analysis: Survival Animals and Animals with Signal of Cancer Animals were kept receiving bioluminescent measurement once a week until Day 111 after the cell injection. The bioluminescence of the whole animal body, including primary and metastatic tumors, was measured. The survival animals and animals with signal of cancer were recorded.

Results: Median Relative Bioluminescence in Different Groups

Figure 46:
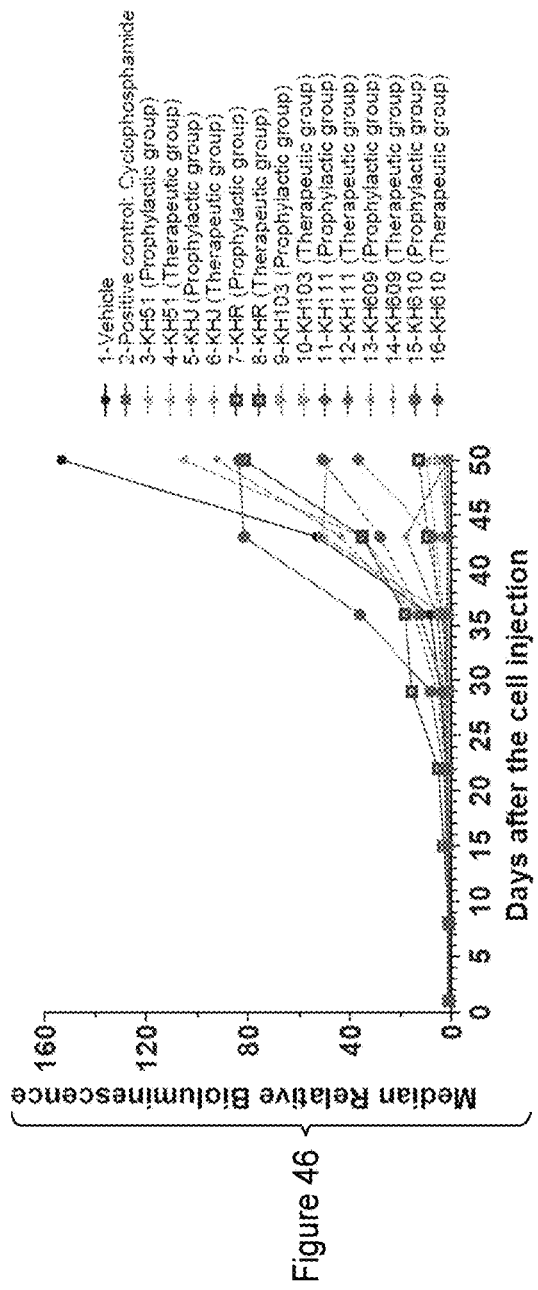
FIG. 46 shows a graph depicting median relative bioluminescence for the vehicle, positive control, and the other 14 items tested, including the KHJ609, KHJ610, and KHJ (the code names for KUNAMIN™). All the test items slowed down the growth of the Leukemia cancer cells and all are below the vehicle Median Relative Bioluminescence.

On day 50 after the cell implantation, the median relative bioluminescence of the vehicle group was 153.43 and the positive control group was 1.40, while the KHJ prophylactic group and KHJ therapeutic group produced relative bioluminescence of 2.84 and 1.32, respectively. The results showed that the testing article KHJ had inhibition on tumor growth. The median relative bioluminescence of different groups is shown in FIG. 46.

Results: Survival Animals and Animals with Signal of Cancer

Animals kept receiving bioluminescent measurement once a week until Day 111 after the cell injection. The bioluminescence of the whole animal body, including primary and metastatic tumors, was measured. The survival animals and animals with signs of cancer were recorded. On day 111 after the cell injection, two mice died and three mice showed bioluminescence signals in the vehicle control group. In the positive control group, one mouse died which showed bioluminescence signal. However, in the KHJ treatment groups, all mice were alive, and one mouse in prophylactic group and one mouse in therapeutic group exhibited bioluminescence signal in this Molt-4-luc leukemia model.

The survival animals and animals with signal of cancer were shown in Table 20.

TABLE 20

Summary on day 111 after the cell injection

| Group | Treatment | Animal Number | Animals # with bioluminescence signal | Survival animals # |
|---|---|---|---|---|
| 1 | Vehicle | 6 | 3 | 4 |
| 2 | Positive control: Cyclophosphamide | 6 | 1 | 5 |
| 3 | KH51 (Prophylactic group*) | 6 | 4 | 3 |
| 4 | KH51 (Therapeutic group**) | 6 | 3 | 5 |

TABLE 20-continued

Summary on day 111 after the cell injection

| Group | Treatment | Animal Number | Animals # with bioluminescence signal | Survival animals # |
|---|---|---|---|---|
| 5 | KHJ (Prophylactic group*) | 6 | 1 | 6 |
| 6 | KHJ (Therapeutic group**) | 6 | 1 | 6 |
| 7 | KHR (Prophylactic group*) | 6 | 4 | 2 |
| 8 | KHR (Therapeutic group**) | 6 | 2 | 5 |
| 9 | KH103 (Prophylactic group*) | 6 | 3 | 4 |
| 10 | KH103 (Therapeutic group**) | 6 | 1 | 5 |
| 11 | KH111 (Prophylactic group*) | 6 | 2 | 6 |
| 12 | KH111 (Therapeutic group**) | 6 | 2 | 4 |
| 13 | KH609 (Prophylactic group*) | 6 | 3 | 5 |
| 14 | KH609 (Therapeutic group**) | 6 | 4 | 4 |
| 15 | KH610 (Prophylactic group*) | 6 | 4 | 4 |
| 16 | KH610 (Therapeutic group**) | 6 | 4 | 4 |

Note:
*Prophylactic group: six mice, free access to drink the test sample, the test sample was given four weeks before the cell injection.
**Therapeutic group: six mice, free access to drink the test sample, the test sample was given right after the cell injection.
Vehicle, positive control groups: treatment was given right after the cell injection.

A molt-4-luc leukemia model was used to evaluate the anti-cancer efficacy of different compounds in Balb/c nude mice. On day 50 after the cell implantation, the median relative bioluminescence of the vehicle group was 153.43 and the positive control group was 1.40, while the KHJ prophylactic group and the KHJ therapeutic group produced relative bioluminescence of 2.84 and 1.32, respectively.

On day 111 after the cell injection, two mice died and 3 mice showed bioluminescence signal in the vehicle control group. In the positive control group, one mouse died which showed bioluminescence signal. However, in the KHJ treatment groups, all mice were alive, and one mouse in prophylactic group and one mouse in therapeutic group exhibited bioluminescence signal in this molt-4-luc leukemia model. The reasons for the death of the mice may be the tumor growth. Here, the mice which showed bioluminescence died. It means that the tumor growth is the dominant reason leading to the death of the mice. Note: one mouse (⅙) in KH609 prophylactic group died on day 44 after the cell injection. GraphPad Prism 5 was used for graph preparation.

The results showed that the testing article KHJ had inhibition on tumor growth. In the study of KH609 and KH610 vs Leukemia cancer, it was found that KH609 and KH610 helped to slow the growth of the Leukemia cancer cells.

Among the items tested, included were KHJ609, KHJ610, and KHJ, the code names for Kunamin™. As shown in FIG. 46, all the test items have slowed down the growth of the Leukemia cancer cells and all are below the vehicle Median Relative Bioluminescence.

Figure 47:
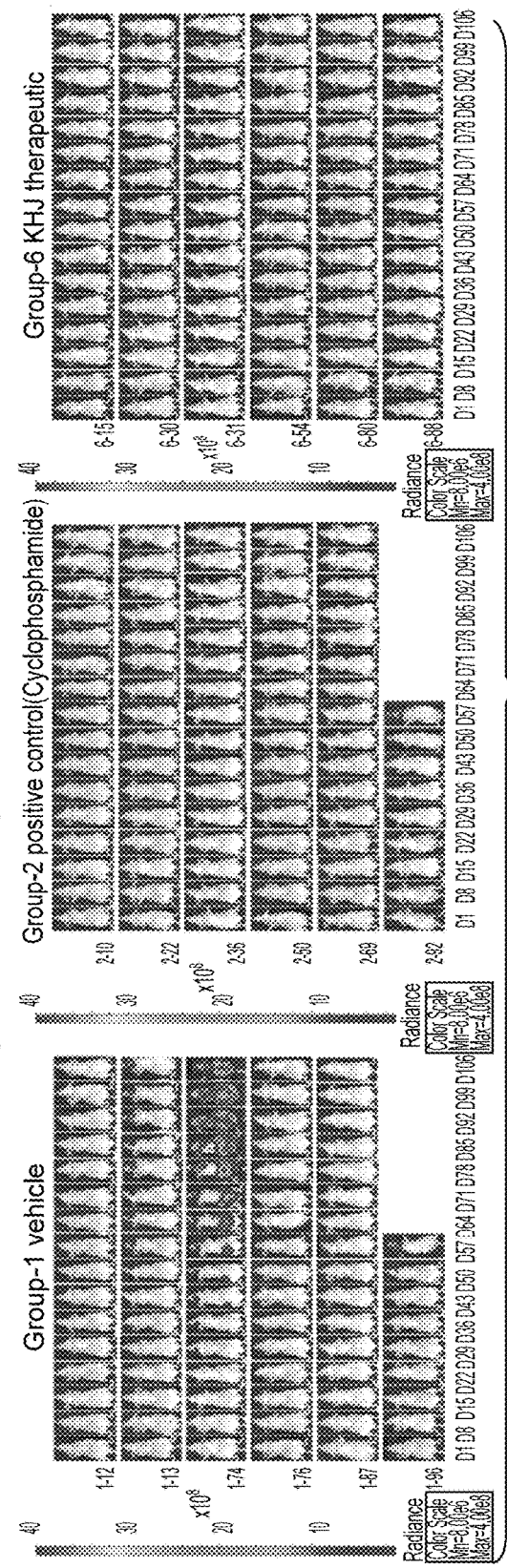
FIG. 47 shows images of bioluminescence of the KHJ Therapeutic group.

In the KHJ Therapeutic group (FIG. 47) none of the mice died until day 106, and none of them has shown a median relative bioluminescence in comparison with the vehicle group. Three of them have developed Leukemia and one died at day 57. Also to compare with the positive group, which used a drug, one mouse in the positive group died at day 57 as well. Due to the fact that the three mice in the vehicle did not grow the Leukemia, CRO has been requested to inject 20 million more Leukemia cells into those three mice in the vehicle, as well as all six mice in the KHJ until day 150. All mice in the vehicle group as well as the positive control group died. Mice in the KHJ group continued to live up to 280 days.

Figure 48:
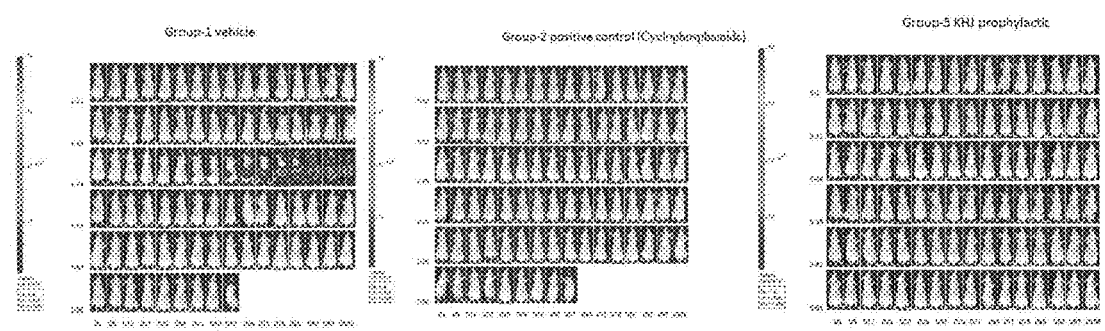
FIG. 48 shows images of bioluminescence of the KHJ Prophylactic group.
Figure 49:
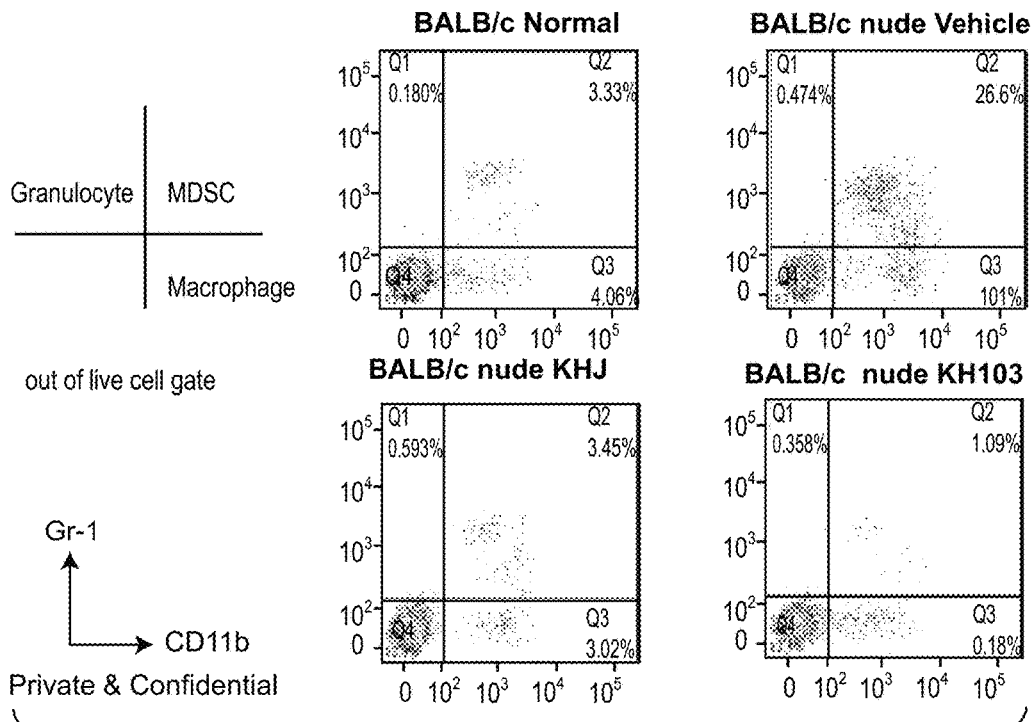
FIG. 49 shows graphs depicting decreased MDSC cell percentage in the Peripheral blood of KHJ and KH103 treated mice.
Figure 50:
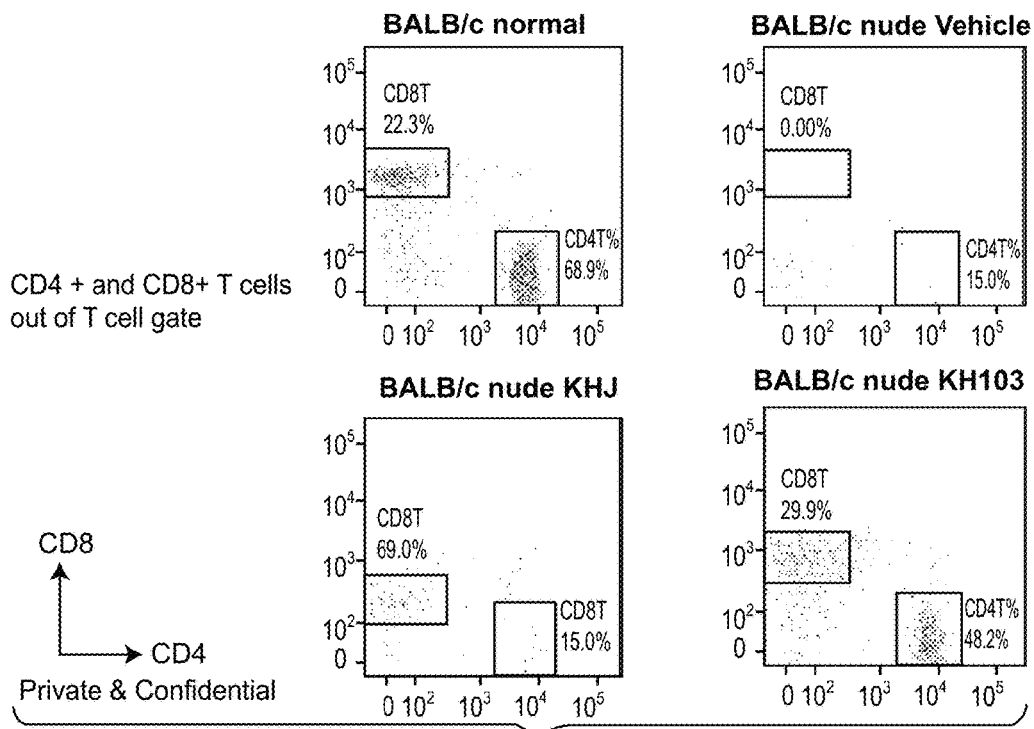
FIG. 50 shows graphs depicting increased percentage of CD4+ and CD8+ T lymphocyte in spleen of KHJ and KH103 treated mice.
Figure 51:
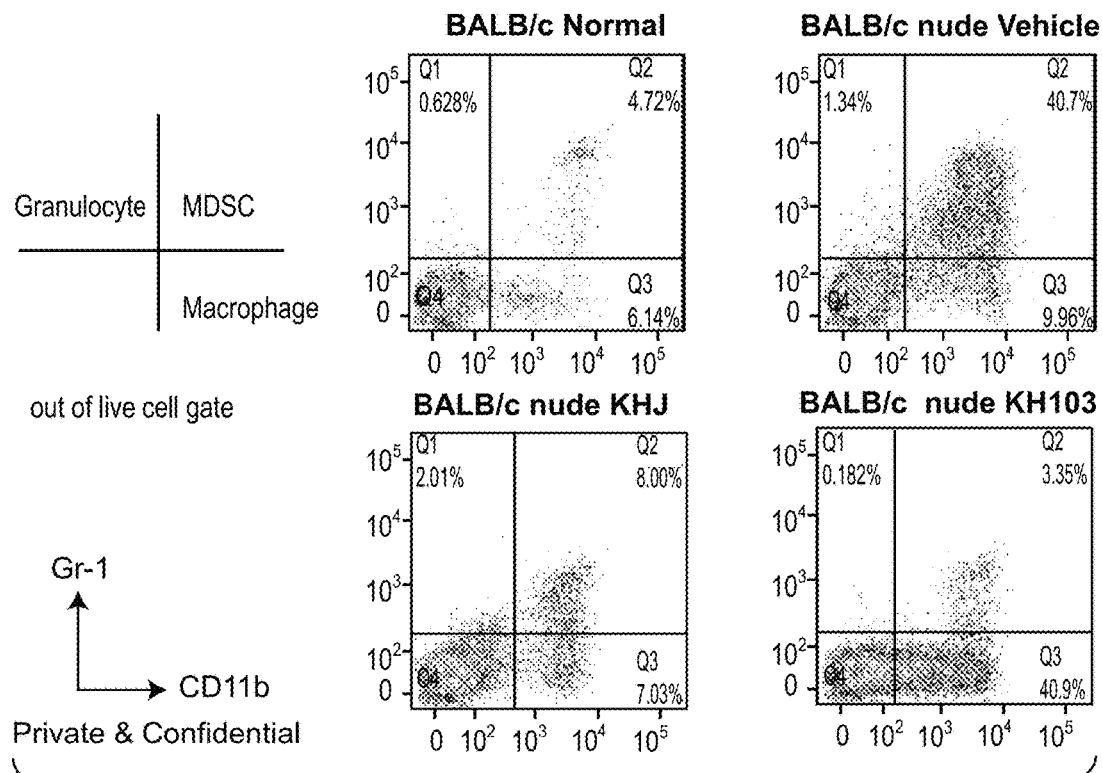
FIG. 51 shows graphs depicting decreased MDSC cell percentage in the spleen of KHJ and KH103 treated mice.
Figure 52:
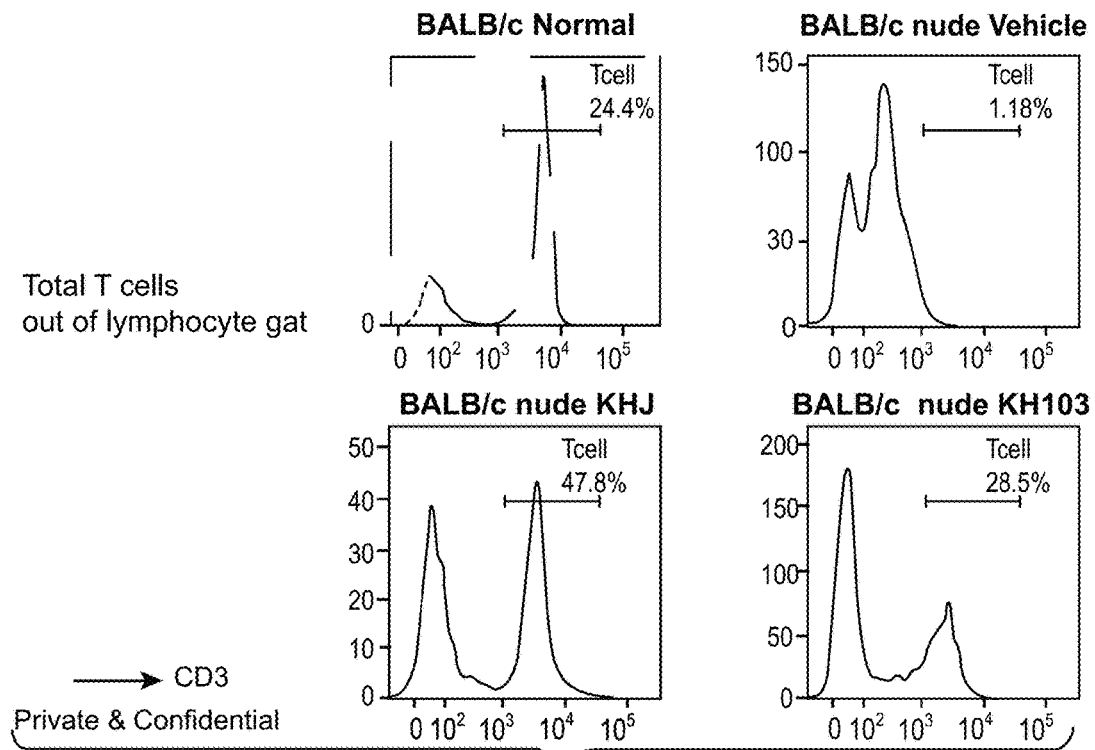
FIG. 52 shows graphs depicting increased percentage of lymophocyte in lymph node of KHJ and KH103 treated mice.
Figure 53:
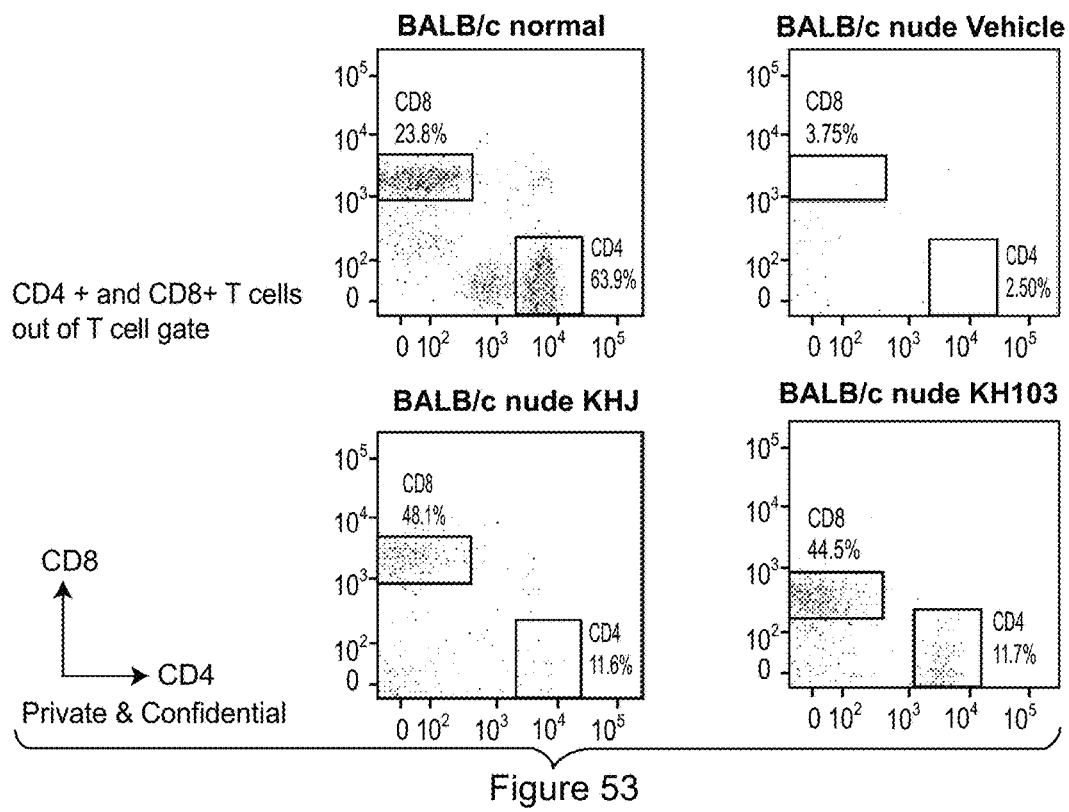
FIG. 53 shows graphs depicting increased percentage of CD4+ and CD8+T lymophocyte in lymph node of KHJ and KH103 treated mice.

In the KHJ Prophylactic group (FIG. 48) none of the mice died until day 106. One mouse (5-53) showed a median relative bioluminescence, and the signal has become weaker thanks to the help of KHJ in converting Leukemia cancer cells into KH good healthy cells (from human, from plant and from animal). In comparison with the vehicle group, three mice developed Leukemia and one died at day 57. Also to compare with the positive group, which used a drug, one mouse in the positive group died at day 57 as well. Due to the fact that the three mice in the vehicle did not grow the Leukemia, the CRO was requested to inject 20 million more Leukemia cells into those three mice in the vehicle as well as all six mice in the KHJ in both groups (prophylactic and therapeutic) until day 150. All mice in the vehicle group as well as the positive control group died. Mice in the KHJ continued to live up to 300 days.

In conclusion, KUNAMIN™ has zero percent concentration of the juice. With higher concentration, more cells will be generated and it will be more efficacious in preventing and treating leukemia.

In Vivo Study 4

The in vivo anti-tumor efficacy of KHJ, KH103, and KHGD in the subcutaneous MDA-MB-436 human breast cancer model in female BALB/c nude mice was evaluated.

Groups for prophylactic arms are shown in Table 21. Groups for therapeutic arms are shown in Table 22.

TABLE 21

Groups for prophylactic arms

| Group | n | Treatment | Dose (mg/kg) | Dosing Route | Dosing volume | Schedule |
|---|---|---|---|---|---|---|
| 1 | 10 | Vehicle - prophylactic | — | Free to drink + p.o. | — | Detailed in the note |
| 2 | 10 | KHJ - prophylactic | — | Free to drink + p.o. | — | Detailed in the note |
| 3 | 10 | KH103 - prophylactic | — | Free to drink + p.o. | — | Detailed in the note |

TABLE 21-continued

Groups for prophylactic arms

| Group | n | Treatment | Dose (mg/kg) | Dosing Route | Dosing volume | Schedule |
|---|---|---|---|---|---|---|
| 4 | 10 | KHGD - prophylactic | — | Free to drink + p.o. | — | Detailed in the note |

Note:
Dosing schedule (Days after inoculation, the minus signs before day number represents days before inoculation)
Group 1: Free to drink sterilized water.
Group 2: Day −13 to Day 52: Free to drink KHJ only. Day 53 to Day 57: Free to drink KHJ along with KHJA 4 times gavage per day with 3 h intervals, 0.4 mL each time. Day 58 to Day 61: Free to drink KHJ only. Day 62 to Day 72: Free to drink KHJ along with KHJA 4 times gavage per day with 3 h intervals, 0.4 mL each time.
Group 3: Day −13 to Day 50: Free to drink KH103 only. Day 51 to Day 72: Free to drink KH103 along with KH103 (150 mg/ml) 4 times gavage per day with 3 h intervals, 0.4 mL each time.
Group 4: Day −13 to Day −11: Free to drink KHGD along with KHGD 3 times gavage per day with 4 h intervals, 0.4 mL each time. Day −10 to Day 32: Free to drink KHGD 8 h on/16 h off along with KHGD 3 times gavage per day with 4 h intervals, 0.4 mL each time. Day 33 to Day 52: Free to drink KHGD 16 h on/8 h off along with KHGD 4 times gavage per day with 3 h intervals, 0.4 mL each time. Day 53 to Day 57: Free to drink KHGD 16 h on/8 h off along with KHGold 4 times gavage per day with 3 h intervals, 0.4 mL each time. Day 58 to Day 61: Free to drink KHGD 16 h on/8 h off only. Day 62 to Day 72: Free to drink KHGD 16 h on/8 h off along with KHGold 4 times gavage per day with 3 h intervals, 0.4 mL each time.

TABLE 22

Groups for therapeutic arms

| Group | n | Treatment | Dose (mg/kg) | Dosing Route | Dosing volume | Schedule |
|---|---|---|---|---|---|---|
| 5 | 10 | Vehicle - therapeutic | — | Free to drink + p.o. | — | Detailed in the note |
| 6 | 10 | Paclitaxel | 15 | i.p. | 10 uL/g | BIW |
| 7 | 10 | KHJ - therapeutic | — | Free to drink + p.o. | — | Detailed in the note |
| 8 | 10 | KH103 - therapeutic | — | Free to drink + p.o. | — | Detailed in the note |
| 9 | 10 | KHGD - therapeutic | | Free to drink + p.o. | | |

Note:
Dosing schedule (Days after inoculation)
Group 5: Free to drink sterilized water.
Group 6: i.p. twice per week.
Group 7: Day 9 to Day 52: Free to drink KHJ only. Day 53 to Day 57: Free to drink KHJ along with KHJA 4 times gavage per day with 3 h intervals, 0.4 mL each time. Day 58 to Day 61: Free to drink KHJ only. Day 62 to Day 72: Free to drink KHJ along with KHJA 4 times gavage per day with 3 h intervals, 0.4 mL each time.
Group 8: Day 9 to Day 50: Free to drink KH103 only. Day 51 to Day 72: Free to drink KH103 along with KH103 (150 mg/ml) 4 times gavage per day with 3 h intervals, 0.4 mL each time.
Group 9: Day 9 to Day 32: Free to drink KHGD 8 h on/16 h off along with KHGD 3 times gavage per day with 4 h intervals, 0.4 mL each time. Day 33 to Day 52: Free to drink KHGD 16 h on/8 h off along with KHGD 4 times gavage per day with 3 h intervals, 0.4 mL each time. Day 53 to Day 57: Free to drink KHGD 16 h on/8 h off along with KHGold 4 times gavage per day with 3 h intervals, 0.4 mL each time. Day 58 to Day 61: Free to drink KHGD 16 h on/8 h off only. Day 62 to Day 72: Free to drink KHGD 16 h on/8 h off along with KHGold 4 times gavage per day with 3 h intervals, 0.4 mL each time.

Animals and Housing Condition

The animals used were of the species *Mus musculus*, strain BALB/c nude, age 6-8 weeks, and female. The body weight was 18-22 g. The number of animals was 90 mice, plus spare. The animal supplier was Shanghai BK Laboratory Animal Co., LTD.

The mice were kept in individual ventilation cages at constant temperature and humidity with 5 animals in each cage. The temperature was 20-26° C. and the humidity was 40-70%. The cages were made of polycarbonate and had a size of 300 mm×200 mm×180 mm. The bedding material was corn cob, which was changed twice per week.

For a diet, the animals had free access to irradiation sterilized dry granule food during the entire study period. The animals had free access to sterile drinking water.

The identification labels for each cage contained the following information: number of animals, sex, strain, date received, treatment, study number, group number, and the starting date of the treatment. Animals were marked for identification by ear coding.

Testing and Positive Control Articles Testing article KHJ was manufactured by RAAS, was liquid, and was packed as 500 ml/vial and stored at 4° C.

Testing article KH103 was manufactured by RAAS, was liquid, and was packed as 500 ml/vial and stored at 4° C.

Testing article KHGD was manufactured by RAAS, was liquid, and was packed as 500 ml/vial and stored at 4° C.

Testing article KHJA was manufactured by RAAS, was liquid, and was packed as 500 ml/vial and stored at 4° C.

Testing article KH103 powder was manufactured by RAAS, was a white powder, and was packed as 500 g/package and stored at room temperature.

Testing article KHGold was manufactured by RAAS, was liquid, and was packed as 500 ml/vial and stored at 4° C.

Positive control agent Paclitaxel was manufactured by Yangtze River Pharmaceutical Group, lot number 13092811, was a light-yellow solution, and was packed as 5 ml: 30 mg/vial and stored at room temperature.

EXPERIMENTAL METHODS AND PROCEDURES

Cell Culture

The MDA-MB-436 tumor cells (ATCC, Manassas, Va., cat# HTB-130) were maintained in vitro as a monolayer culture in L-15 medium supplemented with 10% fetal bovine serum, 10 ug/ml insulin, 16 ug/ml glutathione, 100 U/ml penicillin and 100 ug/ml streptomycin at 37° C. in an atmosphere of 5% CO2 in air. The tumor cells were routinely subcultured twice weekly by trypsin-EDTA treatment. The cells growing in an exponential growth phase were harvested and counted for tumor inoculation.

Tumor Inoculation

Each mouse was inoculated subcutaneously at the right flank with MDA-MB-436 tumor cells ($1\times10^7$) in 0.1 ml of PBS supplemented with BD Matrigel (1:1) for tumor development. The prophylactic treatments were started 13 days before inoculation. The therapeutic treatments were started on day 9 after tumor inoculation when the average tumor size reached approximately 81 mm$^3$. Each group consisted of 10 tumor-bearing mice. The testing article was administrated to the mice according to the predetermined regimen as shown in the experimental design Table 21 (prophylactic) and Table 22 (therapeutic).

Testing Article Preparation

Tumor Measurements

The major endpoint was to see if the tumor growth could be delayed or mice could be cured. Tumor size was measured twice weekly in two dimensions using a caliper, and the volume was expressed in mm$^3$ using the formula: $V=0.5 a\times b^2$ where a and b are the long and short diameters of the tumor, respectively. The tumor size was then used for calculations of both T-C and T/C values. T-C was calculated with T as the time (in days) required for the mean volume of treatment group tumors to reach 600 mm$^3$, and C as the time (in days) for the mean volume of control group tumors to reach the same size. The T/C value (in percent) is an indication of antitumor effectiveness; T and C are the mean volumes of the treated and control groups, respectively, on a given day.

$\Delta$TGI was calculated for each group using the formula: $\Delta TGI\ (\%)=[1-(Ti-T0)/(Vi-V0)]\times 100$; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Tumor pictures were taken and tumor weight was measured at the study termination. T/C$_{weight}$ value (in percent) was calculated using the formula: T/C$_{weight}$%=T$_{weight}$/C$_{weight}\times 100\%$ where T$_{weight}$ and C$_{weight}$ were the mean tumor weights of the treated and vehicle control groups, respectively.

TABLE 23

Test Article Formulation Preparation

| Compounds | Package | Preparation | Concentration (mg/ml) | Storage |
| --- | --- | --- | --- | --- |
| Vehicle | — | — | — | RT |
| KHJ | 500 ml/vial | Ready to use | — | 4° C. |
| KHJA | 500 ml/vial | Ready to use | — | 4° C. |
| KH103 | 500 ml/vial | Ready to use | — | 4° C. |
| KH103 | 500 g/package | Precisely weigh out 18,000 mg KH103 powder into a sterile glass bottle containing a magnetic stirrer; add 80% of target volume of double-distilled water and sitr at room temperature until a homogenous solution was formulated, QS to the target volume (120 ml) with double-distilled water. | 150 | 4° C. |
| KHGD | 500 ml/vial | Ready to use | — | 4° C. |
| KHGold | 500 ml/vial | Ready to use | — | 4° C. |
| Paclitaxel | 5 ml:30 mg/vial | Dilute 1.5 ml of 6 mg/ml Paclitaxel with 4.5 ml vehicle to make a 1.5 mg/ml solution. Mix thoroughly. | 1.5 | 4° C. |

All the procedures related to animal handling, care and treatment in the study were performed according to the guidelines approved by the Institutional Animal Care and Use Committee (IACUC) of WuXi AppTec following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured twice weekly), eye/hair matting and any other abnormal effect as stated in the protocol. Death and observed clinical signs were recorded on the basis of the numbers of animals within each subset.

Summary statistics, including mean and the standard error of the mean (SEM), are provided for the tumor volume of each group at each time point.

Statistical analyses of differences in tumor volume and tumor weight among the groups were conducted on the data obtained when the average tumor volume of vehicle-therapeutic group reached 2,000 mm$^3$ (Day 71 after inoculation).

One-way ANOVA was performed to compare tumor volume and tumor weight among groups, and when a significant F-statistics (a ratio of treatment variance to the error variance) was obtained, comparisons between groups were carried out with Dunnett t-tests. All data were analyzed using SPSS 19.0. p<0.05 was considered to be statistically significant.

Mortality, Morbidity, and Body Weight Gain or Loss

Figure 54A:
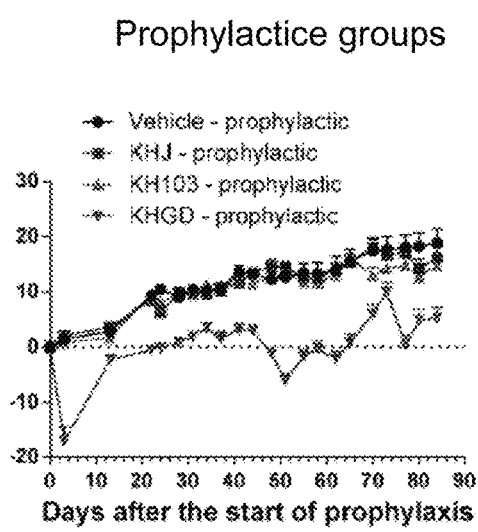
FIG. 54A-B show plots depicting percent body weight (BW) change of prophylactic and therapeutic groups. BW change was calculated based on animal weight on the first day of dosing. Data points represent group mean percent change in BW. Error bars represent standard error of the mean (SEM).
Figure 54B:
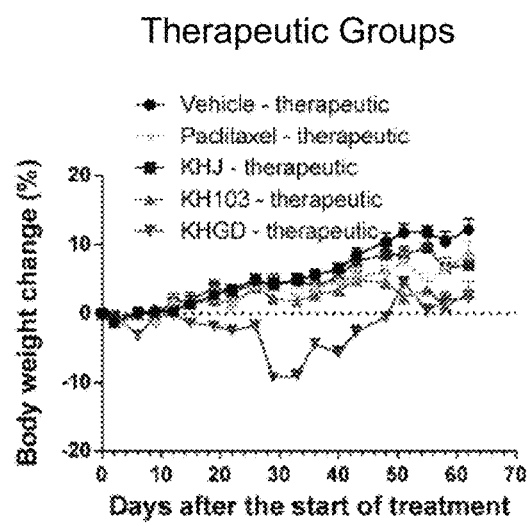
Figure 56B:
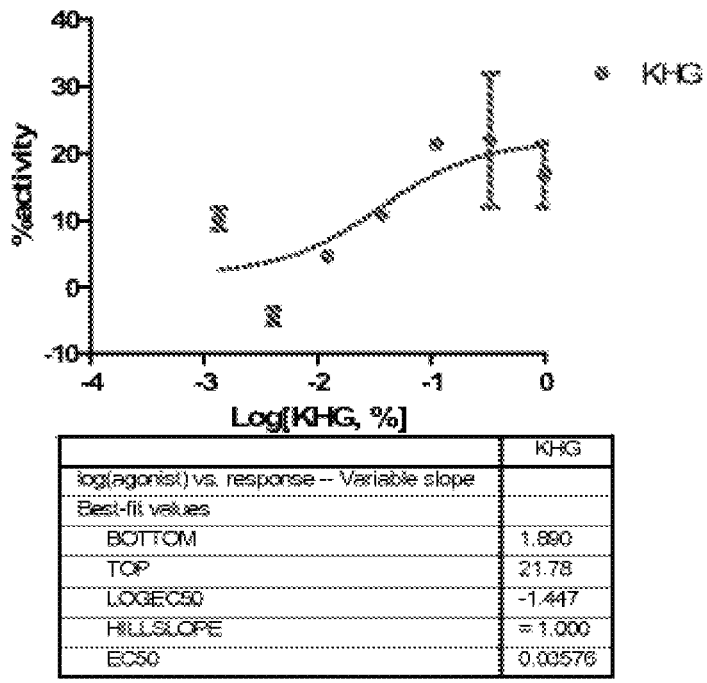
Figure 56C:
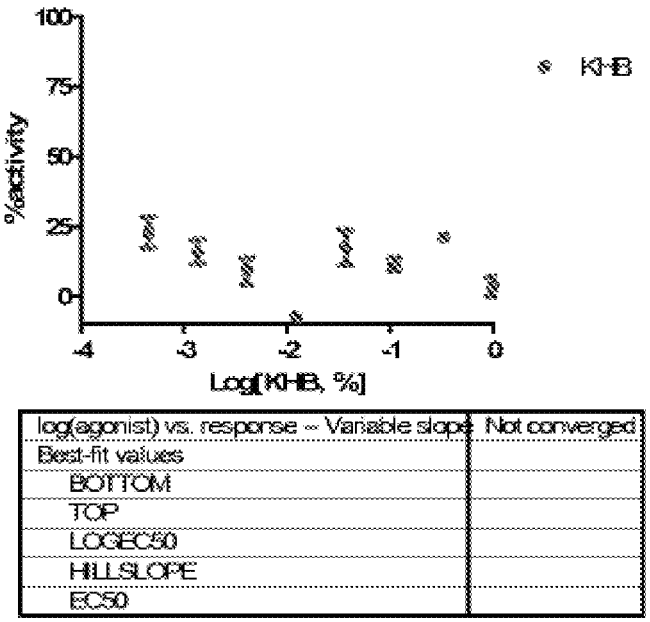
Figure 56D:
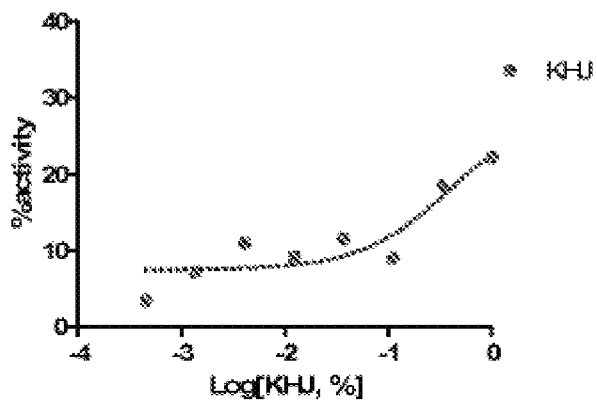
Figure 56E:
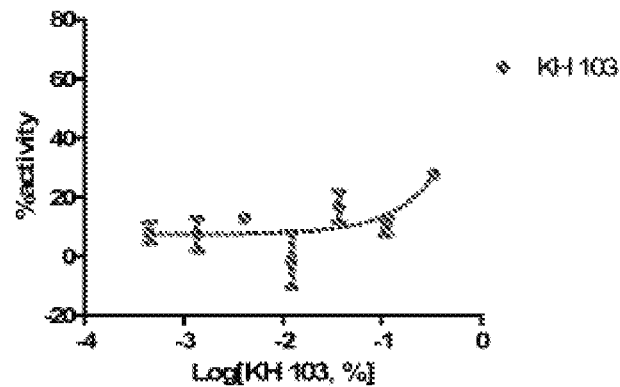
Figure 57A:
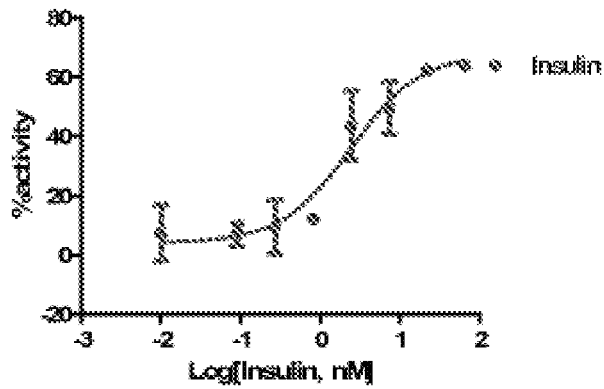
FIG. 57A-E show dose response curve fits for glucose uptake in 3T3-L1 adipocytes for insulin, KH111, KH601, KH602, and KH kunamin.
Figure 57B:
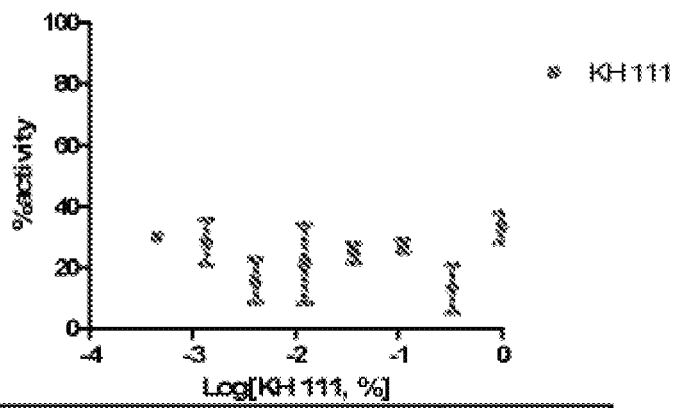
Figure 57C:
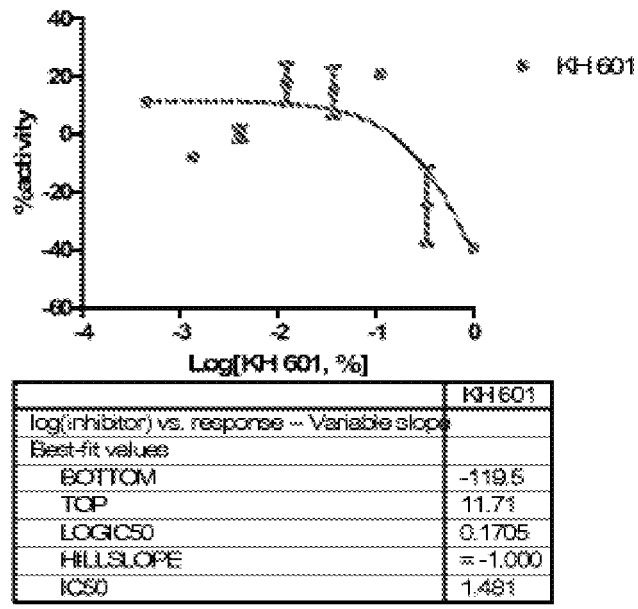
Figure 57D:
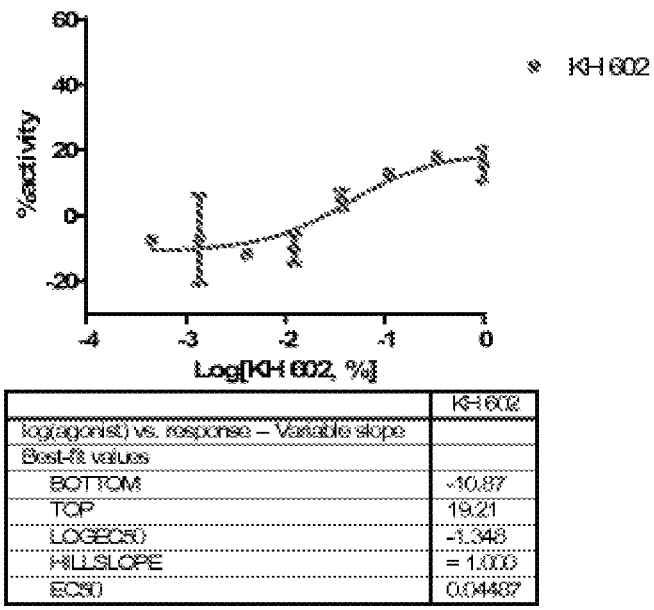
Figure 57E:
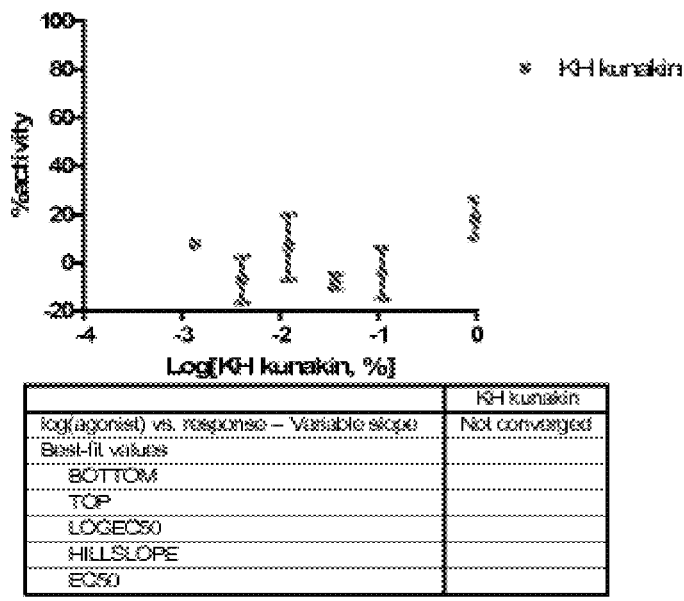
Figure 58A:
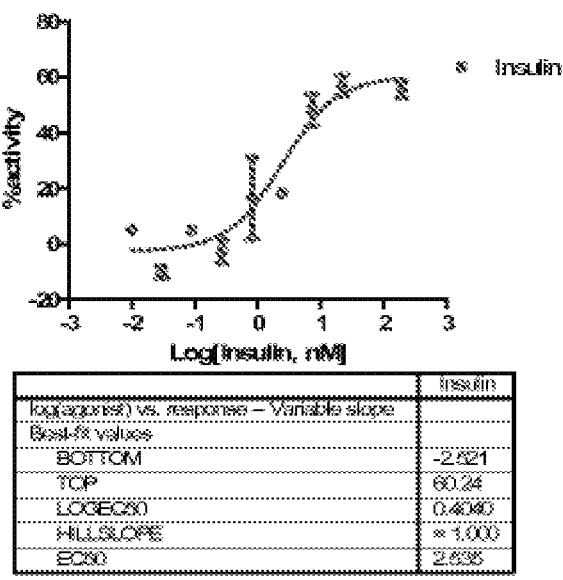
FIG. 58A-E show dose response curve fits for glucose uptake in 3T3-L1 adipocytes for insulin, KHG, KHB, KHJ, and KH103.
Figure 58B:
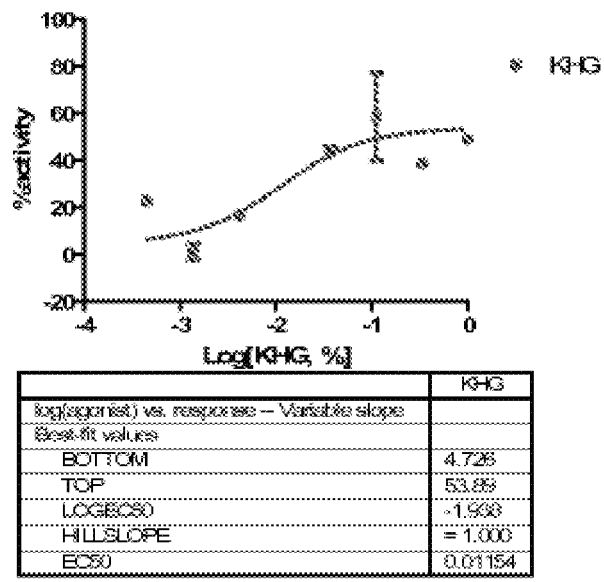
Figure 58C:
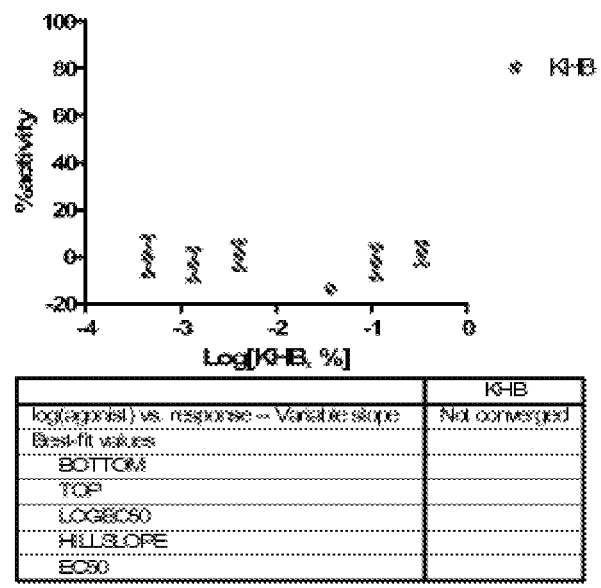
Figure 58D:
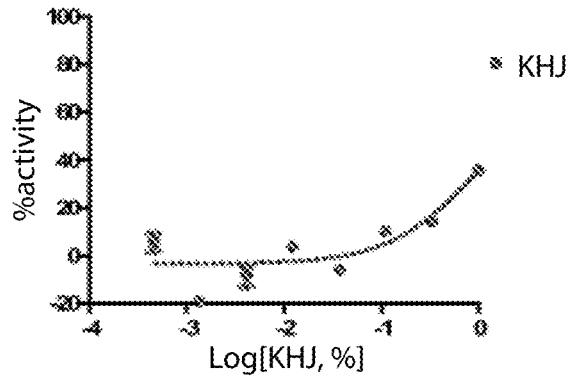
Figure 58E:
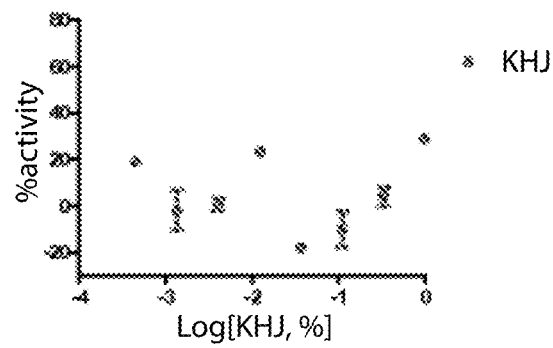
Figure 59A:
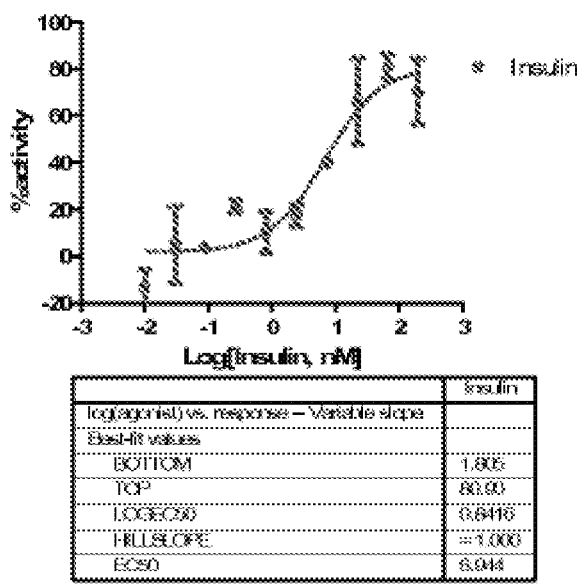
FIG. 59A-F show dose response curve fits for glucose uptake in 3T3-L1 adipocytes for insulin, KH410, KH601, KH602, KH kunakin, and KH409.
Figure 59B:
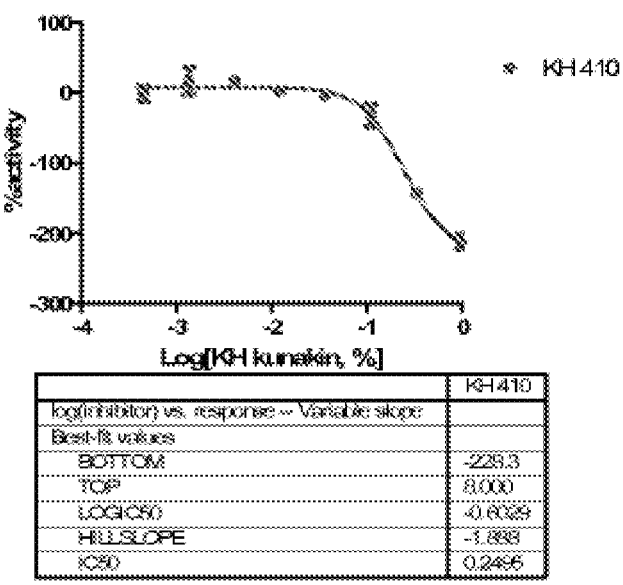
Figure 59C:
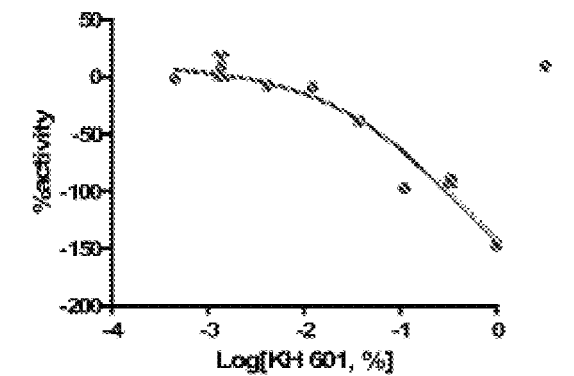
Figure 59D:
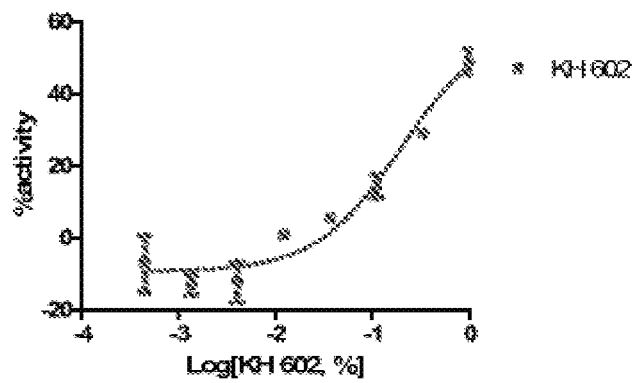
Figure 59E:
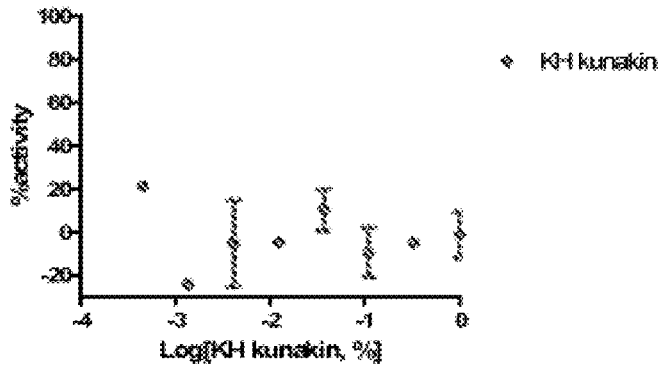
Figure 59F:
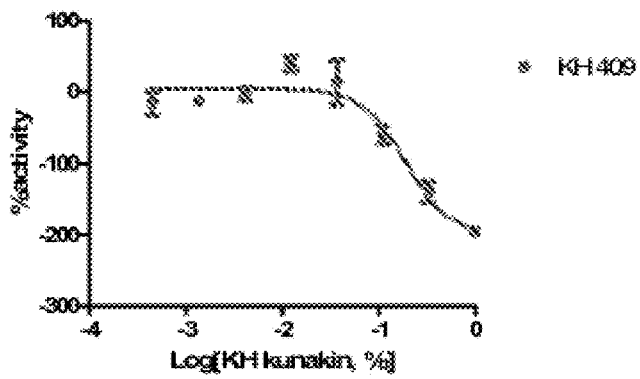
Figure 60A:
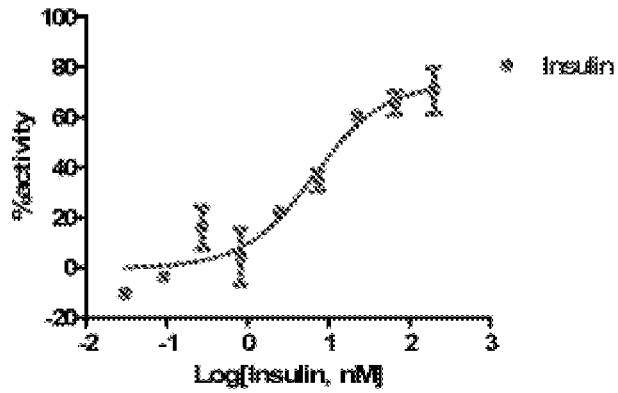
FIG. 60A-D show dose response curve fits for glucose uptake in 3T3-L1 adipocytes for insulin, KH111, KH409, and KH410.
Figure 60B:
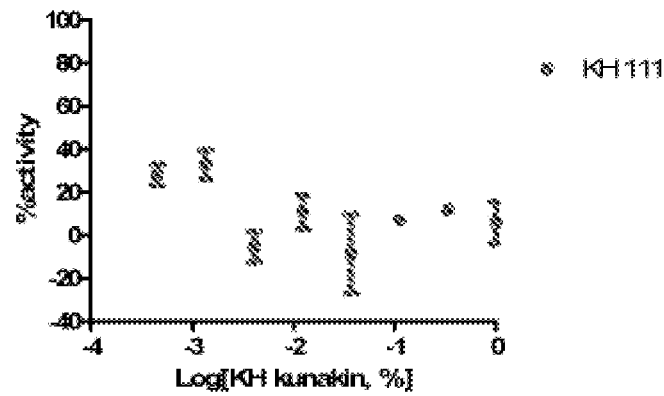
Figure 60C:
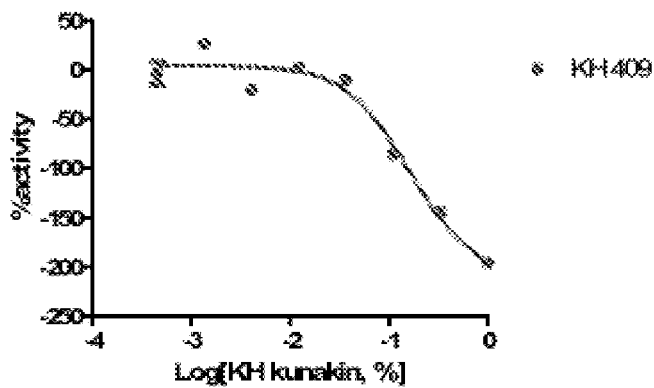
Figure 60D:
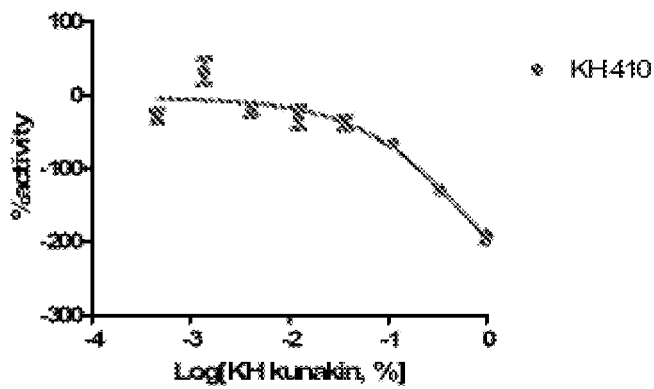

Animal body weight was monitored regularly as an indirect measure of toxicity (FIG. 54A-B). No group lost weight as a result of test article administration, except the prophylactic KHGD Group 4 which was found with sign of emaciation and dehydration due to the 3 days' whole-day supply of KHGD. The average body weight of KHGD-prophylactic group significantly dropped from 22.0 to 18.2 g in the first 3 days of prophylactic treatment, while 4 animals from this group presented severe body weight loss larger than 20%. The body weight change of KHGD-prophylactic group recovered from −17.1% to −2.3% after the dosing adjustment to 8 h on/16 h off.

Mice #419 and #370 from Group 6, treated by positive control Paclitaxel, died on day 20 and day 63 after the start of therapeutic treatment, possibly due to drug toxicity (abdominal distension was found before the death). The other mice did not appear to be overtly sick (Table 24).

TABLE 24

Mortality and mobility of the animals during the study

| Group | Treatment | Mortality | BWL > 20% | Subtotal mice# lost/N |
|---|---|---|---|---|
| 1 | Vehicle - prophylactic | 0 | 0 | 0/10 |
| 2 | KHJ - prophylactic | 0 | 0 | 0/10 |
| 3 | KH103 - prophylactic | 0 | 0 | 0/10 |
| 4 | KHGD - prophylactic | 0 | 4 (d3)[c] | 0/10 |
| 5 | Vehicle - therapeutic | 0 | 0 | 0/10 |
| 6 | Paclitaxel - therapeutic | 2[a] (D20, 63)[b] | 0 | 2/10 |
| 7 | KHJ - therapeutic | 0 | 0 | 0/10 |
| 8 | KH103 - therapeutic | 0 | 0 | 0/10 |
| 9 | KHGD - therapeutic | 0 | 0 | 0/10 |

Note:
[a]number of animals exhibited mortality or morbidity
[b]days after the start of therapeutic treatment
[c]days after the start of prophylactic treatment
Body weight change in female BALB/c nude mice bearing MDA-MB-436 xenografts dosed with KHJ, KH103 and KHGD are shown in FIG. 54A-B.

TABLE 25

Tumor growth inhibition calculation for KHJ, KH103, and KHGD in the MDA-MB-436 xenograft model calculated based on tumor volume measurements at day 71

| Group | Treatment | Tumor Size (mm³)[a] at day 71 | T/C[b] (%) | ΔTGI (%) | T-C (days) at 600 mm³ | p value[c] |
|---|---|---|---|---|---|---|
| 1 | Vehicle - Prophylactic | 1,480 ± 216 | — | — | — | — |
| 2 | KHJ - Prophylactic | 675 ± 264 | 46 | 57 | 15 | 0.112 |
| 3 | KH103 - Prophylactic | 657 ± 228 | 44 | 58 | 12 | 0.102 |
| 4 | KHGD - Prophylactic | 1,260 ± 364 | 85 | 16 | 4 | 0.859 |
| 5 | Vehicle - Therapeutic | 2,025 ± 264 | — | — | — | — |
| 6 | Paclitaxel - Therapeutic | 637 ± 211 | 31 | 71 | 23 | 0.006 |
| 7 | KHJ - Therapeutic | 1,370 ± 286 | 68 | 34 | 10 | 0.315 |
| 8 | KH103 - Therapeutic | 1,205 ± 359 | 60 | 42 | 13 | 0.150 |
| 9 | KHGD - Therapeutic | 2,015 ± 288 | 100 | 0 | 3 | 1.000 |

Note:
[a]Mean ± SEM at day 71 after inoculation.
[b]Tumor Growth Inhibition is calculated by dividing the group average tumor volume for the treated group by the group average tumor volume for the control group (T/C). ΔTGI was calculated using the formula: ΔTGI (%) = [1 − (Ti − T0)/(Vi − V0)] × 100.
[c]p value is calculated based on tumor size which is compared to the vehicle-prophylactice group in prophylaxis arms, and vehicle-therapeutic group in therapeutic arms.

TABLE 26

Tumor weights in different groups

| Group | Treatment | Tumor Weight (g)[a] at day 78 | T/C$_{weight}$[b] (%) | p value[c] |
|---|---|---|---|---|
| 1 | Vehicle - prophylactic | 1.44 ± 0.19 | — | — |
| 2 | KHJ - Prophylactic | 0.69 ± 0.27 | 47.9 | 0.149 |
| 3 | KH103 - Prophylactic | 0.69 ± 0.25 | 47.9 | 0.146 |
| 4 | KHGD - Prophylactic | 1.10 ± 0.35 | 76.4 | 0.720 |
| 5 | Vehicle - Therapeutic | 1.69 ± 0.31 | — | — |
| 6 | Paclitaxel - Therapeutic | 0.67 ± 0.23 | 39.6 | 0.053 |
| 7 | KHJ - Therapeutic | 1.40 ± 0.29 | 82.8 | 0.862 |
| 8 | KH103 - Therapeutic | 0.97 ± 0.25 | 57.4 | 0.198 |
| 9 | KHGD - Therapeutic | 1.96 ± 0.28 | 116.0 | 0.903 |

Note:
[a]Mean ± SEM at day 78 after inoculation.
[b]Tumor Growth Inhibition is calculated by dividing the tumor weight of the treated group by the tumor weight of the control group (T/C$_{weight}$)
[c]p value is calculated based on tumor weight which is compared to the vehicle-prophylactic group in prophylaxis arms, and vehicle-therapeutic group in therapeutic arms.

The therapeutic efficacies of KHJ, KH103, and KHGD in the treatment of the MDA-MB-436 human breast cancer xenograft model were evaluated. The results of tumor sizes in different groups at different time points after tumor inoculation are shown in Table 25 and FIG. 55A-B.

For the Prophylactic arms, the mean tumor size of the vehicle treated control mice reached 1,480 mm3 at day 71 after tumor inoculation. The treatment with the test article KHJ and KH103 with the dosing schedule detailed in Tables 21 and 22 produced significant antitumor activities. Their mean tumor sizes were 675 and 657 mm3, respectively at the same time (T/C value=46% and 44%, respectively; p=0.112 and 0.102) with the tumor growth delays of 15 and 12 days at tumor size of 600 mm³ compared with the vehicle group. The KHGD prophylactic treatment produced a minor antitumor activity with a mean tumor size of 1,260 mm³ (T/C value=85%), and delayed tumor growth by only 4 days with the p value=0.859 compared to the vehicle group.

For the Therapeutic arms, the mean tumor size of the vehicle treated control mice reached 2,025 mm³ at day 71 after tumor inoculation. The treatment of positive control agent Paclitaxel (1.5 mg/kg, BIW×9 weeks) produced a statistically significant antitumor activity, with a mean tumor sizes of 637 (T/C value=31%; p=0.006) with the tumor growth delay of 23 days at tumor size of 600 mm³ compared with the vehicle group. Meanwhile, the KHJ and KH103 therapeutic treatments exhibited moderate antitumor efficacy. Their mean tumor sizes were 1,370 and 1,205 mm$^3$ at the same time (T/C value=68% and 60%, respectively; p=0.315 and 0.150), delaying the tumor growth to 600 mm$^3$ for 10 and 13 days. The KHGD Therapeutic treatment was tolerated well by the tumor-bearing animals, and delayed tumor growth to 600 mm$^3$ by only 3 days, and produced no tumor inhibition at study termination.

The results of the tumor weights (Table 26) are essentially consistent with the tumor volumes.

The test agents KHJ, KH103, and KHGD were all tolerated well by the tumor-bearing animals. No body weight loss was observed in all of treatment groups except the 7 mice in KHGD Prophylactic treatment group which had body weight loss of 16.7-26.1% due to 3 days' whole-day supply of KHGD, but all animals recovered after the dosing adjustment.

In summary, the test agents KHJ and KH103 dosed as shown in Tables 21 and 22 produced moderate antitumor activities against the MDA-MB-436 human breast cancer xenograft model. All 3 test agents, KHJ, KH103, and KHGD, were well tolerated by the tumor-bearing animals.

DIO Mice Study

The efficacy of RAAS products in mice was evaluated according to the following experimental design of therapeutics in diet-induced obesity (DIO) mice.

DIO mice creation: After one-week acclimation, the mice are fed a high fat pelleted diet (D12492i; Research Diets, Inc) and fresh water, ad libitum. Typically, C57BL/6J male mice become obese, mildly to moderately hyperglycemic and develop impaired glucose tolerance after 12-14 weeks of high fat diet treatment. Mice are preferably 40-50 g or greater at the time of the study.

Group setting (n=10, 4 mice for immunology):

| | |
|---|---|
| Atorvastatin | tid po 10 mL/kg + ad libitum water |
| Vehicle control | tid po 10 mL/kg + ad libitum water |
| Kunakin (KH103) therapeutic | tid po 10 mL/kg + ad libitum |
| Kunamin (KHJ) therapeutic | tid po 10 mL/kg + ad libitum |
| Kh gold (KHGD) therapeutic | tid po 10 mL/kg + ad libitum water in the night |

Animals were allowed free access to high fat diet and test articles (water) for 60 days. Body weight and food intake were recorded twice per week.

Figure 68:
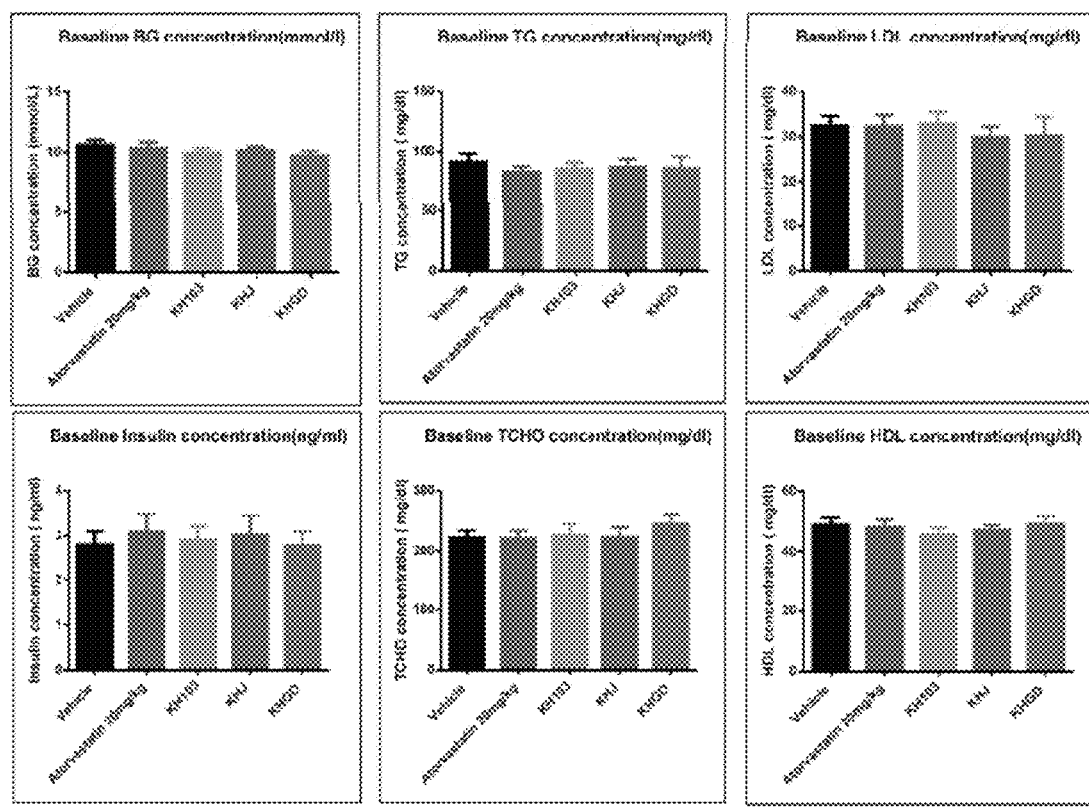
FIG. 68 shows the baseline of the bio-markers in blood/plasma of the mice.

BG, insulin, TG, HDL-C, LDL-C, and TCHO in plasma once per two weeks (baseline were tested before study start (FIG. 68)). Data were analyzed and graphed by Graph Pad Prism.

Figure 61A:
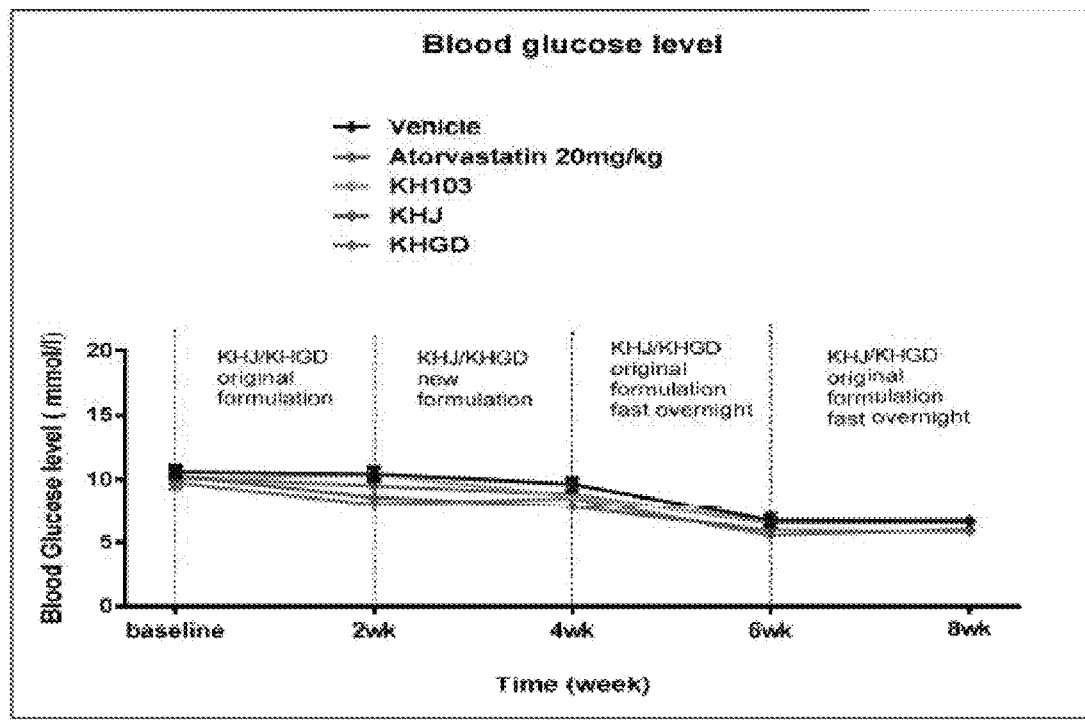
FIG. 61A-B show graphs depicting blood glucose levels and $AUC_{(0-8\ weeks)}$.
Figure 61B:
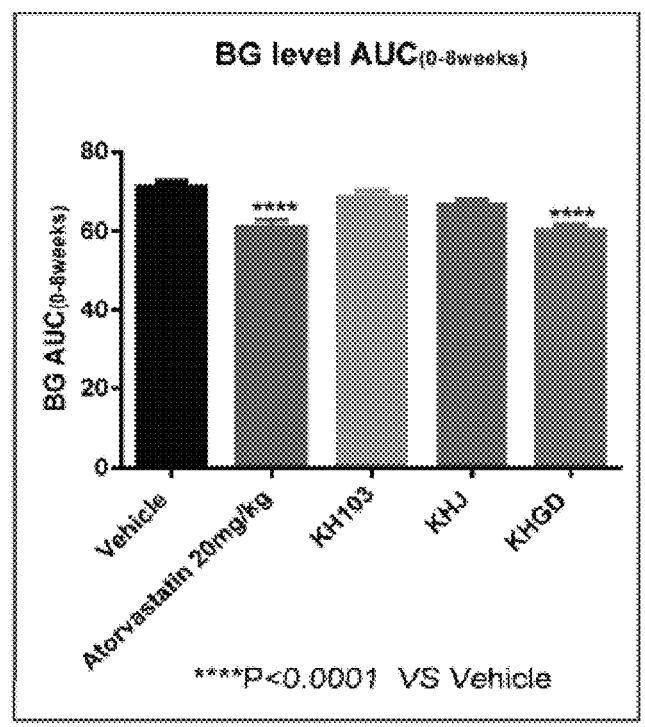

FIG. 61A-B show graphs depicting blood glucose levels and AUC$_{(0-8\ weeks)}$. Atorvastatin 20 mg/kg as positive control significantly decrease the blood glucose level. The KHGD significantly decrease the blood glucose level.

Figure 62A:
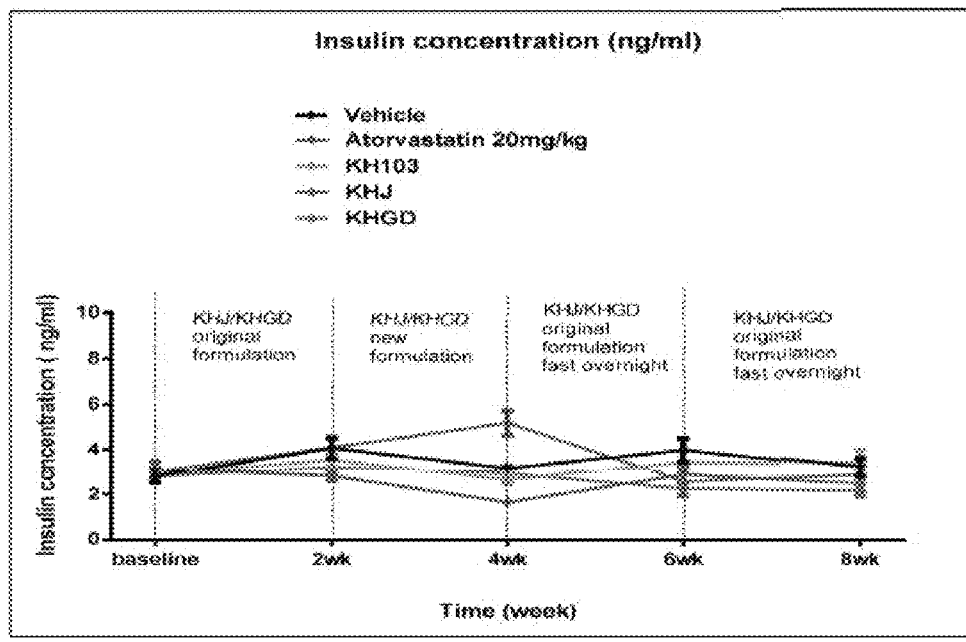
FIG. 62A-B show graphs depicting insulin levels and $AUC_{(0-8\ weeks)}$.
Figure 62B:
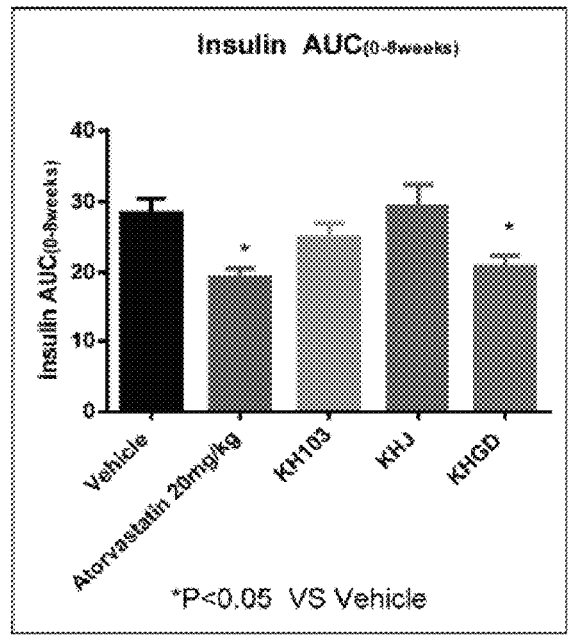

FIG. 62A-B show graphs depicting insulin levels and AUC$_{(0-8\ weeks)}$. Atorvastatin 20 mg/kg as positive control significantly increase the insulin sensibility. The KHGD significantly increase the insulin sensibility.

Figure 63A:
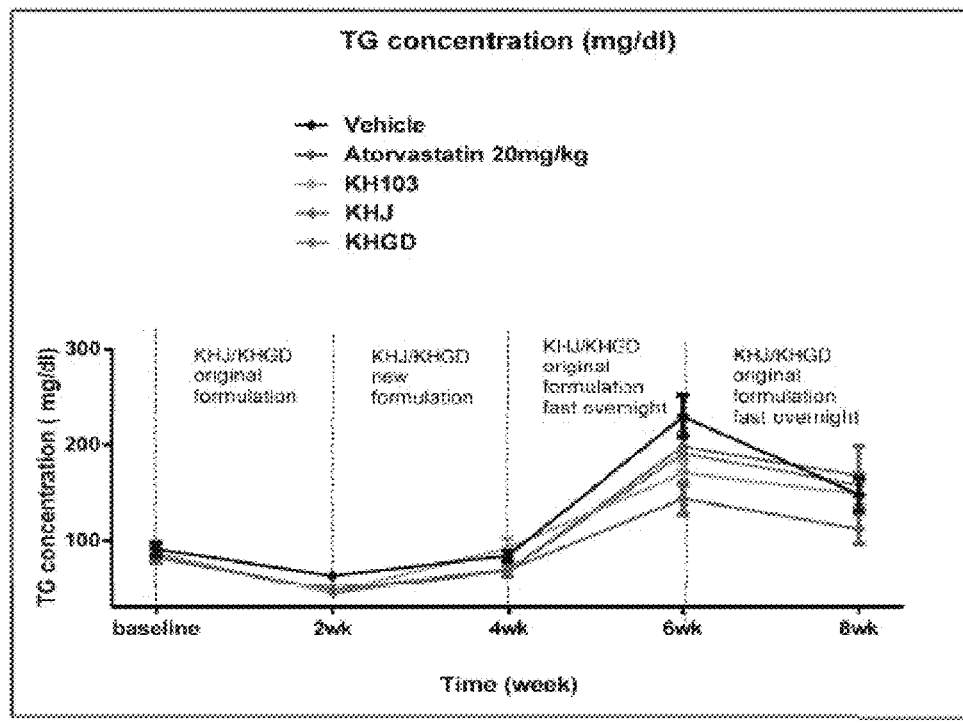
FIG. 63A-B show graphs depicting plasma TG levels and $AUC_{(0-8\ weeks)}$.
Figure 63B:
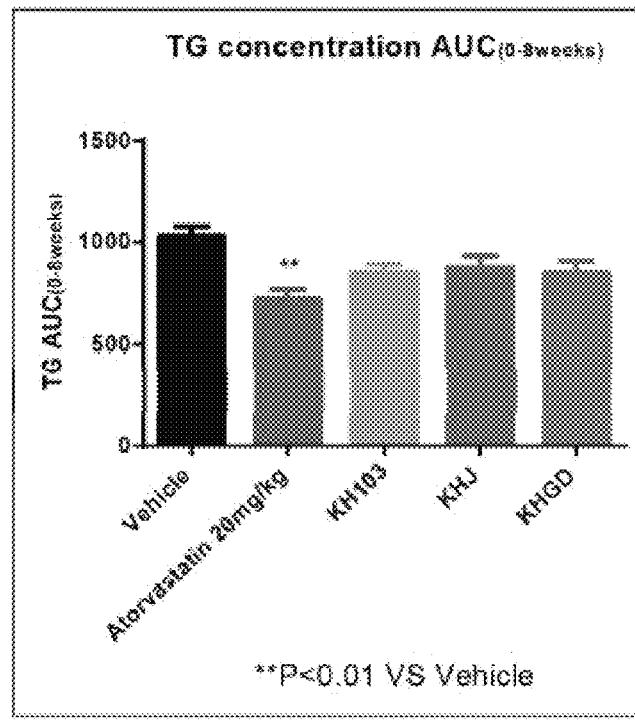

FIG. 63A-B show graphs depicting plasma TG levels and AUC$_{(0-8\ weeks)}$. Atorvastatin 20 mg/kg as positive control significantly decrease the plasma TG level. All the test articles have a trend to decrease the plasma TG level.

Figure 64A:
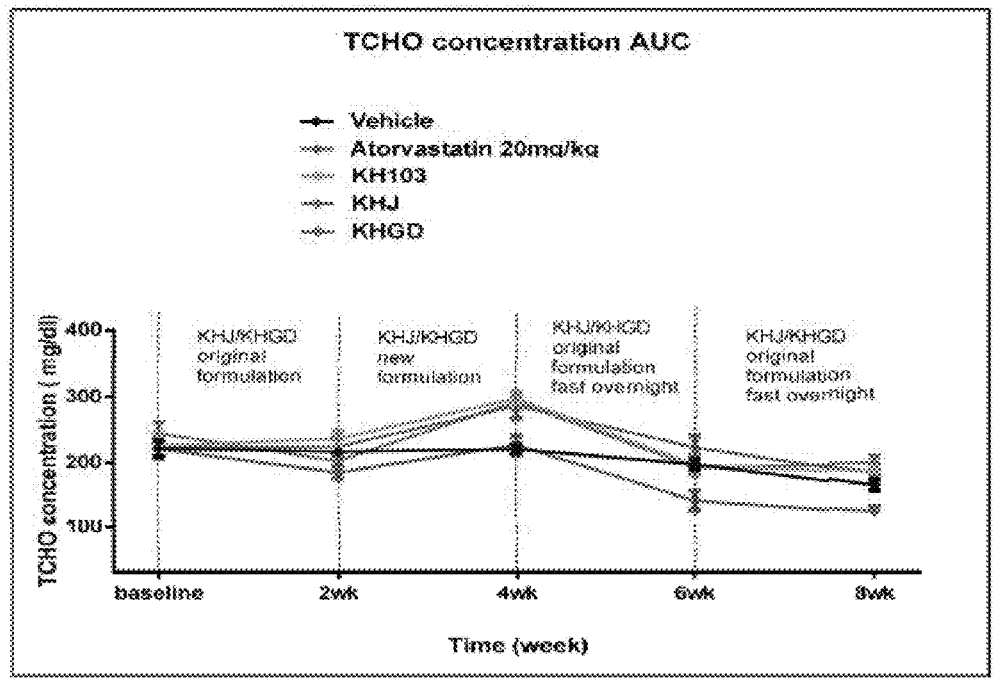
FIG. 64A-B show graphs depicting plasma TCHO levels and $AUC_{(0-8\ weeks)}$.
Figure 64B:
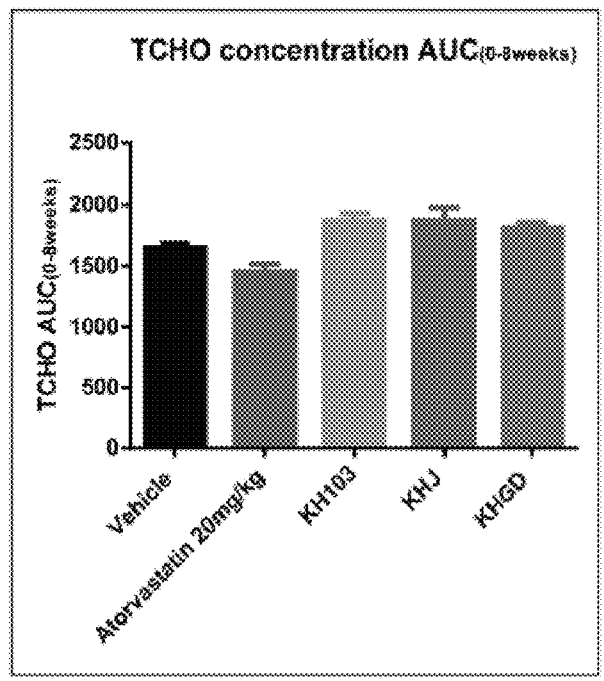

FIG. 64A-B show graphs depicting plasma TCHO levels and AUC$_{(0-8\ weeks)}$. Atorvastatin 20 mg/kg as positive control have a trend to decrease the plasma TCHO level. All the test articles have no effects on the plasma TCHO level.

Figure 65A:
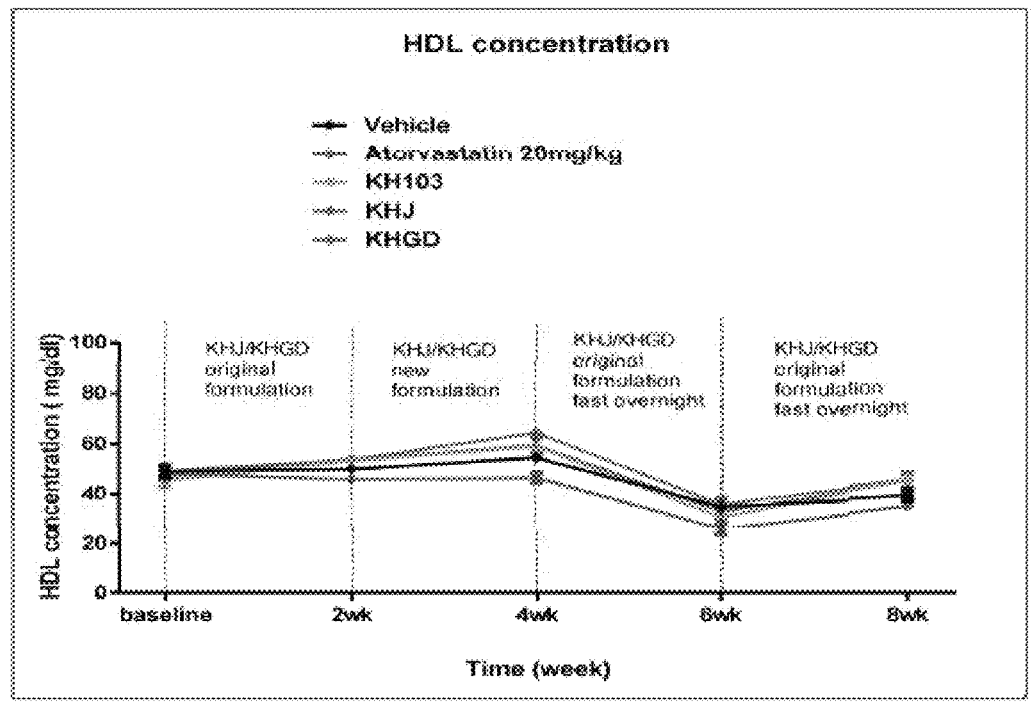
FIG. 65A-B show graphs depicting plasma HDL levels and $AUC_{(0-8\ weeks)}$.
Figure 65B:
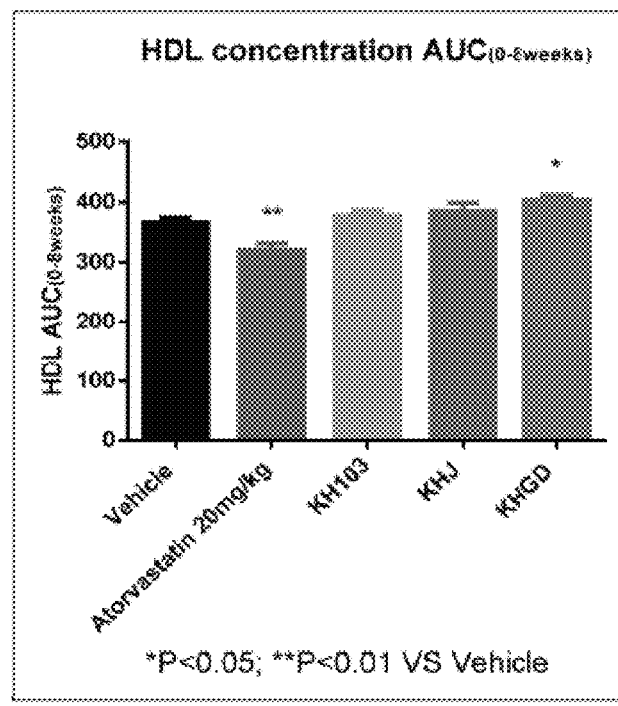

FIG. 65A-B show graphs depicting plasma HDL levels and AUC$_{(0-8\ weeks)}$. Atorvastatin 20 mg/kg as positive control significantly decrease the plasma HDL level. The KHGD significantly increase the plasma HDL level.

Figure 66A:
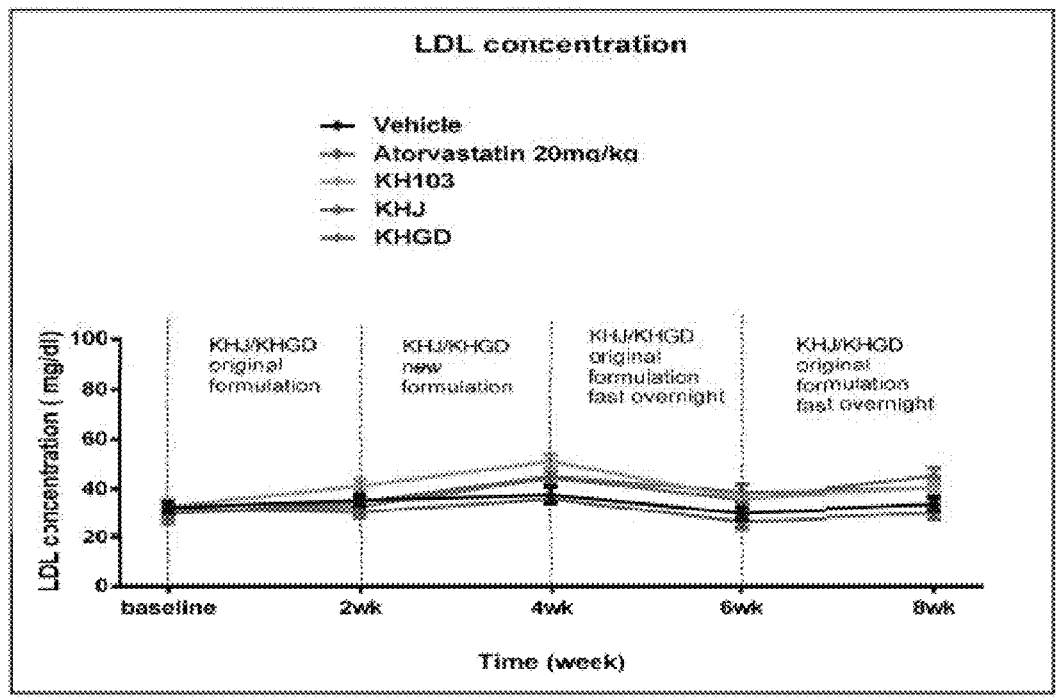
FIG. 66A-B show graphs depicting plasma LDL levels and $AUC_{(0-8\ weeks)}$.
Figure 66B:
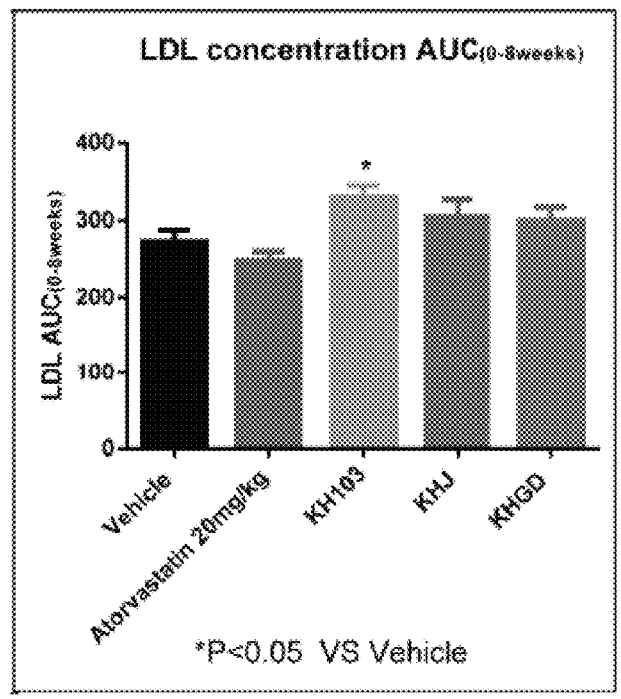

FIG. 66A-B show graphs depicting plasma LDL levels and AUC$_{(0-8\ weeks)}$. Atorvastatin 20 mg/kg as positive control have a trend to decrease the plasma LDL level. All the test articles have no effects on the plasma LDL level.

Figure 67A:
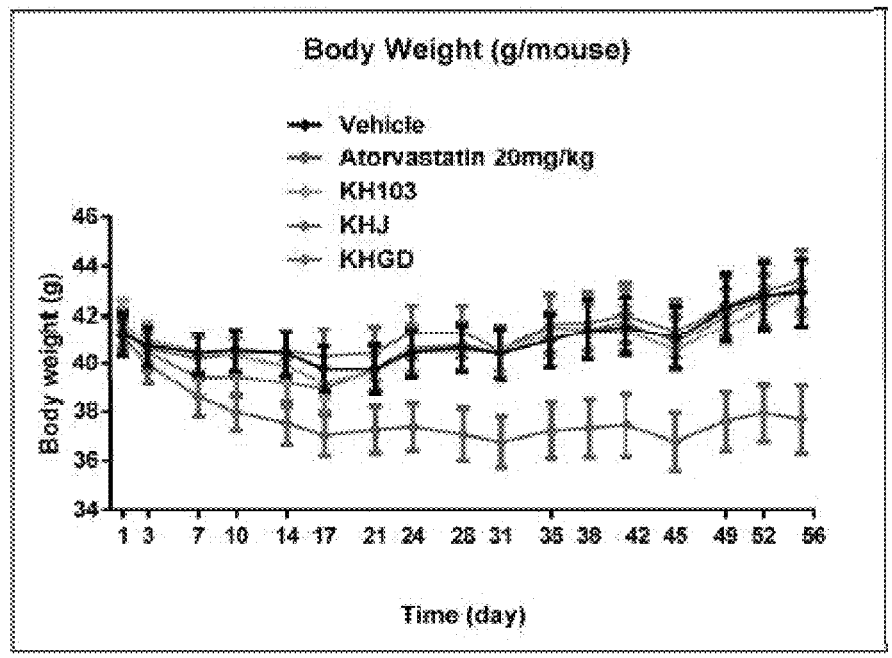
FIG. 67A-B show graphs depicting body weight and food intake of the mice.
Figure 67B:
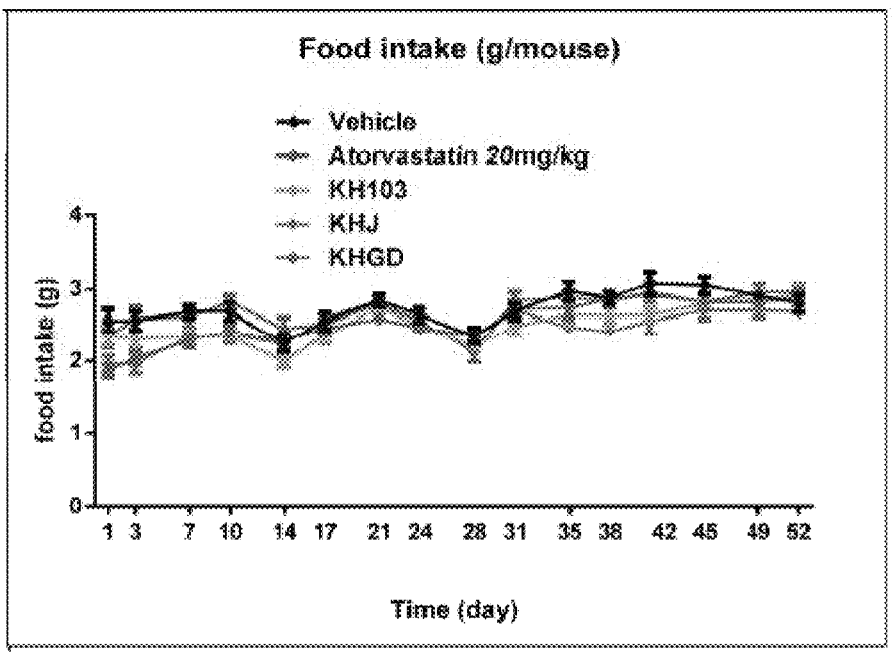

FIG. 67A-B show graphs depicting body weight and food intake of the mice. Atorvastatin 20 mg/kg as positive control significantly decrease the body weight of the DIO mice. All the test articles have no effects on the body weight and food intake of the DIO mice.

Next step: add an OGTT study for the mice before the end of the study. Blood glucose tolerance test should be more sensitive than the blood glucose and insulin.

The terminal liver samples were collected for bio-marker analysis. The improvement in liver could also reflect the efficacy of the testing articles.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

I claim:

1. A method of treating leukemia in a human in need thereof consisting essentially of administering a therapeutically effective amount of a composition of grape seed and grape stem to said human in need thereof to effectively treat the leukemia in said human in need thereof.

2. The method of claim 1, wherein the composition of grape seed and grape stem is ground to form a pomace and wherein the composition is a juice formed from the pomace.

3. The method of claim 1, wherein the composition of grape seed and grape stem is ground to form a pomace and wherein the composition is a powder formed from the pomace.

4. The method of claim 1, wherein the composition of grape seed and grape stem is ground to form a pomace and wherein the composition is a wine formed from the pomace.

5. The method of claim 1, wherein the composition of grape seed and grape stem is ground into a juice by a grinder at 20° C.-30° C. and then the juice is fermented at 23° C.-24° C. into a wine.

6. The method of claim 1, wherein the composition of grape seed and grape stem is ground into a juice by a grinder at 20° C.-30° C., then the juice is fermented at 23° C.-24° C. into a wine, and then the wine is spray dried to form a powder.

* * * * *